United States Patent
Hancock et al.

(10) Patent No.: US 12,043,602 B2
(45) Date of Patent: Jul. 23, 2024

(54) FENDILINE DERIVATIVES

(71) Applicant: The Board of Regents of the University of Texas System, Austin, TX (US)

(72) Inventors: John F. Hancock, Houston, TX (US); Jia Zhou, Galveston, TX (US); Dharini van der Hoeven, Houston, TX (US); Jeffrey A. Frost, Houston, TX (US); Na Ye, Jiangsu (CN); Pingyuan Wang, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 123 days.

(21) Appl. No.: 17/437,024

(22) PCT Filed: Mar. 5, 2020

(86) PCT No.: PCT/US2020/021274
§ 371 (c)(1),
(2) Date: Sep. 7, 2021

(87) PCT Pub. No.: WO2020/181143
PCT Pub. Date: Sep. 10, 2020

(65) Prior Publication Data
US 2022/0177440 A1    Jun. 9, 2022

Related U.S. Application Data

(60) Provisional application No. 62/814,251, filed on Mar. 5, 2019.

(51) Int. Cl.
*C07D 295/13*    (2006.01)
(52) U.S. Cl.
CPC ................... *C07D 295/13* (2013.01)
(58) Field of Classification Search
CPC .................................... C07D 295/13
See application file for complete search history.

(56) References Cited

PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URLhttp:/Awww.nlm.nih.gov/medlineplus/cancer.html>.*

* cited by examiner

*Primary Examiner* — Shawquia Jackson
(74) *Attorney, Agent, or Firm* — HYLTON-RODIC LAW PLLC

(57) ABSTRACT

The invention relates generally to the following novel fendiline derivatives, and the preparation and use thereof: Formula I (I) and Formula II (II)

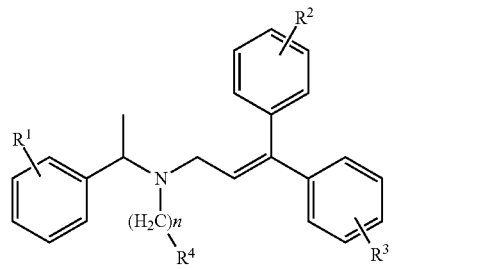

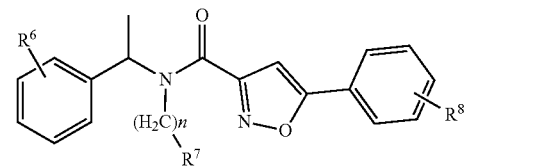

7 Claims, 15 Drawing Sheets

Fendiline

NY0244

NY0331

PW454

NY0335

A. K-Ras mislocalization

| Compound | IC50 (μM) | Emax |
|---|---|---|
| R-Fendiline | 5.59 | 0.811 |
| NY0244 | 0.19 | 0.918 |
| NY0331 | 0.28 | 0.883 |
| NY0335 | 0.021 | 0.769 |
| NY0506 | 0.528 | 0.977 |
| NY0513 | 0.639 | 0.786 |
| PW323 | 0.05 | 0.852 |
| PW454 | 0.319 | 0.771 |

B.

Fendiline derivatives in ADMET assays

A. K-Ras mislocalization

| Compound | IC50 (µM) | Emax |
|---|---|---|
| R-Fendiline | 5.59 | 0.811 |
| NY0244 | 0.19 | 0.918 |
| NY0331 | 0.28 | 0.883 |
| NY0335 | 0.021 | 0.769 |
| NY0506 | 0.528 | 0.977 |
| NY0513 | 0.639 | 0.786 |
| PW323 | 0.05 | 0.852 |
| PW454 | 0.319 | 0.771 |

B. Cell permeability assay

| Compound | Efflux Ratio | P-gp substrate |
|---|---|---|
| Fendiline | 5.83 | Yes |
| NY0244 | 16.74 | Yes |
| NY0331 | 850.84 | Yes |
| NY0335 | 69.93 | Yes |
| NY0506 | 11.56 | Yes |
| NY0513 | 30.04 | Yes |
| PW323 | ? | ? |
| PW454 | ? | ? |

C. CYP450 inhibition assay

| Compound | CYP2D6 (Dextromethorphan) | HLM CYP inhibition IC50 (µM) | | |
|---|---|---|---|---|
| | | CYP3A4 (Midazolam) | CYP3A4 (Testosterone) | CYP3A4 (Nifedipine) |
| Fendiline | 0.1 | 15.0 | 6.0 | 8.9 |
| NY0244 | 0.1946 | 2.1220 | 2.4327 | 3.1348 |
| NY0331 | 0.01 | 1.4 | 1.9 | 3.8 |
| NY0335 | 0.07 | 1.0 | 2.4 | 2.7 |
| NY0506 | 0.0467 | 5.7406 | 5.1989 | >33 |
| NY0513 | 0.1580 | 2.0932 | 5.0107 | >33 |
| PW323 | ? | ? | ? | ? |
| PW454 | ? | ? | ? | ? |

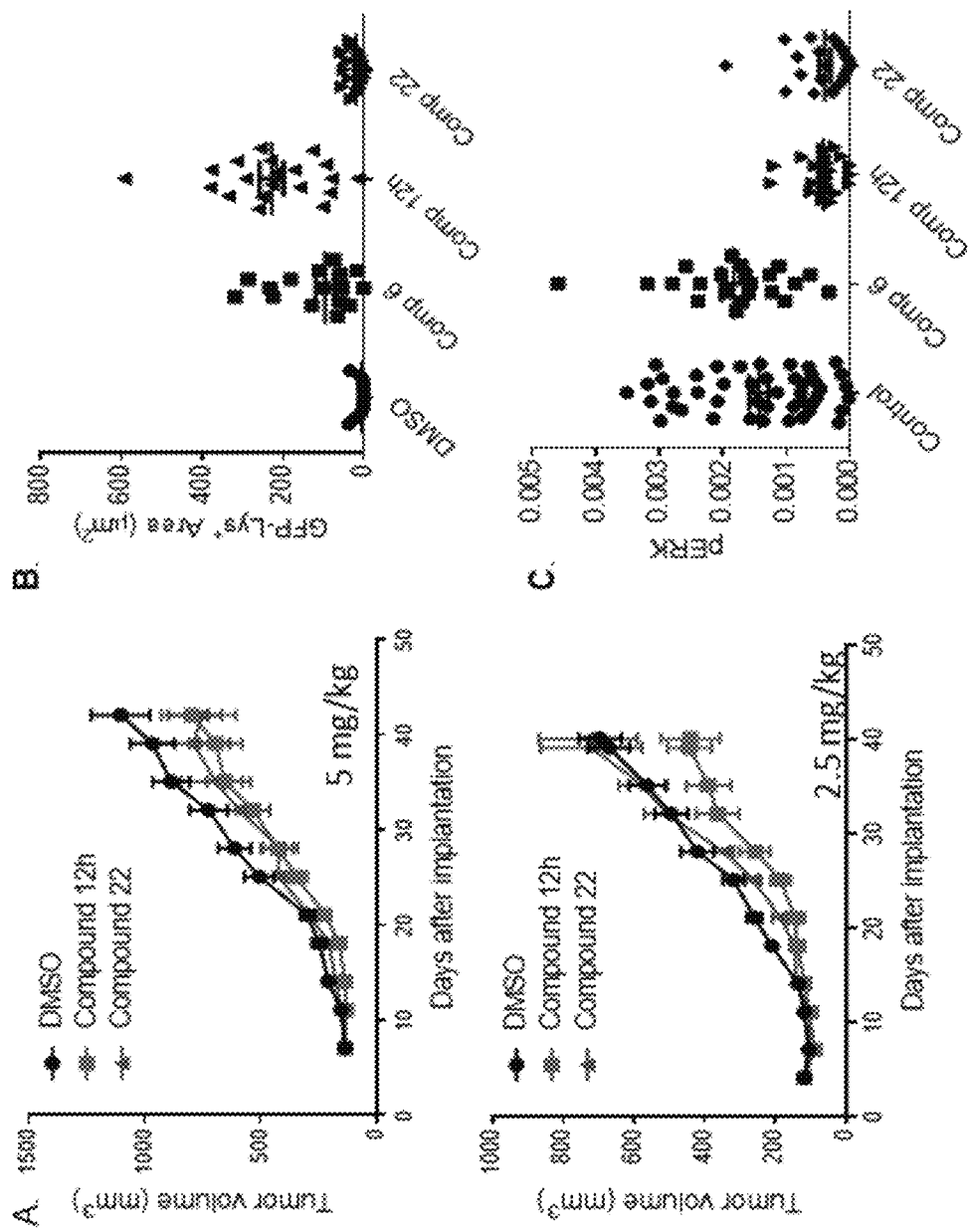
FIG. 8A-C

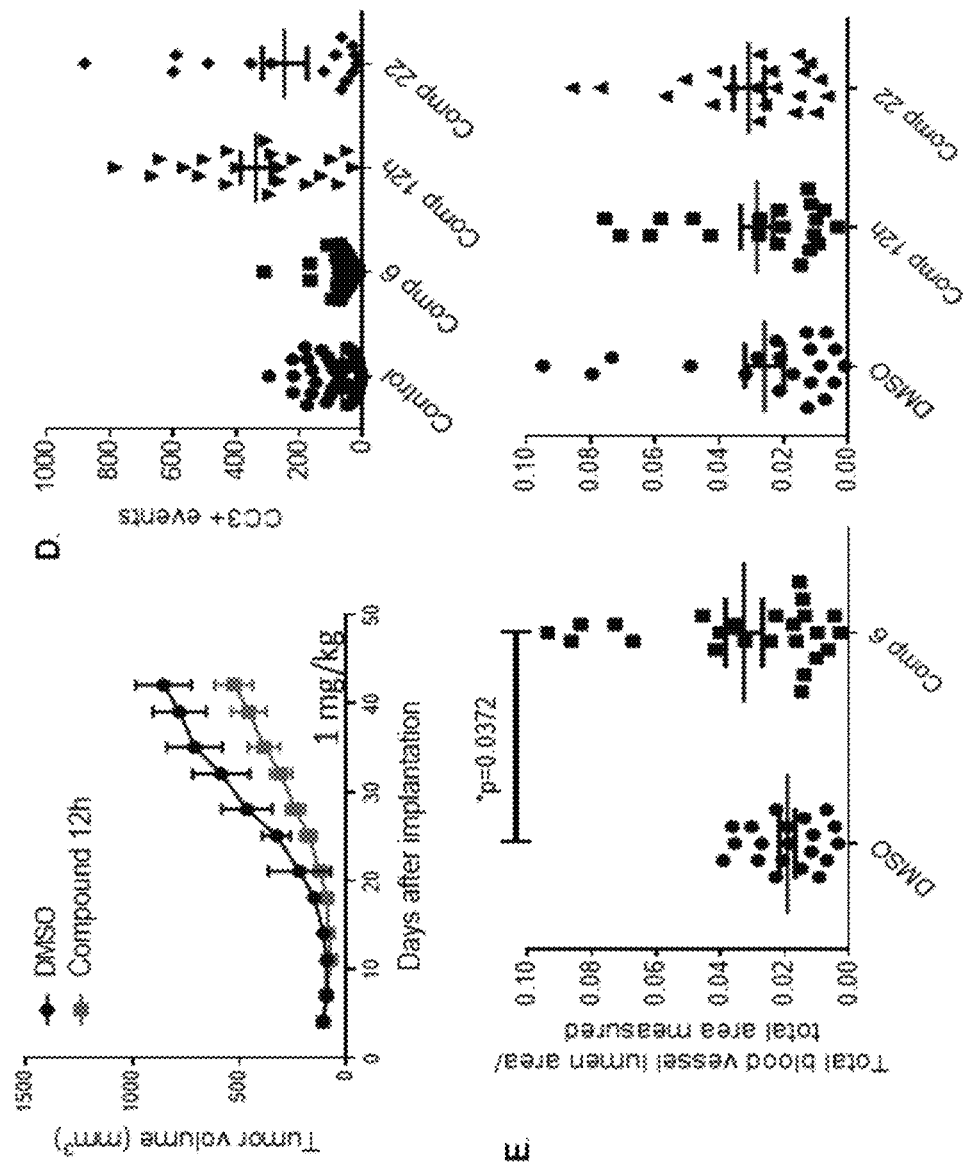
FIG. 8D-E

FENDILINE DERIVATIVES

CROSS REFERENCE TO RELATED APPLICATIONS

This application is a U.S. national stage application of International Application No. PCT/US20/21274, filed Mar. 5, 2020, which claims the benefit of U.S. Provisional Appl. No. 62/814,251, filed Mar. 5, 2019. The content of the foregoing application is relied upon and is incorporated by reference herein in its entirety.

FIELD OF THE INVENTION

The field of the invention relates generally to novel fendiline derivatives, and the preparation and use thereof.

BACKGROUND

The Ras protein family members belong to a class of proteins called small GTPases. These are involved in transmitting signals within cells (cellular signal transduction). Ras proteins are related in their three-dimensional structure and regulate diverse cell behaviors. When Ras is "switched on" by incoming signals, it subsequently switches on other proteins, which ultimately turn on genes involved in cell growth, differentiation and survival. As a result, mutations in ras genes can lead to the production of permanently activated Ras proteins. This can cause inappropriate and overactive signaling inside the cell, even in the absence of incoming signals, which ultimately turn on genes involved in cell growth, differentiation and survival. As a result, mutations in ras genes can lead to the production of permanently activated Ras proteins. Overactive Ras signaling can ultimately lead to cancer. Ras is the most common oncogene in human cancer. Mutations that permanently activate Ras are found in 20-25% of all human tumors and up to 90% in certain types of cancer (e.g., pancreatic cancer). Clinically notable members of the Ras subfamily are HRAS, NRAS and KRAS, mainly for being implicated in many types of cancer. Inappropriate activation of the ras gene has been shown to play a key role in signal transduction, proliferation and malignant transformation.

Significant efforts have been made to pharmacologically target KRAS albeit mainly through the development of inhibitors of kinases downstream of KRAS. Direct targeting of KRAS has proven more challenging, 4 although significant progress has been achieved with efficacious small molecules that block the interactions between KRAS and the RAS exchange factor son of sevenless (SOS) and molecules that target the guanine nucleotide binding pocket of KRAS G12C, allowing the development of KRAS G12C irreversible inhibitors. Several potent and highly selective KRAS G12C inhibitors (e.g. AMG51023 and MRTX849) are currently advanced into human clinical trials. Nevertheless, such compounds are likely only be useful in the 15% of KRAS tumors that harbor a G12C mutation.

Newly synthesized KRAS undergoes post-translational modification of the C-terminal CAAX motif (C=cysteine; A=isoleucine; X=serine or methionine) that is required for localization to the inner leaflet of the plasma membrane (PM). After farnesylation by farnesyltransferase (FTase), the AAX residues are cleaved off by Ras-converting enzyme 1 (RCE1) and the now C-terminal farnesylated cysteine is methylated by isoprenylcysteine carboxylmethyltransferase 1 (ICMT1). PM localization (PML) is essential for KRAS function, and therefore, blocking oncogenic KRAS-driven signaling by preventing PM localization represents an appealing strategy. Initial attempts to block KRAS processing and PM localization using FTase inhibitors such as Tipifarnib (Compound 1), Lonafarnib (Compound 2) and BMS214662 (Compound 3) were unsuccessful because KRAS is alternatively prenylated by geranylgeranyltransferase type I (GGTase I) in FTI treated cells. Recent findings that KRAS released from endosomes is captured by the chaperone protein phosphodiesterase δ (PDE6) that delivers it to the recycling endosome (RE) for forward transport back to the PM led to the development of small molecule PDEδ inhibitors such as Deltarasin (Compound 4) and Deltazinone 1 (Compound 5), as inhibitors of KRAS PM localization. However, toxicity concerns are raised because PDEδ has a crucial role in regulating the function of many other prenylated GTPases. 10 Inhibitors of RCE1 and ICMT are under development, but these agents will also target CAAX processing of geranylgeranylated Rho family GTPases. Thus the development of potent and selective KRAS PM localization inhibitors is still an urgent need, not only for clinical use, but also as useful chemical probes and pharmacological tools to study KRAS-associated signaling pathways.

Localization of K-ras to the plasma membrane is important in order to activate downstream effector pathways. Fendiline hydrochloride had been identified as specific inhibitor of plasma membrane localization of K-Ras. Fendiline has the following formula:

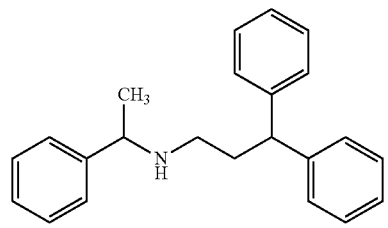 [SMILES: CC(NCCC(c1ccccc1)c1ccccc1)c1ccccc1]

Given these promising properties, that the biological activity profiles of known fendiline derivatives vary, and in view of the wide variety of diseases that may be treated or prevented with compounds that inhibit K-ras localization to the plasma membrane, as well as the degree of unmet medical need represented within this variety of diseases, there is a need for new fendiline derivatives with diverse structures that having desirable biological activity profiles for the treatment of one or more indications.

Fendiline (6) has attractive activity as a KRAS PM localization inhibitor, and is a calcium channel blocker that was previously used as a coronary vasodilator for the treatment of angina. The R isomer of compound 6 selectively mislocalized KRAS from the PM with an IC50 of approximately 5.6 µM, but had no effect on the PM localization of HRAS or NRAS. Mechanistic studies indicated that compound 6 decreased PM phosphatidylserine (PtdSer) and cholesterol levels through inhibition of acid sphingomyelinase (ASM) and further showed that KRAS mislocalization was a direct consequence of reduced PM PtdSer content. Compound 7 was found to exhibit 10-fold increased potency. However, compound 7 showed no capability to kill the mutant KRAS expressing cancer cells even at a high concentration of 30 µM likely due to its high cLogP value indicating high lipophilicity and poor druglike properties for further preclinical development. 4

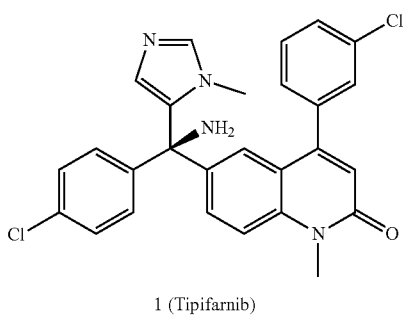

1 (Tipifarnib)

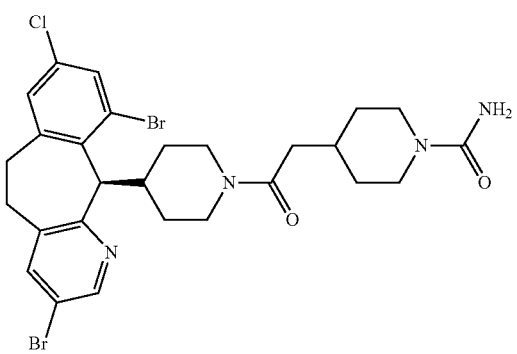

2 (Lonafarnib)

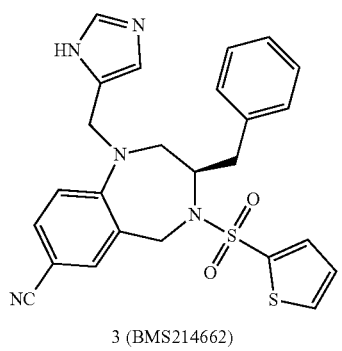

3 (BMS214662)

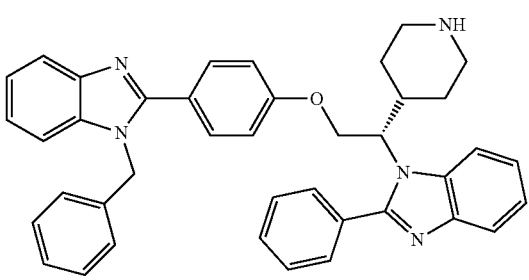

4 (Deltarasin)

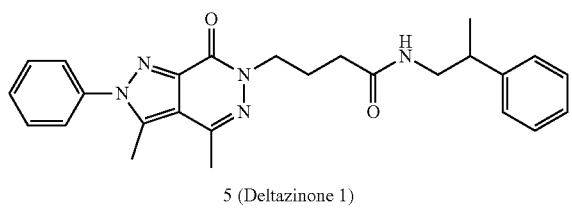

5 (Deltazinone 1)

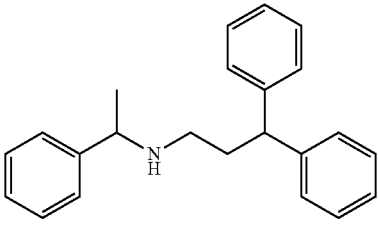

6 (Fendiline)

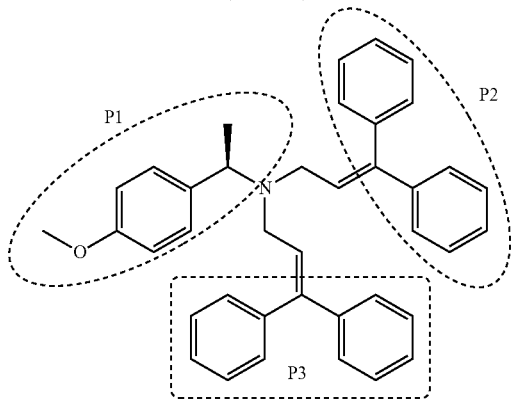

7

Compounds 12f (NY0244), 12h (NY0331) and 22 (NY0335), exemplary embodiments of the invention, were found to exhibit nanomolar potencies. These compounds inhibited oncogenic KRAS-driven cancer cell proliferation at low micromolar concentrations in vitro. In vivo studies in a xenograft model of pancreatic cancer revealed that 12h (NY0331) and 22 (NY0335) suppressed oncogenic KRAS-expressing MiaPaCa-2 tumor growth at a low dose range of 1-5 mg/kg with no vasodilatory effects, indicating their potential for chemical probes and anticancer therapeutics.

This background information is provided for the purpose of making information believed by the applicant to be of possible relevance to the present invention. No admission is necessarily intended, nor should it be construed, that any of the preceding information constitutes prior art against the present invention.

SUMMARY

The inventors have surprisingly discovered novel fendiline derivatives, as exemplified by compounds NY0244, NY0331, NY0506 and PW0323, modulate KRAS activity.

One aspect of the invention pertains to compounds of Formula I or pharmaceutically acceptable salts thereof, wherein:

Formula I

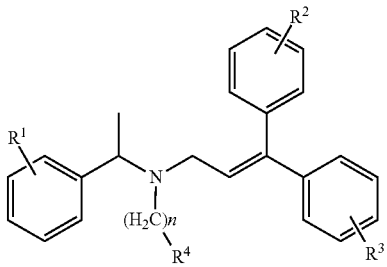

wherein:
R' is independently chosen from H, alkyl, alkoxy, X, cyano, amino, nitro, hydroxyl, $CX_3$ and $—OCX_3$ wherein X is F, Cl, Br, or I;
$R^2$ is H, alkyl, alkoxy, X, cyano, amino, nitro, hydroxyl and $CX_3$;
$R^3$ is independently chosen from H, alkyl, alkoxy, X, cyan, amino, nitro, hydroxyl and $CX_3$
$R^4$ is independently chosen from a 5-membered heterocycle and a 6-membered heterocycle; and
n is 1-6.

Another aspect of the invention pertains to compounds of Formula II or pharmaceutically acceptable salts thereof, wherein:

Formula II

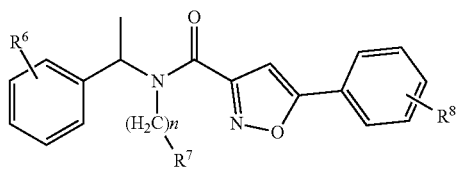

$R^6$ is independently chosen from H, alkyl, alkoxy, X, cyano, amino, hydroxyl and $CX_3$ and $—OCX_3$, wherein X is F, Cl, Br, or I;
$R^7$ is independently chosen from a 5-membered heterocycle and a 6-membered heterocycle;
$R^8$ is H, alkyl, alkoxy, X, cyano, amino, hydroxyl and $CX_3$; and
n is 1-6.

In some embodiments, the invention encompasses use of the compounds of the invention to modulate and/or treating a K-Ras mediated disorders such as various cancers and inflammatory diseases in a subject.

It is to be understood that both the foregoing general description of the invention and the following detailed description are exemplary, and thus do not restrict the scope of the invention.

BRIEF DESCRIPTION OF THE FIGURES

FIG. 3. K-RAS inhibition, cell permeability and CYP inhibition properties of the most potent fendiline derivatives. (A) Potency (IC50) and Efficacy (Emax) of the most potent fendiline-derivatives identified in K-RAS mislocalization assay (same as Figure, part (A)). (B) MDCK cells expressing human MDR1 gene (encodes P-gp, an important drug transporter) were grown as monolayers in 12-multiwell Transwell systems. 72 h post-seeding, drugs were added to apical or basolateral sides and incubated for 90 min following which both apical and basolateral samples were analyzed by LC-MS/MS. Permeability coefficients (Papp) of drugs from apical to basolateral (Papp, A>B) and basolateral to apical (Papp B>A) and Efflux Ratios were calculated. Efflux Ration of >2 indicates drug efflux by P-gp. (C) Activities of major human CYP1A2, CYP2C9, CYP2C19, CYP2D6 and CYP3A4 isozymes in human liver microsomes were measured in the presence of drugs using isoform-specific probe substrates. B and C were conducted by Alliance Pharma, Inc.

FIG. 8A-E. (A) Nu/nu mice implanted with MiaPaCa-2 tumors were treated with vehicle (DMSO) or compounds intraperitoneally and tumor sizes were measured with an external caliper every 3-4 days. (B) Tumor sections were stained with GFP-Lys. (C) Tumor sections were stained with antibodies against pERK. (D) Tumor sections were stained with cleaved caspase 3. (E) Blood vessel lumen area was also measured in tumor sections.

DETAILED DESCRIPTION 1.0. Definitions

Figure 1A:
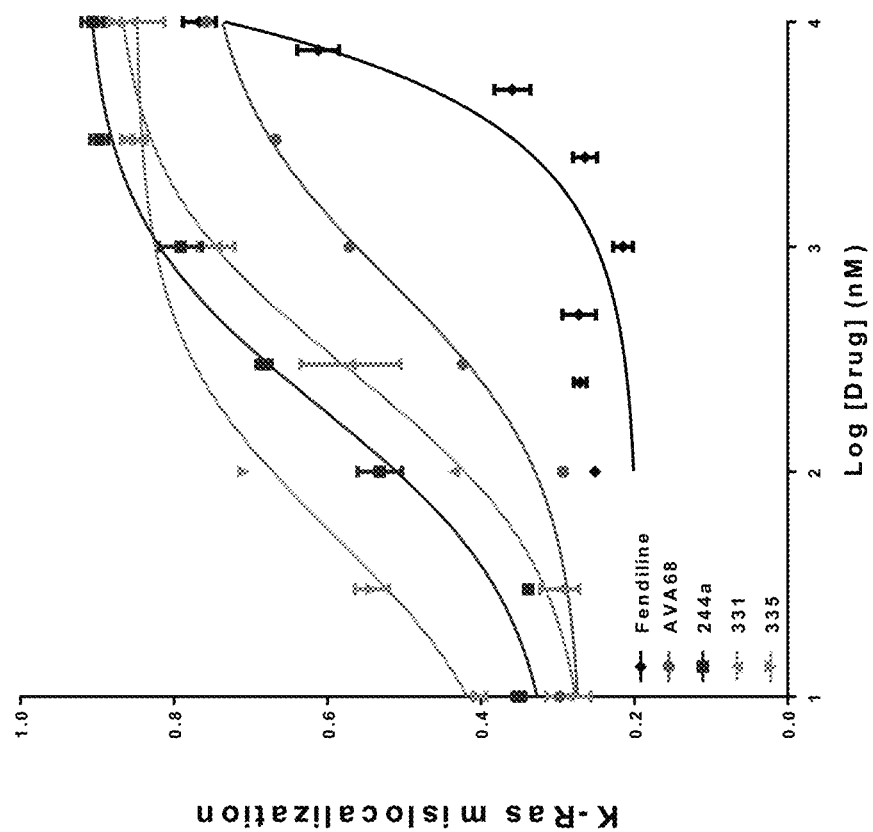
FIG. 1. Comparison of K-RAS and phosphatidylserine mislocalization induced by batch 1/2 compounds. KRASG12V (A) and LactC2 (B) mislocalization induced by the most potent compounds (NY0244, NY0331, NY0335) from batches 1 and 2 was quantified using Manders coefficients as the fraction of mCherry-CAAX colocalizing with mGFP-KRASG12V or mGFP-LactC2. AVA68, a previously identified derivative of fendiline was used as a control. MDCK cells co-expressing GFP—K-RASG12V or mGFP-LactC2 and mCherry-CAAX were grown on coverslips, treated with 0.1% vehicle (DMSO) or various concentrations of drugs (batch 1) for 48 h, and fixed with 4% paraformaldehyde. The coverslips were mounted in mowiol and imaged by confocal microscopy (Nikon A1) using a 60× objective. Using ImageJ software v1.42q, images were converted to 8-bit, and a threshold to a control pixel of each image was set. As a measure of K-Ras or phosphatidylserine mislocalization, the fraction of mCherry-CAAX co-localizing with mGFP-K-RASG12V or mGFP-LactC2, respectively, was calculated using a Manders coefficient plugin downloaded from Wright Cell Image Facility. Dose-response curves (three parameter fitting) were plotted using GraphPad Prism.
Figure 1B:
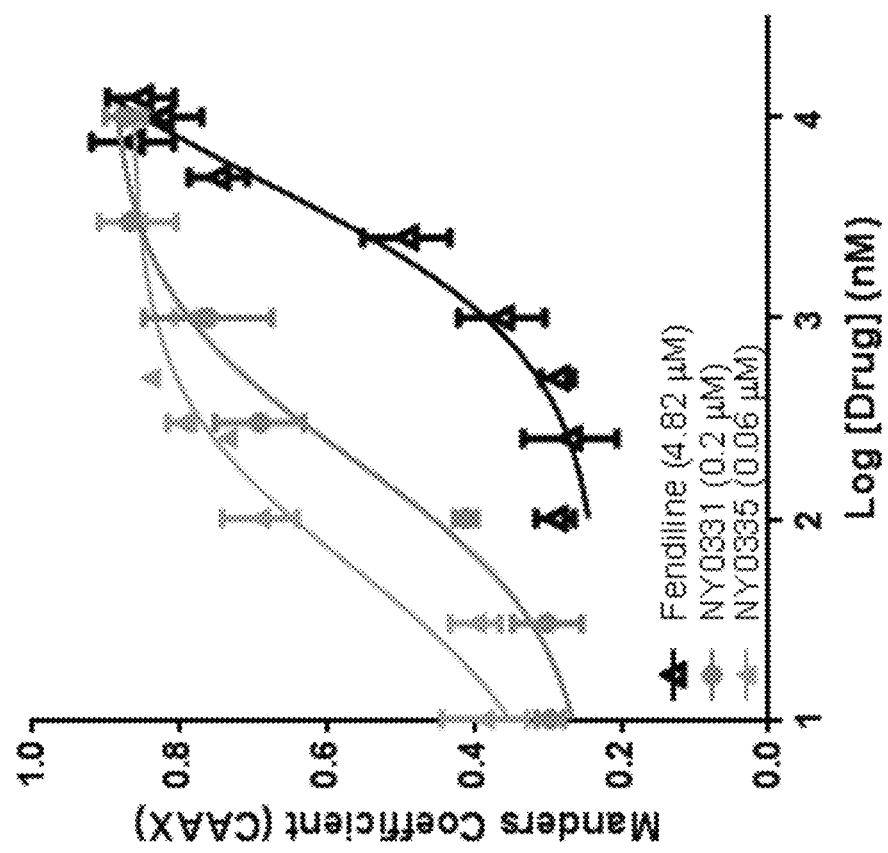
Figure 2:
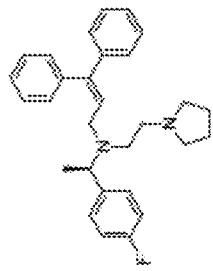
FIG. 2. Summary of most potent fendiline derivatives identified. (A) Potency (IC50) and Efficacy (Emax) of the most potent fendiline-derivatives identified in K-RAS mislocalization assay. (B) Structures of fendiline and the most potent fendiline derivatives identified.
Figure 2:
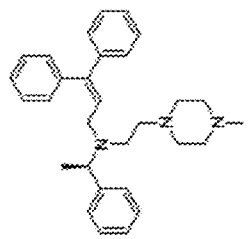
Figure 2:
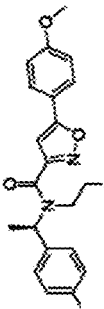
Figure 2:
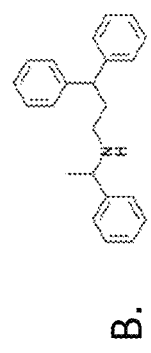
Figure 2:
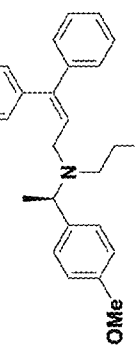
Figure 2:
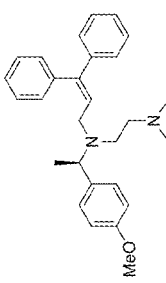
Figure 2:
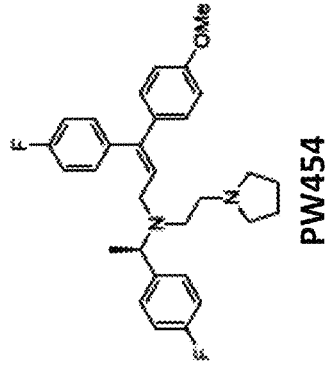
Figure 2:
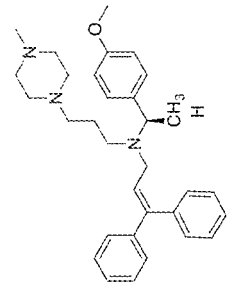
Figure 4:
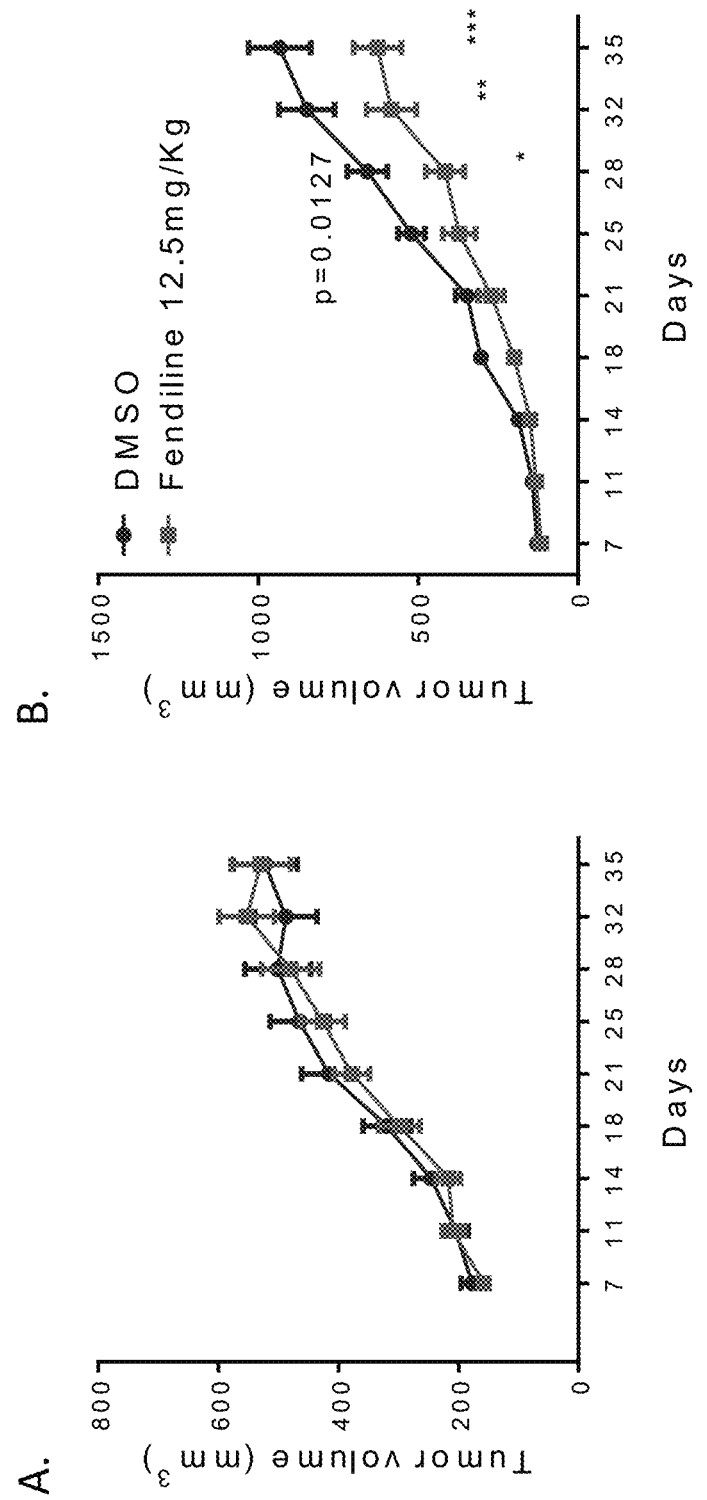
FIG. 4. Inhibition of tumor growth in vivo by fendiline. Nu/nu mice implanted with BxPC-3 or MIAPaCa-2 tumors were treated with vehicle (DMSO) or fendiline (12.5 mg/kg) intraperitoneally and tumor sizes were measured with an external caliper every 3-4 days. Time and fendiline treatment affected MiaPaCa2 xenograft growth (2-way ANOVA, p=0.027). Post-test analysis, using the Bonferroni correction for multiple comparisons, showed that xenografts treated with fendiline were significantly smaller on days 28, 32, and 35 (*p<0.05, <0.01, *<0.001). No significant effects due to drug treatment was observed in BxPC3.
Figure 5A:
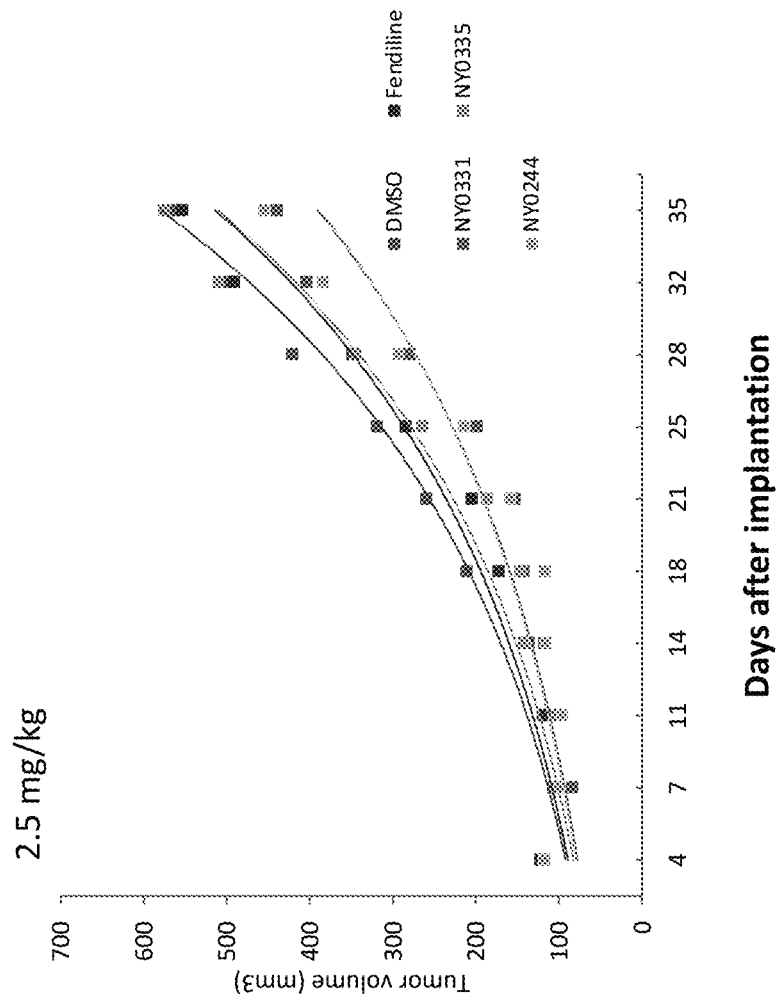
FIG. 5A-C. Inhibition of tumor growth in vivo by fendiline derivatives. Nu/nu mice implanted with MIAPaCa-2 tumors were treated with vehicle (DMSO) or fendiline derivatives intraperitoneally at doses indicated, and tumor sizes were measured with an external caliper every 3-4 days.
Figure 5B:
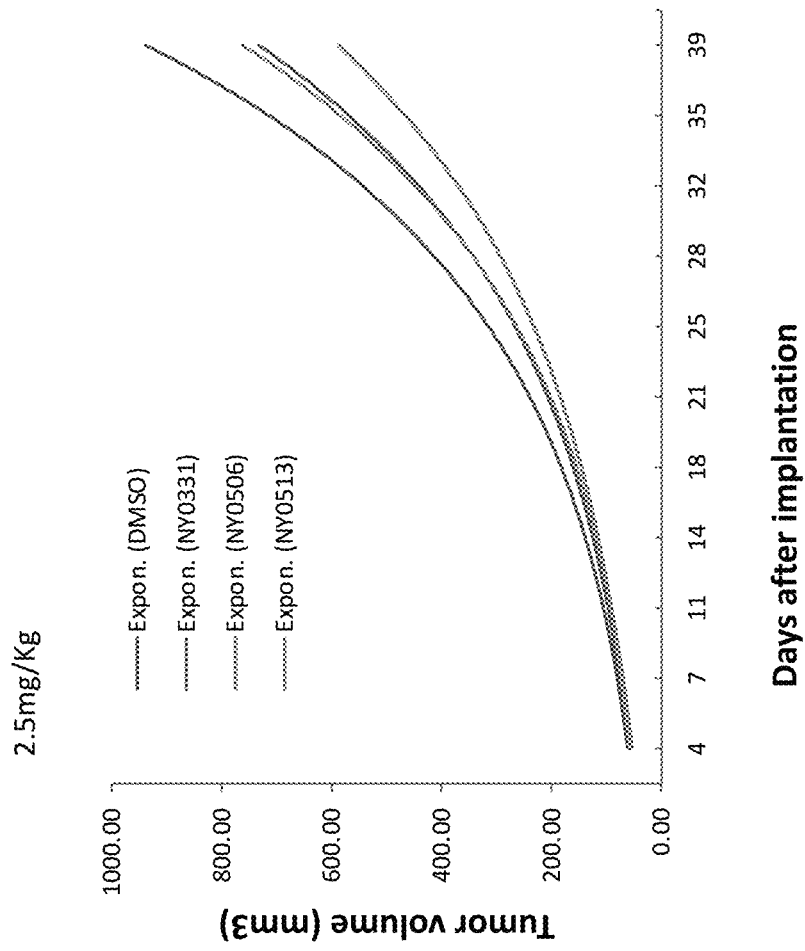
Figure 5C:
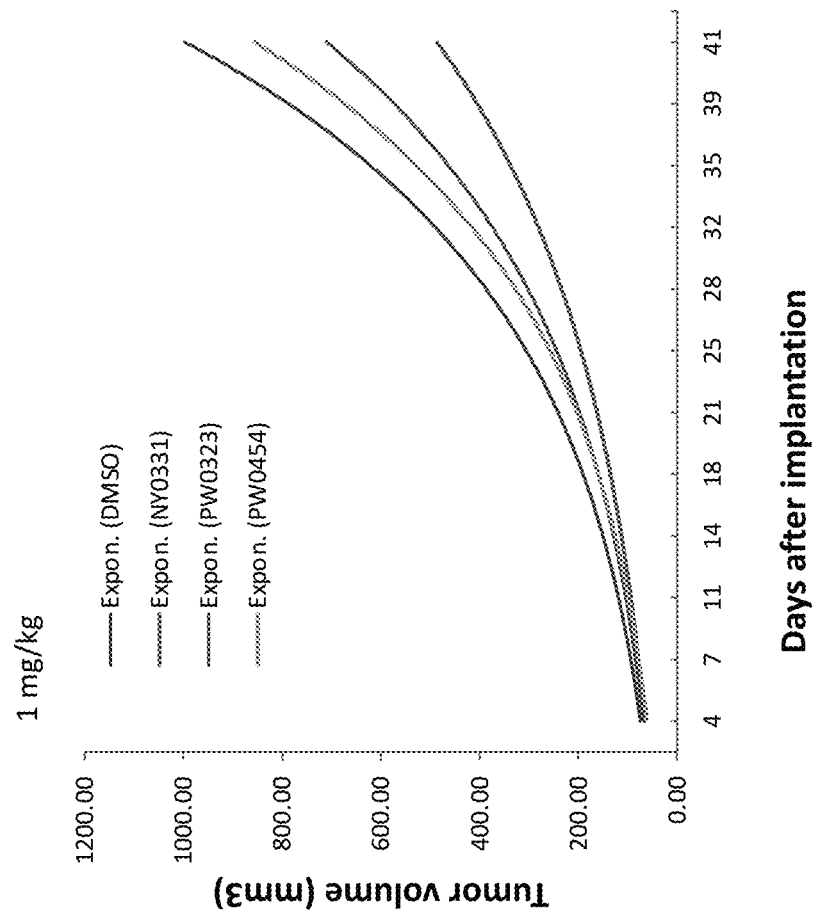

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

The term "pharmaceutically acceptable salt" refers to those salts of the compounds of the present invention which are, within the scope of sound medical judgment, suitable for use in contact with the tissues of patients without undue toxicity, and the like. As used herein, the term "pharmaceutically acceptable salt" may include acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. (See S. M. Barge et al., "Pharmaceutical Salts," J. Pharm. Sci., 66:1-19 (1977), which is incorporated herein by reference in its entirety, for further examples of pharmaceutically acceptable salt).

The term "rt" refers to room temperature.

The term "alkyl" as used herein by itself or as part of another group refers to both straight and branched chain radicals, and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive.

The term "alkylene" as used herein refers to straight and branched chain alkyl linking groups, i.e., an alkyl group that links one group to another group in a molecule. In some embodiments, the term "alkylene" may include —$(CH_2)_n$— where n is 2-8.

The term "aryl" means a polyunsaturated hydrocarbon substituent. Aryl groups can be monocyclic or polycyclic (e.g., 2 to 3 rings that are fused together or linked covalently). Non-limiting examples of aryl and heteroaryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

The term "heteroaryl" as used herein refers to groups having 5 to 14 ring atoms; 6, 10 or 14 7π-electrons shared in a cyclic array; and containing carbon atoms and 1, 2 or 3 oxygen, nitrogen or sulfur heteroatoms. A heteroaryl group can be attached to the remainder of the molecule through a carbon or heteroatom. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, 2-aminopyridine, 4-aminopyridine, 2-aminoimidazoline, and 4-aminoimidazoline.

An "amino" group refers to an —$NH_2$ group.

An "amido" group refers to an —$CONH_2$ group. An alkylamido group refers to an —CONHR group wherein R is as defined above. A dialkylamido group refers to an —CONRR' group wherein R and R' are as defined above.

The term "halogen" or "halo" as used herein by itself or as part of another group refers to chlorine, bromine, fluorine or iodine.

The term "hydroxy" or "hydroxyl" as used herein by itself or as part of another group refers to an —OH group.

An "alkoxy" group refers to an —O-alkyl group wherein "alkyl" is as defined above. In one embodiment, the alkyl group has 1-12 carbons. In another embodiment, the alkyl group has 1-7 carbons. In a further embodiment, the alkyl group has 1-6 carbons. In another embodiment, the alkyl group has 1-4 carbons.

A "thio" group refers to an —SH group.

An "alkylthio" group refers to an —SR group wherein R is alkyl as defined above.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring.

Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

The term "arylamine" or "arylamino" as used herein by itself or as part of another group refers to an amino group which is substituted with an aryl group, as defined above.

As used herein, the term "arylalkyl" denotes an alkyl group substituted with an aryl group, for example, Ph-CH$_2$— etc.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl (—C(O)NR$_2$), unsubstituted alkyl, unsubstituted heteroalkyl, alkoxy, alkylthio, alkylamino, (alkyl)$_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, C$_{1-4}$alkyl, phenyl, benzyl, —NH$_2$, —NH(C$_{1-4}$alkyl), —N(Cl-4alkyl)$_2$, —NO2, —S(C$_{1-4}$alkyl), —SO$_2$(C$_{1-4}$alkyl), —CO$_2$(C$_{1-4}$alkyl), and —O(C$_{1-4}$alkyl).

The term "subject" as used herein refers to an animal, preferably a mammal, most preferably a human, who has been the object of treatment, observation or experiment. Preferably, the subject has experienced and/or exhibited at least one symptom of the disease or disorder to be treated and/or prevented. Further, a subject may not have exhibited any symptoms of the disorder, disease or condition to be treated and/prevented, but has been deemed by a physician, clinician or other medical professional to be at risk for developing said disorder, disease or condition.

The terms "treating," "treatment" and the like as used herein includes the management and care of a subject (preferably a mammal, more preferably a human) for the purpose of combating a disease, condition, or disorder and includes the administration of a compound of the present disclosure to prevent the onset of the symptoms or complications, alleviate the symptoms or complications, or eliminate the disease, condition, or disorder.

ABBREVIATIONS

RAS refers to Rat sarcoma
HRAS refers to Harvey RAS
NRAS refers to Neuroblastoma RAS
KRAS refers to Kirsten RAS
SOS refers to son of sevenless
PM refers to plasma membrane
FTase refers to farnesyltransferase
RCE1 refers to Ras-converting enzyme 1
ICMT1 refers to isoprenylcysteine carboxylmethyltransferase 1
PDEδ refers to phosphodiesterase δ
RE refers to recycling endosome
PMLIs refers to PM location inhibitors
PtdSer refers to phosphatidylserine
ASM refers to acid sphingomyelinase
PK refers to pharmacokinetics
SAR refers to structure-activity relationship
SM refers to sphingomyelin
Cer refers to ceramide
WT refers to wild-type
CC3 refers to cleaved caspase 3
MDCK refers to Madin-Darby Canine Kidney epithelial
pERK refers to phosphorylated protein kinase RNA-like ER kinase
GFP refers to green fluorescent protein
GFP-Lys refers to lysenin tagged with GFP
THF refers to tetrahydrofuran
DCE refers to 1,2-dichloroethane
DIPEA refers to N,N-diisopropylethylamine
EDCI refers to 1-(3-dimethylaminopropyl)-3-ethylcarbodiimide hydrochloride
HOBt refers to 1-hydroxybenzotriazole
TLC refers to thin layer chromatography
UV refers to ultraviolet
TMS refers to tetramethylsilane
HRMS refers to high-resolution mass spectrometry
HPLC refers to high-performance liquid chromatography
LactC2 refers to lactadherin-C2 domain It is to be understood that both the foregoing descriptions are exemplary, and thus do not restrict the scope of the invention.

2.0. Compounds

The present invention pertains to compounds of the Formula I and pharmaceutically acceptable salts thereof, wherein:

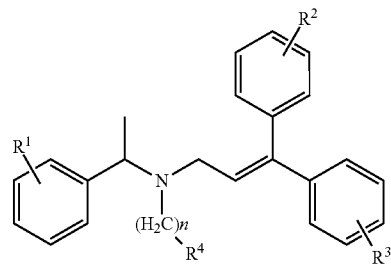

Formula I wherein:
R$^1$ is independently chosen from H, alkyl, alkoxy, X, cyano, amino, nitro, hydroxyl, CX$_3$ and —OCX$_3$ wherein X is F, Cl, Br, or I;
R$^2$ is H, alkyl, alkoxy, X, cyano, amino, nitro, hydroxyl and CX$_3$;
R$^3$ is independently chosen from H, alkyl, alkoxy, X, cyan, amino, nitro, hydroxyl and CX$_3$
R$^4$ is independently chosen from a 5-membered heterocycle and a 6-membered heterocycle; and n is 1-6.

In some embodiments, Formula I encompasses compounds of Formula Ia and pharmaceutically acceptable salts thereof:

Formula Ia

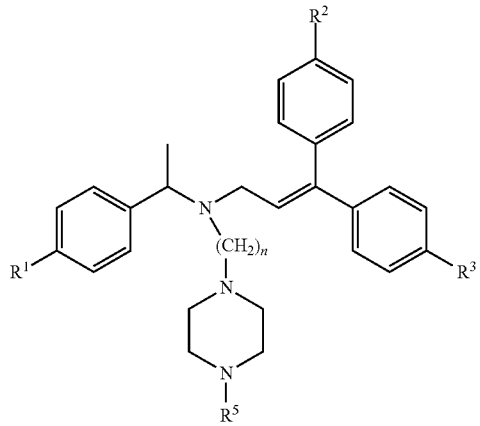

wherein $R^5$ is independently chosen from H and alkyl.

In some further embodiments, Formula I encompasses compounds of Formula Ib and pharmaceutically acceptable salts thereof, wherein:

Formula Ib

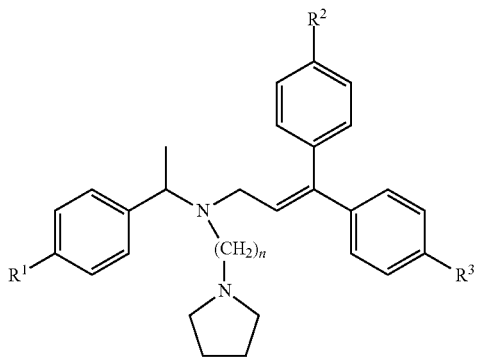

$R^1$ is independently chosen from H, alkyl, alkoxy, X, cyano, amino, nitro, hydroxyl, $CX_3$ and $-OCX_3$ wherein X is F, Cl, Br, or I;

$R^2$ is H, alkyl, alkoxy, X, cyano, amino, nitro, hydroxyl and $CX_3$;

$R^3$ is independently chosen from H, alkyl, alkoxy, X, cyan, amino, nitro, hydroxyl and $CX_3$; and n is 1-6.

In some embodiments, Formula I encompasses the following compounds and pharmaceutically acceptable salts thereof:

| Name | Structure |
|---|---|
| (R)-N-(1-(4-methoxyphenyl)ethyl)-N-(2-(4-methylpiperazin-1-yl)ethyl)-3,3-diphenylprop-2-en-1-amine (NY0244) | 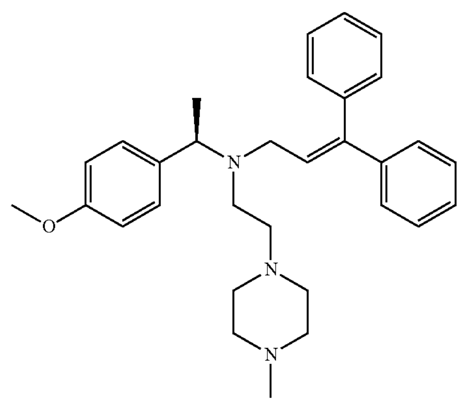 [SMILES: COc1ccc([C@@H](C)N(CC=C(c2ccccc2)c2ccccc2)CCN2CCN(C)CC2)cc1] |
| (R)-N-(1-(4-methoxyphenyl)ethyl)-3,3-diphenyl-N-(2-(pyrrolidin-1-yl)ethyl)prop-2-en-1-amine (NY0331) | 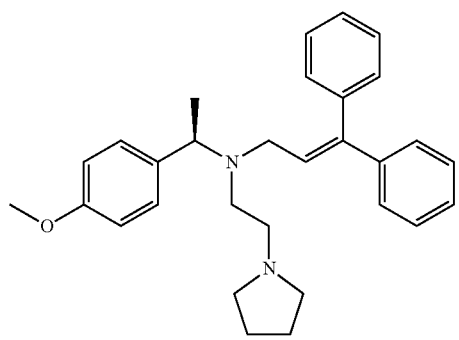 [SMILES: COc1ccc([C@@H](C)N(CC=C(c2ccccc2)c2ccccc2)CCN2CCCC2)cc1] |

| Name | Structure |
|---|---|
| (R)-N-(1-(4-methoxyphenyl)ethyl)-N-(3-(4-methylpiperazin-1-yl)propyl)-3,3-diphenylprop-2-en-1-amine (NY0335) | 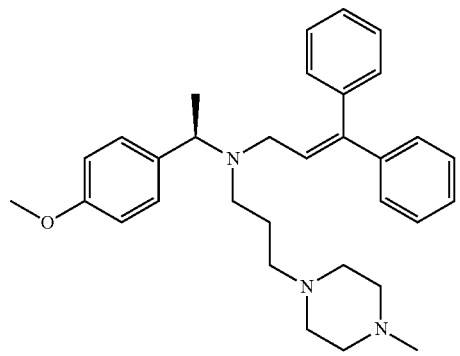 [SMILES: COc1ccc([C@@H](C)N(CC=C(c2ccccc2)c2ccccc2)CCCN2CCN(C)CC2)cc1] |
| (R)-N-(1-(4-fluorophenyl)ethyl)-3,3-diphenyl-N-(2-(pyrrolidin-1-yl)ethyl)prop-2-en-1-amine (NY0506) | 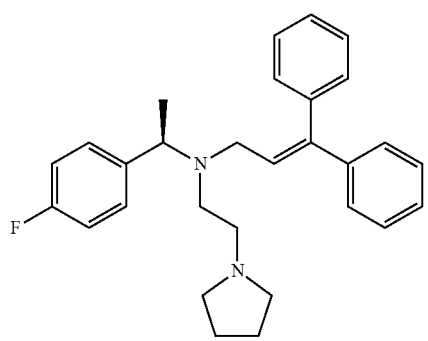 |
| (R)-N-(2-(4-methylpiperazin-1-yl)ethyl)-3,3-diphenyl-N-(1-phenylethyl)prop-2-en-1-amine (NY0513) | 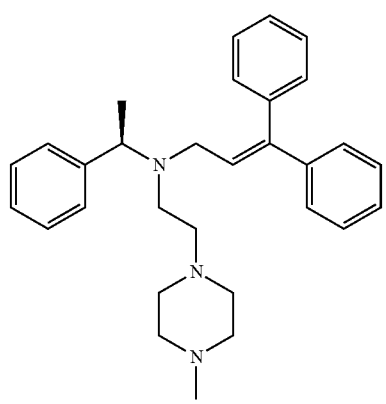 [SMILES: C[C@H](c1ccccc1)N(CC=C(c1ccccc1)c1ccccc1)CCN1CCN(C)CC1] |
| (R,E)-3-(4-fluorophenyl)-N-(1-(4-fluorophenyl)ethyl)-3-(4-methoxyphenyl)-N-(2-(pyrrolidin-1-yl)ethyl)prop-2-en-1-amine (PW0454) | 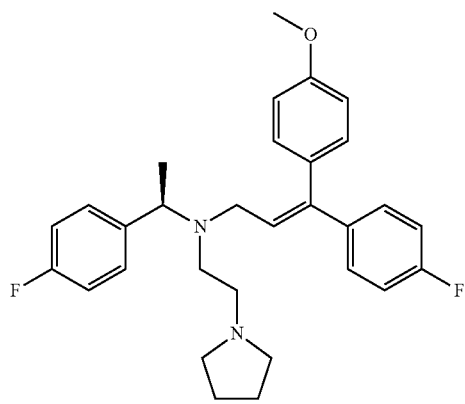 [SMILES: COc1ccc(/C(=C\CN(CCN2CCCC2)[C@H](C)c2ccc(F)cc2)c2ccc(F)cc2)cc1] |

The present invention also pertains to compounds of the Formula II and pharmaceutically acceptable salts thereof, wherein:

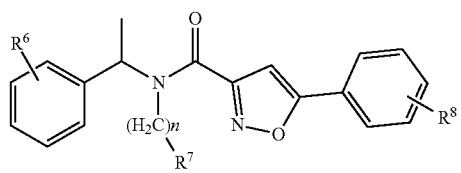

Formula II $R^6$ is independently chosen from H, alkyl, alkoxy, X, cyano, amino, hydroxyl and $CX_3$ and —$OCX_3$, wherein X is F, Cl, Br, or I;

$R^7$ is independently chosen from a 5-membered heterocycle and a 6-membered heterocycle;

$R^8$ is H, alkyl, alkoxy, X, cyano, amino, hydroxyl and $CX_3$; and n is 1-6.

In some embodiments, Formula II encompasses the compounds of Formula IIa and pharmaceutically acceptable salts thereof:

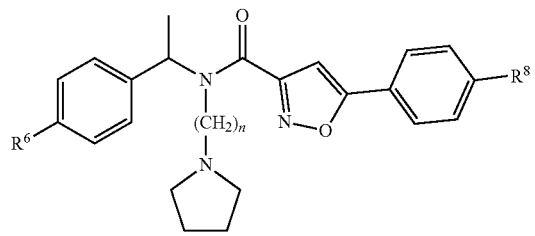

Formula IIa $R^6$ is independently chosen from H, alkyl, alkoxy, X, cyano, amino, hydroxyl and $CX_3$ and —$OCX_3$, wherein X is F, Cl, Br, or I;

$R^8$ is H, alkyl, alkoxy, X, cyano, amino, hydroxyl and $CX_3$; and n is 1-6.

| Compound Label | Structure |
|---|---|
| (R)-N-allyl-N-(1-(4-methoxyphenyl)ethyl)-3,3-diphenylprop-2-en-1-amine (NY0217) | 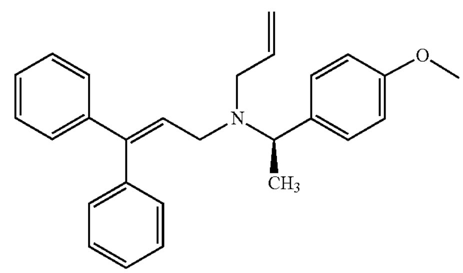 |
| (R)-N-(1-(4-methoxyphenyl)ethyl)-N-methyl-3,3-diphenylprop-2-en-1-amine (NY0218) | 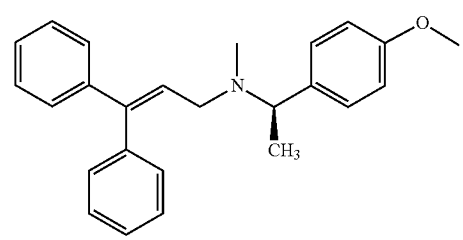 |
| N-(3,3-diphenylallyl)-N-(4-methoxyphenethyl)-3,3-diphenylprop-2-en-1-amine (NY0220) | 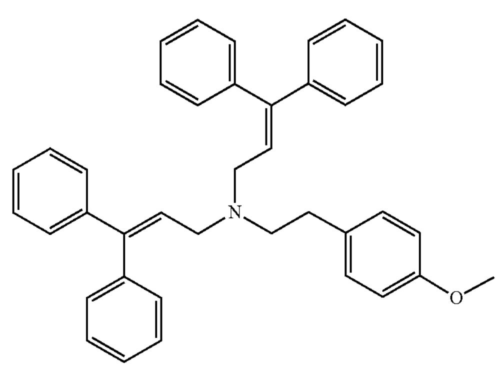 [SMILES: COc1ccc(CCN(CC=C(c2ccccc2)c2ccccc2)CC=C(c2ccccc2)c2ccccc2)cc1] |

-continued

| Compound Label | Structure |
|---|---|
| 2-(3,3-diphenylallyl)-1,2,3,4-tetrahydroisoquinoline (NY0221) | 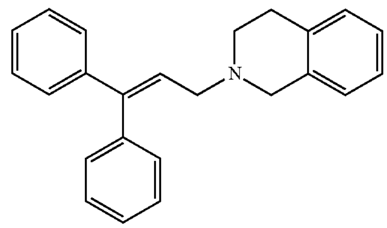 [SMILES: C(CN1CCc2ccccc2C1)=C(c1ccccc1)c1ccccc1] |
| (R)-N-(3,3-diphenylallyl)-N-(1-(4-methoxyphenyl)ethyl)acetamide (NY0222) | 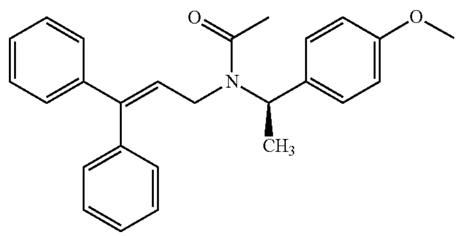 [SMILES: COc1ccc([C@@H](C)N(CC=C(c2ccccc2)c2ccccc2)C(C)=O)cc1] |
| (R)-N-(3,3-diphenylallyl)-N-(1-(4-methoxyphenyl)ethyl)methanesulfonamide (NY0223) | 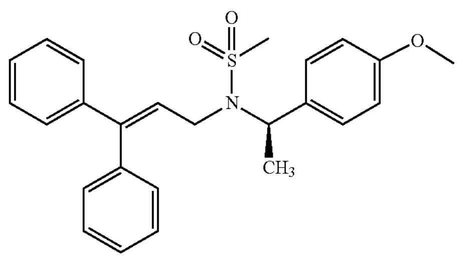 [SMILES: COc1ccc([C@@H](C)N(CC=C(c2ccccc2)c2ccccc2)S(C)(=O)=O)cc1] |
| (R)-1-(3,3-diphenylallyl)-3-(4-methoxyphenyl)-1-(1-(4-methoxyphenyl)ethyl)urea (NY0224) | 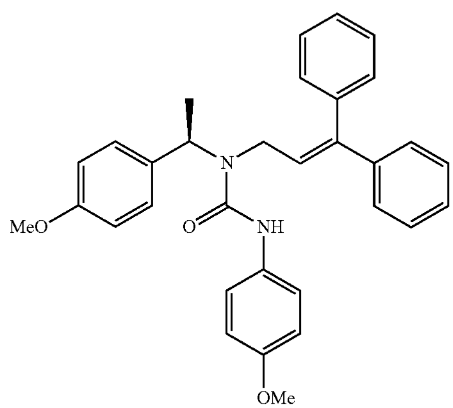 [SMILES: COc1ccc(NC(=O)N(CC=C(c2ccccc2)c2ccccc2)[C@H](C)c2ccc(OC)cc2)cc1] |
| (R)-phenyl (3,3-diphenylallyl)(1-(4-methoxyphenyl)ethyl)carbamate (NY0225) | 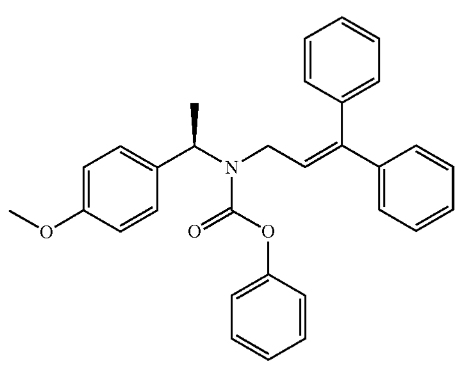 [SMILES: COc1ccc([C@@H](C)N(CC=C(c2ccccc2)c2ccccc2)C(=O)Oc2ccccc2)cc1] |

| Compound Label | Structure |
|---|---|
| (1R,2S)-N,N-bis(3,3-diphenylallyl)-2-phenylcyclopropanamine (NY022601) | 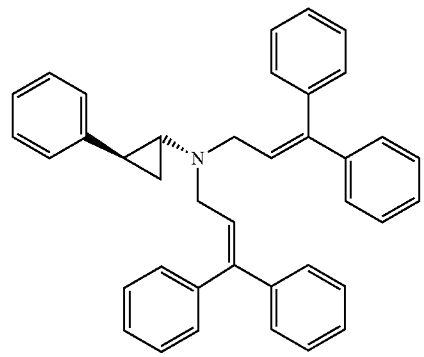 |
| (1R,2S)-N-(3,3-diphenylallyl)-2-phenylcyclopropanamine (NY022602) | 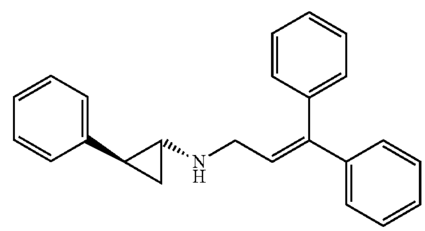 |
| (R)-N-(3,3-diphenylallyl)-3,3-diphenyl-N-(2-phenylpropyl)prop-2-en-1-amine (NY022701) | 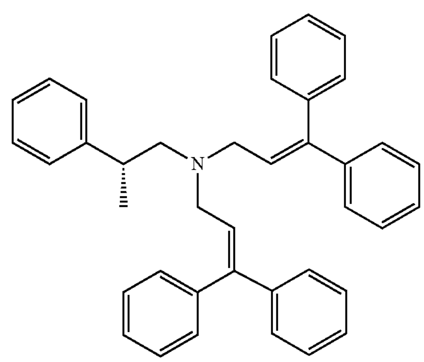 [SMILES: C[C@@H](CN(CC=C(c1ccccc1)c1ccccc1)CC=C(c1ccccc1)c1ccccc1)c1ccccc1] |
| (R)-3,3-diphenyl-N-(2-phenylpropyl)prop-2-en-1-amine (NY022702) | 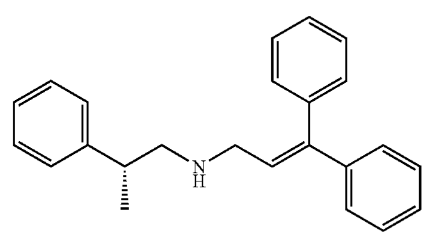 [SMILES: C[C@@H](CNCC=C(c1ccccc1)c1ccccc1)c1ccccc1] |
| (R)-methyl 2-((3,3-diphenylallyl)(1-(4-methoxyphenyl)ethyl)amino)acetate (NY0228) | 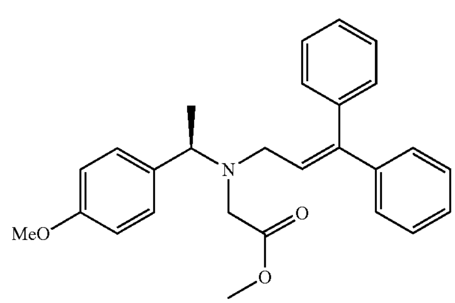 [SMILES: COC(=O)CN(CC=C(c1ccccc1)c1ccccc1)[C@H](C)c1ccc(OC)cc1] |

| Compound Label | Structure |
| --- | --- |
| (R)-2-((3,3-diphenylallyl)(1-(4-methoxyphenyl)ethyl)amino)acetic acid (NY0229) | 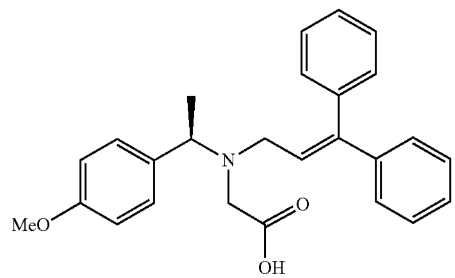 [SMILES: COc1ccc([C@@H](C)N(CC=C(c2ccccc2)c2ccccc2)CC(=O)O)cc1] |
| (R)-2-((3,3-diphenylallyl)(1-(4-methoxyphenyl)ethyl)amino)-1-(4-methylpiperazin-1-yl)ethanone (NY0232) | 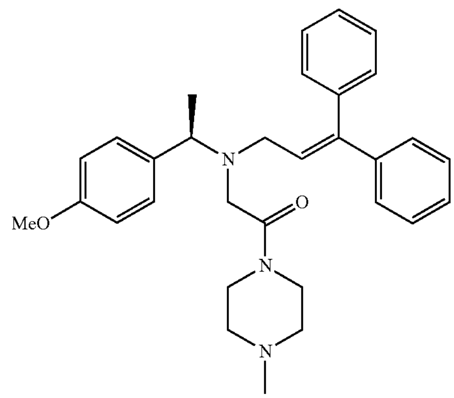 [SMILES: COc1ccc([C@@H](C)N(CC=C(c2ccccc2)c2ccccc2)CC(=O)N2CCN(C)CC2)cc1] |
| (R)-1-(3,4-dihydroisoquinolin-2(1H)-yl)-2-((3,3-diphenylallyl)(1-(4-methoxyphenyl)ethyl)amino)ethanone (NY0233) | 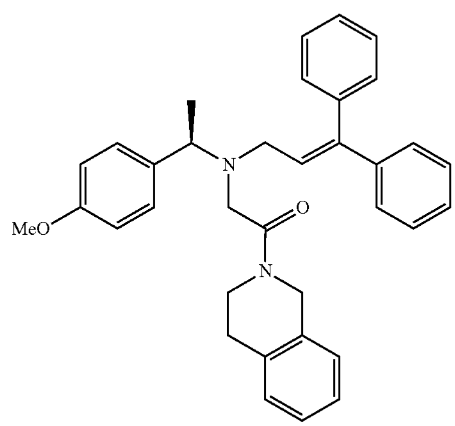 [SMILES: COc1ccc([C@@H](C)N(CC=C(c2ccccc2)c2ccccc2)CC(=O)N2CCc3ccccc3C2)cc1] |
| (R)-N-(1-(4-methoxyphenyl)ethyl)-3,3-diphenyl-N-(prop-2-yn-1-yl)prop-2-en-1-amine (NY0234) | 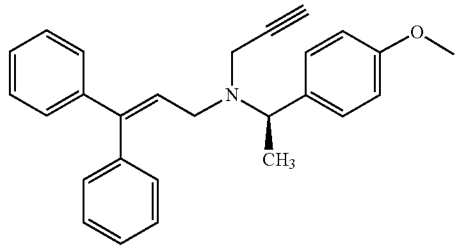 [SMILES: C#CCN(CC=C(c1ccccc1)c1ccccc1)[C@H](C)c1ccc(OC)cc1] |

-continued
| Compound Label | Structure |
|---|---|
| (R)-N-(3,3-diphenylallyl)-N-(1-(4-methoxyphenyl)ethyl)acrylamide (NY0235) | 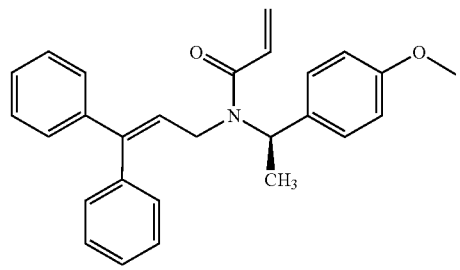 [SMILES: C=CC(=O)N(CC=C(c1ccccc1)c1ccccc1)[C@H](C)c1ccc(OC)cc1] |
| 1-(3,3-diphenylallyl)-1,2,3,4-tetrahydroquinoline (NY0237) | 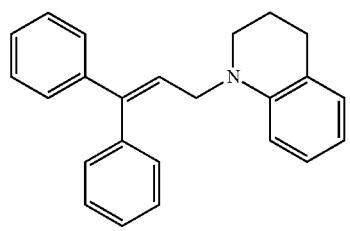 [SMILES: C(CN1CCCc2ccccc21)=C(c1ccccc1)c1ccccc1] |
| (R)-2-((3,3-diphenylallyl)(1-(4-methoxyphenyl)ethyl)amino)ethanol (NY0241) | 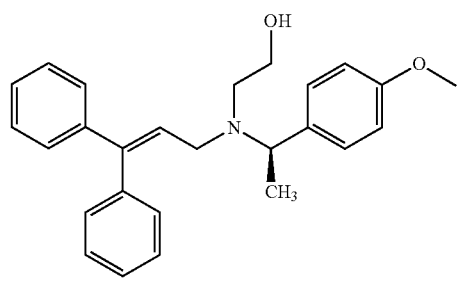 [SMILES: COc1ccc([C@@H](C)N(CC=C(c2ccccc2)c2ccccc2)CCO)cc1] |
| (R)-N-(1-(4-methoxyphenyl)ethyl)-N-(2-(4-methylpiperazin-1-yl)ethyl)-3,3-diphenylprop-2-en-1-amine (NY0244) | 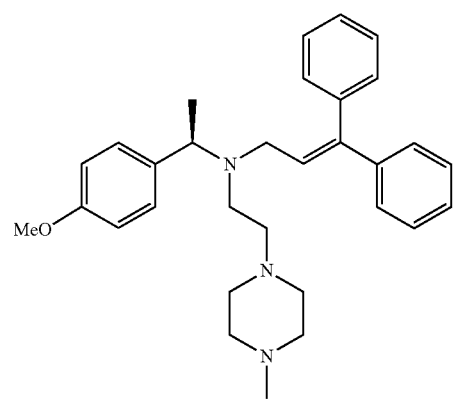 [SMILES: COc1ccc([C@@H](C)N(CC=C(c2ccccc2)c2ccccc2)CCN2CCN(C)CC2)cc1] |
| 1-(3,3-diphenylallyl)-6-fluoro-1,2,3,4-tetrahydroquinoline (NY0293) | 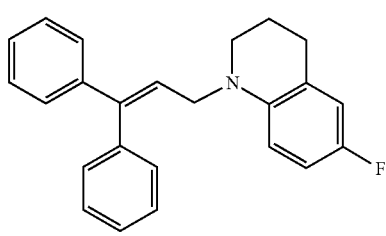 [SMILES: Fc1ccc2c(c1)CCCN2CC=C(c1ccccc1)c1ccccc1] |

-continued
| Compound Label | Structure |
|---|---|
| 1-(3,3-diphenylallyl)-2-methyl-1,2,3,4-tetrahydroquinoline (NY0304) | 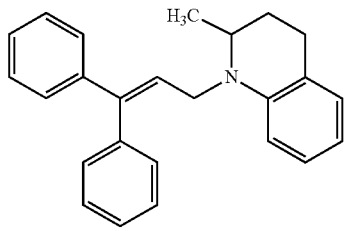 [SMILES: CC1CCc2ccccc2N1CC=C(c1ccccc1)c1ccccc1] |
| 1-(3,3-diphenylallyl)-4-phenylpiperidine (NY0306) | 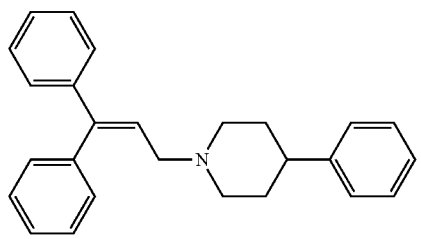 |
| 1-(3,3-diphenylallyl)-4-phenylpiperazine (NY0307) | 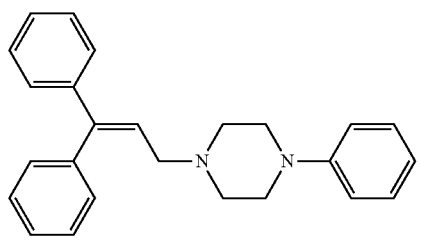 [SMILES: C(CN1CCC(c2ccccc2)CC1)=C(c1ccccc1)c1ccccc1] |
| N-(3,3-diphenylallyl)-2-fluoro-N-((R)-1-(4-methoxyphenyl)ethyl)propanamide (NY0314) | 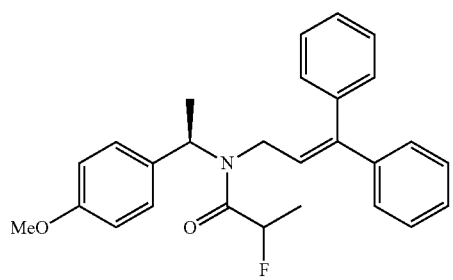 [SMILES: COc1ccc([C@@H](C)N(CC=C(c2ccccc2)c2ccccc2)C(=O)C(C)F)cc1] |
| (R)-N-(2-fluoroethyl)-N-(1-(4-methoxyphenyl)ethyl)-3,3-diphenylprop-2-en-1-amine (NY0315) | 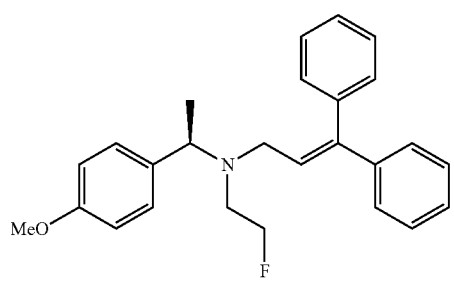 [SMILES: COc1ccc([C@@H](C)N(CC=C(c2ccccc2)c2ccccc2)CCF)cc1] |

| Compound Label | Structure |
|---|---|
| (R)-N-(1-(4-methoxyphenyl)ethyl)-N-(2-morpholinoethyl)-3,3-diphenylprop-2-en-1-amine (NY0316) | 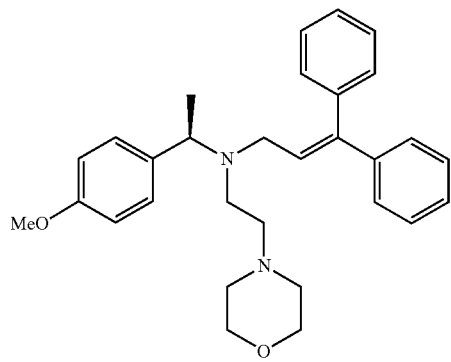 |
| (R)-4-(2-((3,3-diphenylallyl)(1-(4-methoxyphenyl)ethyl)amino)ethyl)piperazin-2-one (NY0325) | 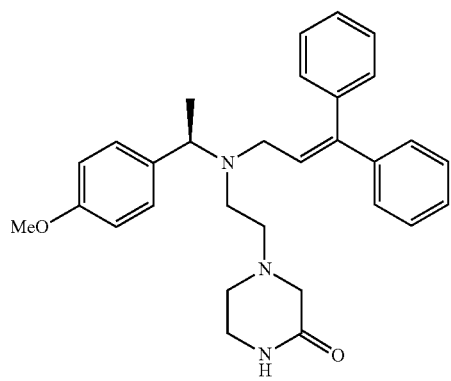 [SMILES: COc1ccc([C@@H](C)N(CC=C(c2ccccc2)c2ccccc2)CCN2CCNC(=O)C2)cc1] |
| (R)-N-(1-(4-methoxyphenyl)ethyl)-3,3-diphenyl-N-(2-(piperidin-1-yl)ethyl)prop-2-en-1-amine (NY0329) | 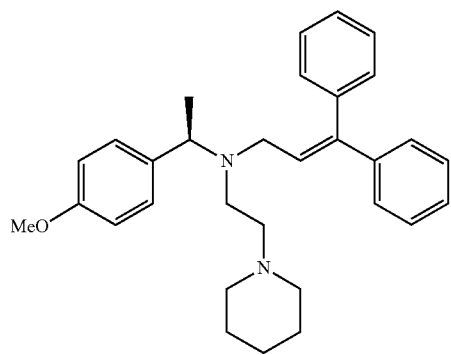 |
| (R)-N-(1-(4-methoxyphenyl)ethyl)-3,3-diphenyl-N-(2-(pyrrolidin-1-yl)ethyl)prop-2-en-1-amine (NY0331) | 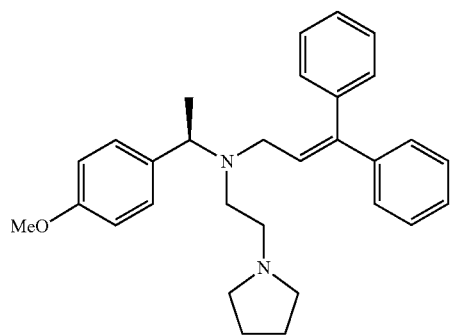 [SMILES: COc1ccc([C@@H](C)N(CC=C(c2ccccc2)c2ccccc2)CCN2CCCC2)cc1] |

-continued

| Compound Label | Structure |
|---|---|
| (R)-N-(1-(4-methoxyphenyl)ethyl)-N-(3-(4-methylpiperazin-1-yl)propyl)-3,3-diphenylprop-2-en-1-amine (NY0335) | 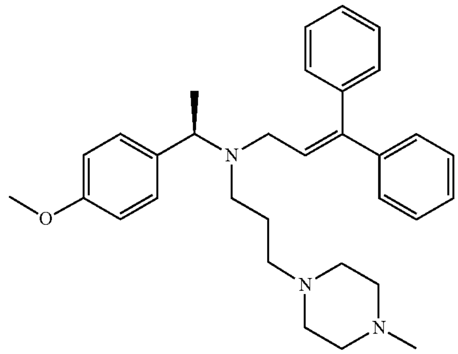 [SMILES: COc1ccc([C@@H](C)N(CC=C(c2ccccc2)c2ccccc2)CCCN2CCN(C)CC2)cc1] |
| (R)-tert-butyl 4-(2-((3,3-diphenylallyl)(1-(4-methoxyphenyl)ethyl)amino)ethyl)piperazine-1-carboxylate (NY0345) | 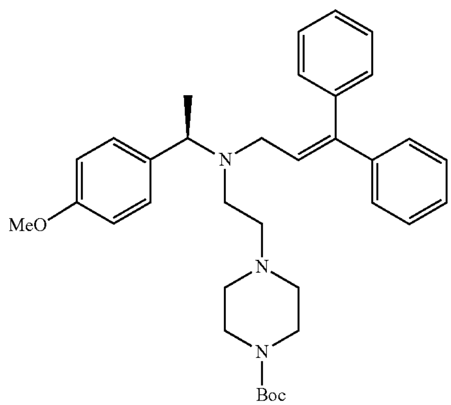 [SMILES: COc1ccc([C@@H](C)N(CC=C(c2ccccc2)c2ccccc2)CCN2CCN(C(=O)OC(C)(C)C)CC2)cc1] |
| (R,E)-N-(1-(4-methoxyphenyl)ethyl)-N-(2-(4-methylpiperazin-1-yl)ethyl)-3-phenylprop-2-en-1-amine (NY0346) | 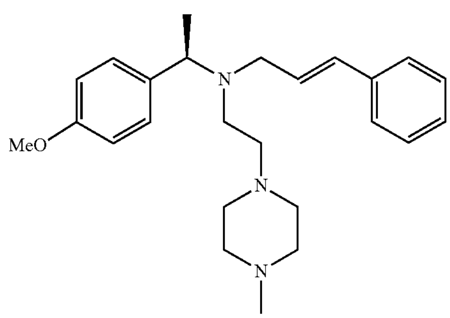 [SMILES: COc1ccc([C@@H](C)N(C/C=C/c2ccccc2)CCN2CCN(C)CC2)cc1] |
| (R)-N-(1-(4-methoxyphenyl)ethyl)-3,3-diphenyl-N-(2-(piperazin-1-yl)ethyl)prop-2-en-1-amine (NY0347) | 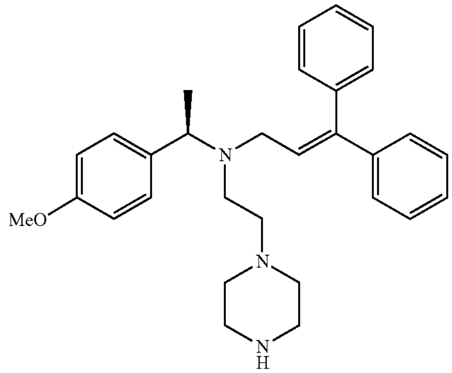 [SMILES: COc1ccc([C@@H](C)N(CC=C(c2ccccc2)c2ccccc2)CCN2CCNCC2)cc1] |

-continued

| Compound Label | Structure |
|---|---|
| (R)-N-(3,3-diphenylallyl)-4,4-diethoxy-N-(1-(4-methoxyphenyl)ethyl)butan-1-amine (NY0348) | 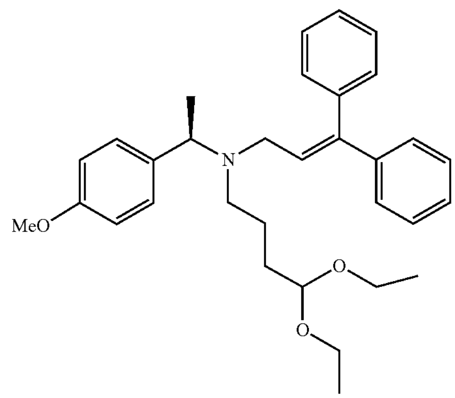 [SMILES: CCOC(CCCN(CC=C(c1ccccc1)c1ccccc1)[C@H](C)c1ccc(OC)cc1)OCC] |
| (R)-N-(1-(4-methoxyphenyl)ethyl)-N-(2-(4-methylpiperazin-1-yl)ethyl)prop-2-en-1-amine (NY0349) | 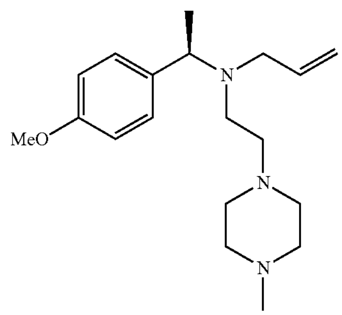 [SMILES: C=CCN(CCN1CCN(C)CC1)[C@H](C)c1ccc(OC)cc1] |
| (R)-1-(4-(2-((3,3-diphenylallyl)(1-(4-methoxyphenyl)ethyl)amino)ethyl)piperazin-1-yl)ethanone (NY0350) | 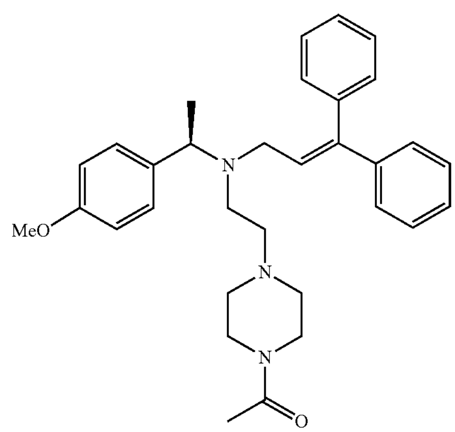 |
| (R)-N-(1-(4-methoxyphenyl)ethyl)-N-(2-(4-(methylsulfonyl)piperazin-1-yl)ethyl)-3,3-diphenylprop-2-en-1-amine (NY0351) | 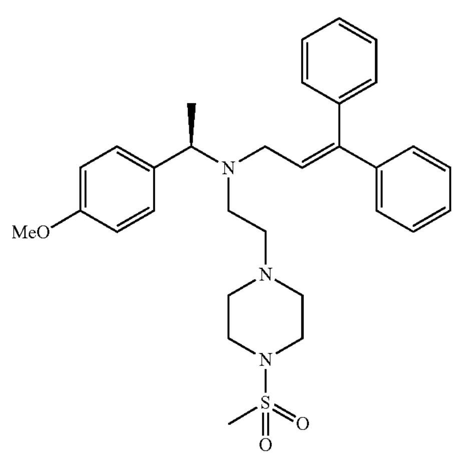 [SMILES: COc1ccc([C@@H](C)N(CC=C(c2ccccc2)c2ccccc2)CCN2CCN(S(C)(=O)=O)CC2)cc1] |

| Compound Label | Structure |
|---|---|
| (R)-4-(2-((3,3-diphenylallyl)(1-(4-methoxyphenyl)ethyl)amino)ethyl)-N-phenylpiperazine-1-carboxamide (NY0352) | 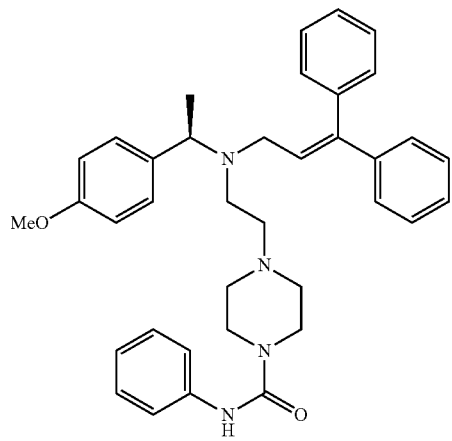 [SMILES: COc1ccc([C@@H](C)N(CC=C(c2ccccc2)c2ccccc2)CCN2CCN(C(=O)Nc3ccccc3)CC2)cc1] |
| (R)-phenyl 4-(2-((3,3-diphenylallyl)(1-(4-methoxyphenyl)ethyl)amino)ethyl)piperazine-1-carboxylate (NY0353) | 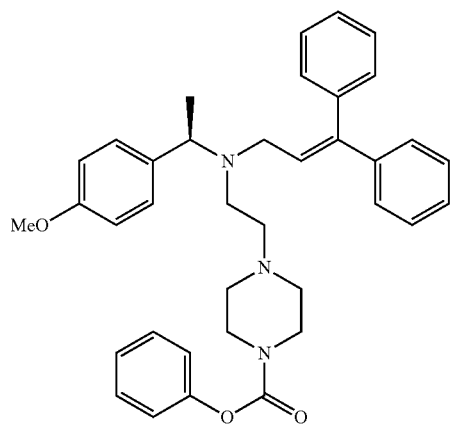 [SMILES: COc1ccc([C@@H](C)N(CC=C(c2ccccc2)c2ccccc2)CCN2CCN(C(=O)Oc3ccccc3)CC2)cc1] |
| (R)-N-(1-(4-methoxyphenyl)ethyl)-3,3-diphenyl-N-(2-(4-(prop-2-ynyl)piperazin-1-yl)ethyl)prop-2-en-1-amine (NY0356) | 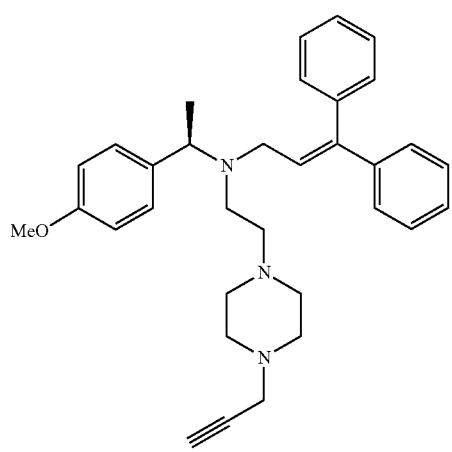 |

| Compound Label | Structure |
|---|---|
| (R)-1-(4-(2-((3,3-diphenylallyl)(1-(4-methoxyphenyl)ethyl)amino)ethyl)piperazin-1-yl)prop-2-en-1-one (NY0357a) | 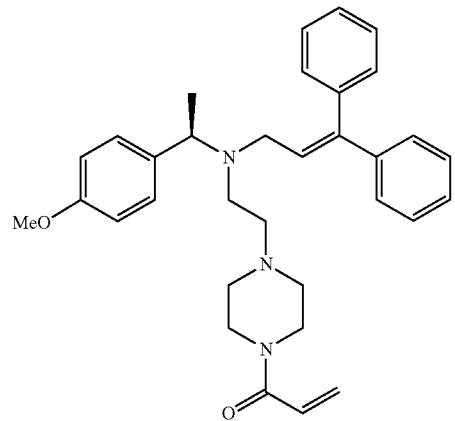 |
| (R)-N$^1$-(3,3-diphenylallyl)-N$^2$,N$^2$-diethyl-N$^1$-(1-(4-methoxyphenyl)ethyl)ethane-1,2-diamine (NY0358) | 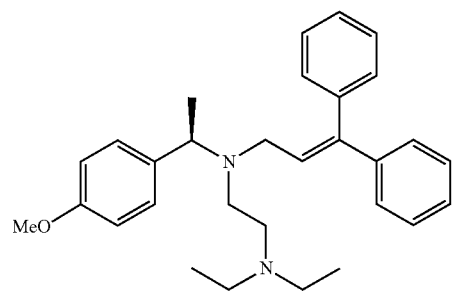 |
| (R)-N-(1-(2-methoxyphenyl)ethyl)-N-(2-(4-methylpiperazin-1-yl)ethyl)-3,3-diphenylprop-2-en-1-amine (NY0366) | 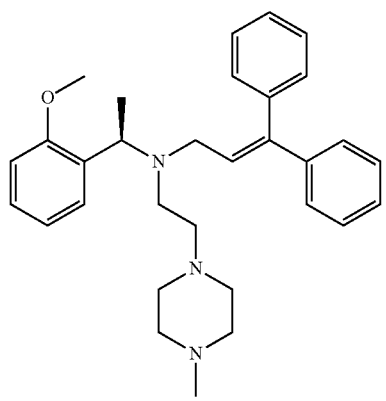 |
| (R)-N-(3,3-diphenylallyl)-N-(2-(4-methylpiperazin-1-yl)ethyl)-2,3-dihydro-1H-inden-1-amine (NY0369b) | 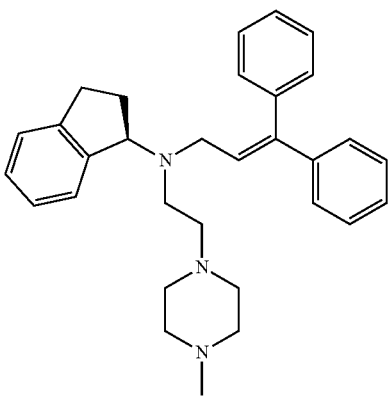 |

| Compound Label | Structure |
|---|---|
| (R)-N-(1-(3-chlorophenyl)ethyl)-N-(2-(4-methylpiperazin-1-yl)ethyl)-3,3-diphenylprop-2-en-1-amine (NY0370b) | 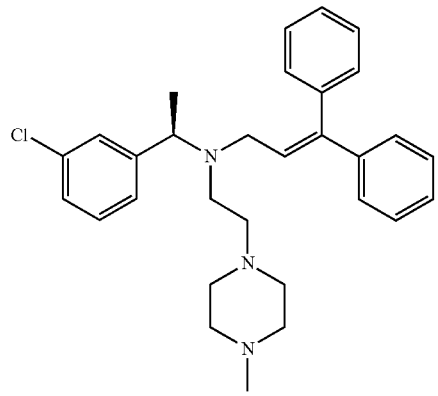 [SMILES: C[C@H](c1cccc(Cl)c1)N(CC=C(c1ccccc1)c1ccccc1)CCN1CCN(C)CC1] |
| (R)-N-(2-(4-isobutylpiperazin-1-yl)ethyl)-N-(1-(4-methoxyphenyl)ethyl)-3,3-diphenylprop-2-en-1-amine (NY0372) | 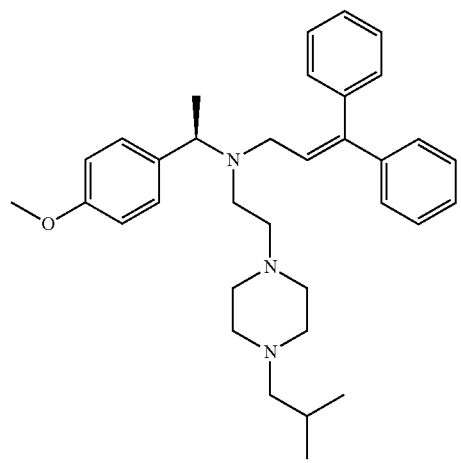 [SMILES: COc1ccc([C@@H](C)N(CC=C(c2ccccc2)c2ccccc2)CCN2CCN(CC(C)C)CC2)cc1] |
| N,N-bis(3,3-diphenylallyl)-1-phenylcyclopropanamine (NY040401) | 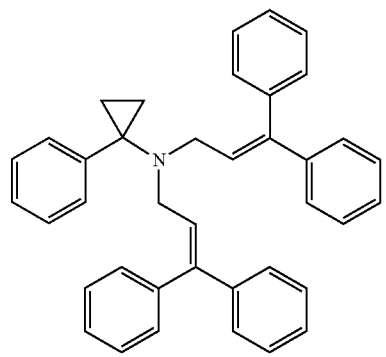 [SMILES: C(CN(CC=C(c1ccccc1)c1ccccc1)C1(c2ccccc2)CC1)=C(c1ccccc1)c1ccccc1] |
| N-(3,3-diphenylallyl)-1-phenylcyclopropanamine (NY040402) | 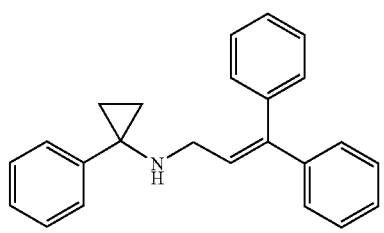 [SMILES: C(CNC1(c2ccccc2)CC1)=C(c1ccccc1)c1ccccc1] |

-continued

| Compound Label | Structure |
|---|---|
| (R)-3-tert-butyl-1-(3,3-diphenylallyl)-1-(1-(4-methoxyphenyl)ethyl)urea (NY0428) | 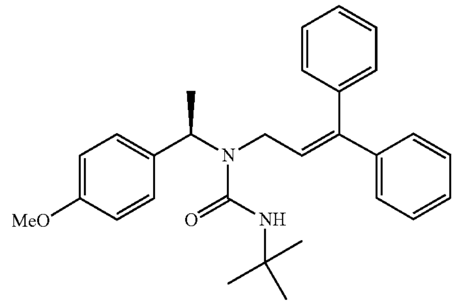 [SMILES: COc1ccc([C@@H](C)N(CC=C(c2ccccc2)c2ccccc2)C(=O)NC(C)(C)C)cc1] |
| (R)-N-ethyl-N-(1-(4-methoxyphenyl)ethyl)-3,3-diphenylprop-2-en-1-amine (NY0429) | 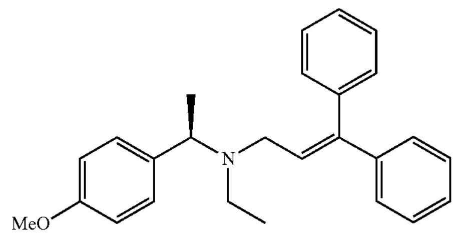 [SMILES: CCN(CC=C(c1ccccc1)c1ccccc1)[C@H](C)c1ccc(OC)cc1] |
| (R)-N$^1$-(3,3-diphenylallyl)-N$^1$-(1-(4-methoxyphenyl)ethyl)-N$^2$,N$^2$-dimethylethane-1,2-diamine (NY0435) | |
| (R)-N-(2-(aziridin-1-yl)ethyl)-N-(1-(4-methoxyphenyl)ethyl)-3,3-diphenylprop-2-en-1-amine (NY0438) | 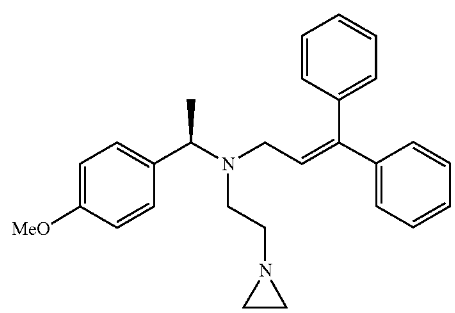 [SMILES: COc1ccc([C@@H](C)N(CC=C(c2ccccc2)c2ccccc2)CCN2CC2)cc1] |
| N-(3,3-diphenylallyl)-N-(2-(4-methylpiperazin-1-yl)ethyl)-1-phenylcyclopropanamine (NY0443) | 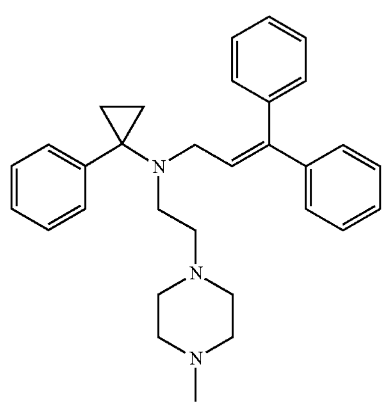 [SMILES: CN1CCN(CCN(CC=C(c2ccccc2)c2ccccc2)C2(c3ccccc3)CC2)CC1] |

| Compound Label | Structure |
|---|---|
| N-(3,3-diphenylallyl)-1-phenyl-N-(2-(pyrrolidin-1-yl)ethyl)cyclopropanamine (NY0444) | 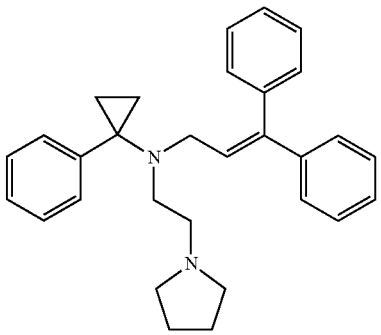 [SMILES: C(CN(CCN1CCCC1)C1(c2ccccc2)CC1)=C(c1ccccc1)c1ccccc1] |
| (R)-4-((3,3-diphenylallyl)(1-(4-methoxyphenyl)ethyl)amino)butanal (NY0445) | 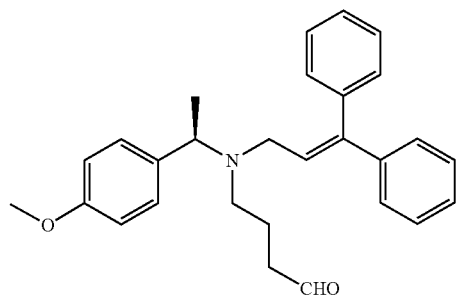 [SMILES: COc1ccc([C@@H](C)N(CC=C(c2ccccc2)c2ccccc2)CCCC=O)cc1] |
| (R)-4-((3,3-diphenylallyl)(1-(4-methoxyphenyl)ethyl)amino)butan-1-ol (NY0448) | 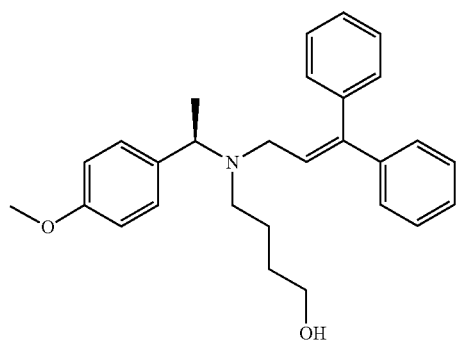 [SMILES: COc1ccc([C@@H](C)N(CC=C(c2ccccc2)c2ccccc2)CCCCO)cc1] |
| (R)-N-(3,3-diphenylallyl)-N-(1-(4-methoxyphenyl)ethyl)-4-(4-methylpiperazin-1-yl)butan-1-amine (NY0449) | 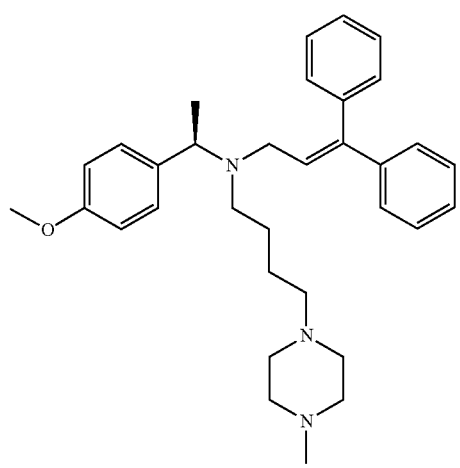 [SMILES: COc1ccc([C@@H](C)N(CC=C(c2ccccc2)c2ccccc2)CCCCN2CCN(C)CC2)cc1] |

-continued
| Compound Label | Structure |
|---|---|
| (R)-N-(1-(3-methoxyphenyl)ethyl)-N-(2-(4-methylpiperazin-1-yl)ethyl)-3,3-diphenylprop-2-en-1-amine (NY0452) | 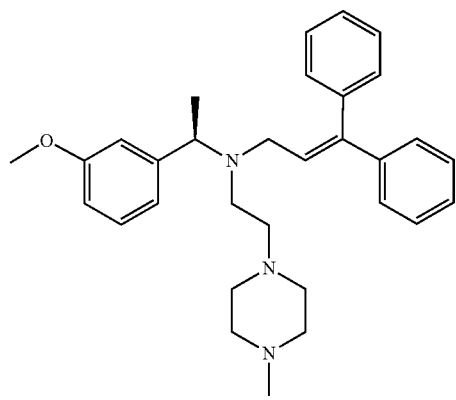 [SMILES: COc1cccc([C@@H](C)N(CC=C(c2ccccc2)c2ccccc2)CCN2CCN(C)CC2)c1] |
| (S)-N-(1-(4-methoxyphenyl)ethyl)-N-(2-(4-methylpiperazin-1-yl)ethyl)-3,3-diphenylprop-2-en-1-amine (NY0454) | 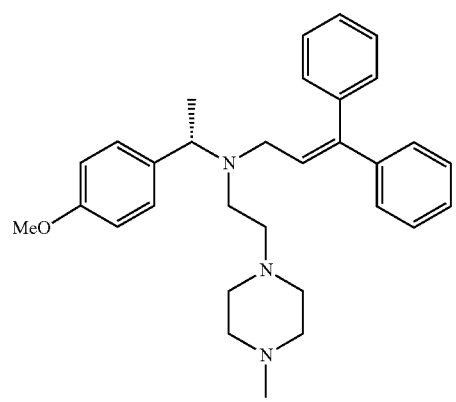 [SMILES: COc1ccc([C@H](C)N(CC=C(c2ccccc2)c2ccccc2)CCN2CCN(C)CC2)cc1] |
| (R)-3-((3,3-diphenylallyl)(1-(4-methoxyphenyl)ethyl)amino)propan-1-ol (NY0479) | 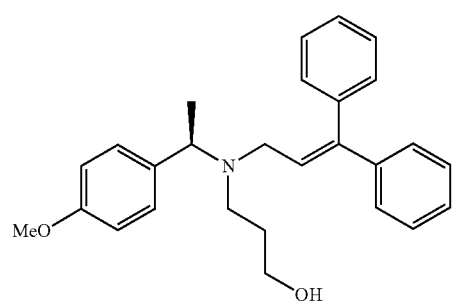 [SMILES: COc1ccc([C@@H](C)N(CC=C(c2ccccc2)c2ccccc2)CCCO)cc1] |
| (R)-N-(1-(4-methoxyphenyl)ethyl)-3,3-diphenyl-N-(3-(pyrrolidin-1-yl)propyl)prop-2-en-1-amine (NY0502) | 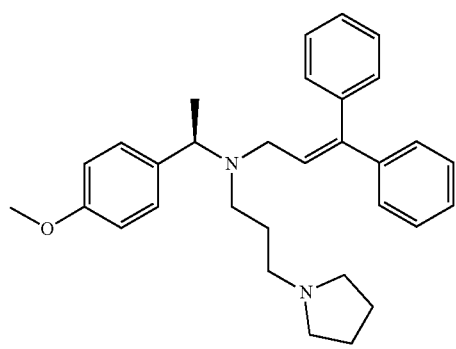 [SMILES: COc1ccc([C@@H](C)N(CC=C(c2ccccc2)c2ccccc2)CCCN2CCCC2)cc1] |

-continued
| Compound Label | Structure |
|---|---|
| (R)-1-(3,3-diphenylallyl)-3-ethyl-1-(1-(4-methoxyphenyl)ethyl)urea (NY0504) | 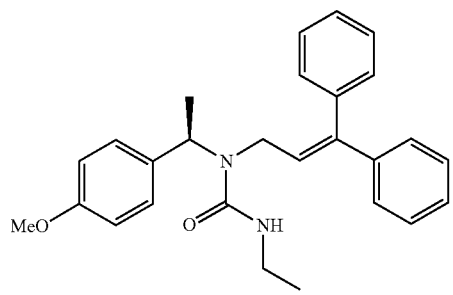 [SMILES: CCNC(=O)N(CC=C(c1ccccc1)c1ccccc1)[C@H](C)c1ccc(OC)cc1] |
| (R)-N-(1-(4-fluorophenyl)ethyl)-N-(2-(4-methylpiperazin-1-yl)ethyl)-3,3-diphenylprop-2-en-1-amine (NY0505) | 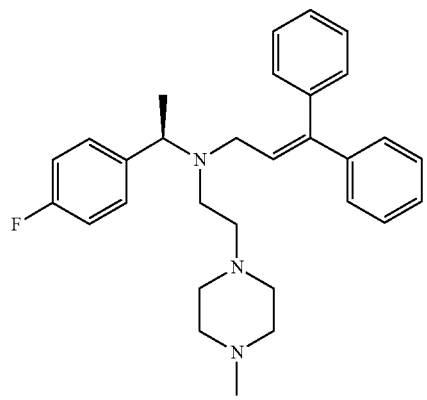 [SMILES: C[C@H](c1ccc(F)cc1)N(CC=C(c1ccccc1)c1ccccc1)CCN1CCN(C)CC1] |
| (R)-N-(1-(4-fluorophenyl)ethyl)-3,3-diphenyl-N-(2-(pyrrolidin-1-yl)ethyl)prop-2-en-1-amine (NY0506) | 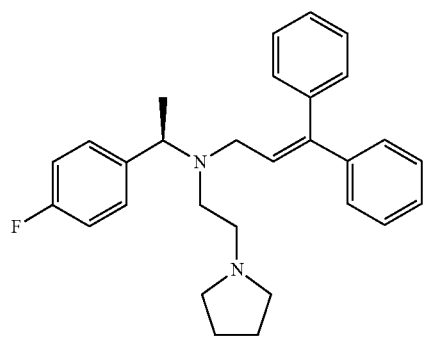 [SMILES: C[C@H](c1ccc(F)cc1)N(CC=C(c1ccccc1)c1ccccc1)CCN1CCCC1] |
| (R)-3-butyl-1-(3,3-diphenylallyl)-1-(1-(4-methoxyphenyl)ethyl)urea (NY0507) | 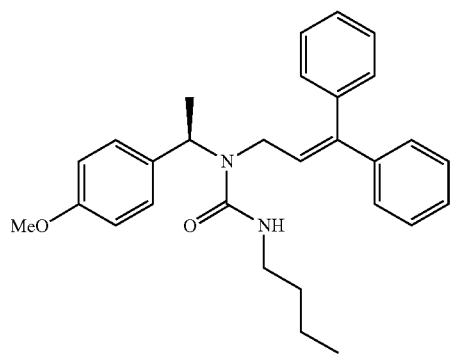 [SMILES: CCCCNC(=O)N(CC=C(c1ccccc1)c1ccccc1)[C@H](C)c1ccc(OC)cc1] |

| Compound Label | Structure |
|---|---|
| (R)-N-(2-(4-methylpiperazin-1-yl)ethyl)-3,3-diphenyl-N-(1-phenylethyl)prop-2-en-1-amine (NY0513) | 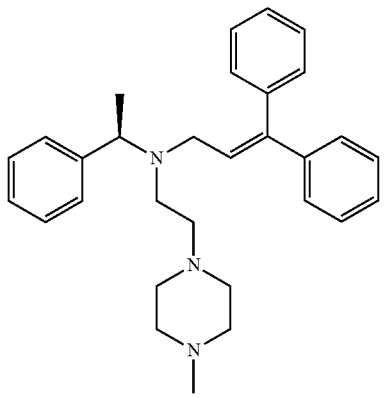 [SMILES: C[C@H](c1ccccc1)N(CC=C(c1ccccc1)c1ccccc1)CCN1CCN(C)CC1] |
| N-(3,3-diphenylallyl)-1-phenylcyclohexan-1-amine (NY0514) | 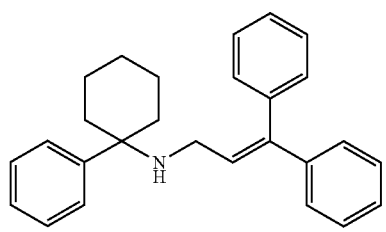 [SMILES: C(CNC1(c2ccccc2)CCCCC1)=C(c1ccccc1)c1ccccc1] |
| (R)-N-(1-(4-chlorophenyl)ethyl)-N-(2-(4-methylpiperazin-1-yl)ethyl)-3,3-diphenylprop-2-en-1-amine (NY0518) | 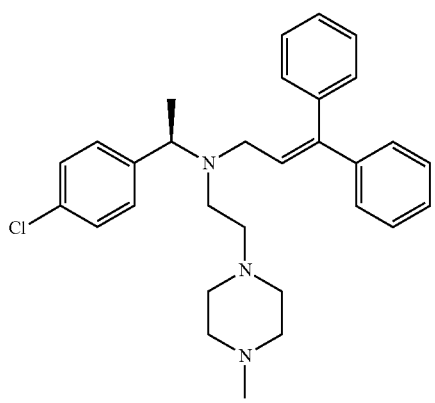 [SMILES: C[C@H](c1ccc(Cl)cc1)N(CC=C(c1ccccc1)c1ccccc1)CCN1CCN(C)CC1] |
| (R)-N-(1-(4-chlorophenyl)ethyl)-3,3-diphenyl-N-(2-(pyrrolidin-1-yl)ethyl)prop-2-en-1-amine (NY0519) | 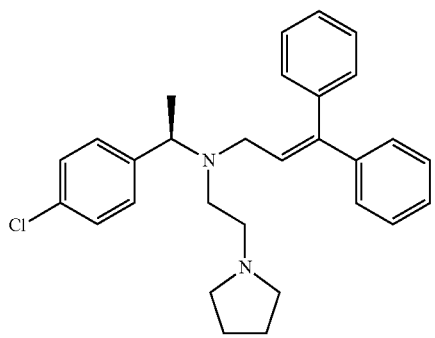 [SMILES: C[C@H](c1ccc(Cl)cc1)N(CC=C(c1ccccc1)c1ccccc1)CCN1CCCC1] |

-continued
| Compound Label | Structure |
|---|---|
| (R)-3-cyclohexyl-1-(3,3-diphenylallyl)-1-(1-(4-methoxyphenyl)ethyl)urea (NY0521) | 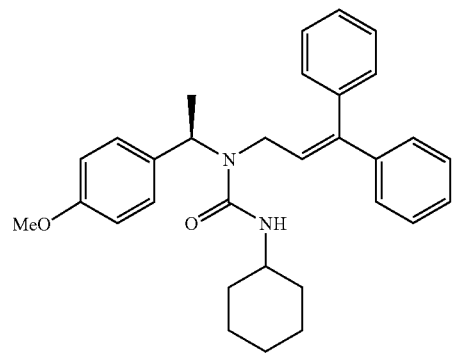 [SMILES: COc1ccc([C@@H](C)N(CC=C(c2ccccc2)c2ccccc2)C(=O)NC2CCCCC2)cc1] |
| (R)-N-(2-(4-methylpiperazin-1-yl)ethyl)-N-(1-(4-nitrophenyl)ethyl)-3,3-diphenylprop-2-en-1-amine (NY0522) | 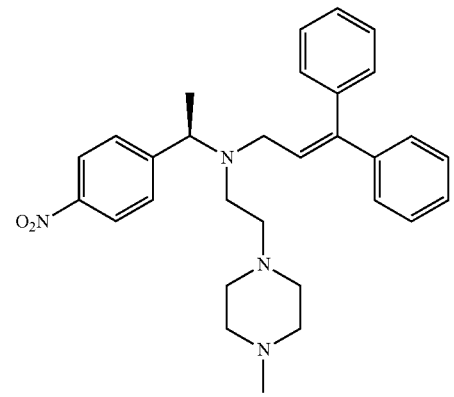 [SMILES: C[C@H](c1ccc([N+](=O)[O-])cc1)N(CC=C(c1ccccc1)c1ccccc1)CCN1CCN(C)CC1] |
| methyl (R)-2-(bis(3,3-diphenylallyl)amino)-2-phenylacetate (NY055101) | 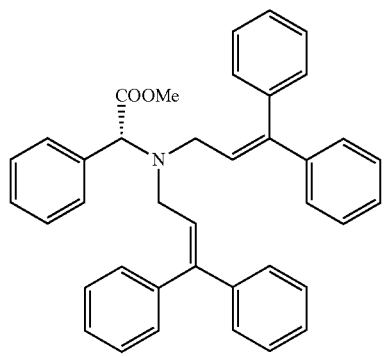 [SMILES: COC(=O)[C@@H](c1ccccc1)N(CC=C(c1ccccc1)c1ccccc1)CC=C(c1ccccc1)c1ccccc1] |
| Methyl (R)-2-((3,3-diphenylallyl)amino)-2-phenylacetate (NY055102) | 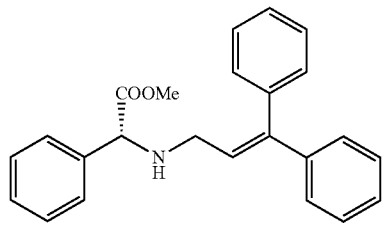 [SMILES: COC(=O)[C@H](NCC=C(c1ccccc1)c1ccccc1)c1ccccc1] |
| (R)-2-(10,11-dihydro-5H-dibenzo[b,f]azepin-5-yl)-N-(1-(4-fluorophenyl)ethyl)ethan-1-amine (NY0552) | 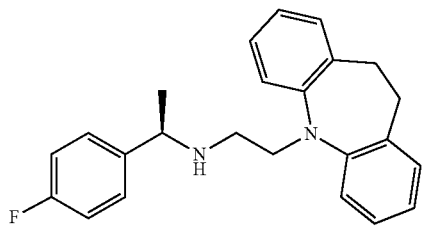 [SMILES: C[C@@H](NCCN1c2ccccc2CCc2ccccc21)c1ccc(F)cc1] |

| Compound Label | Structure |
|---|---|
| (R)-2-(10,11-dihydro-5H-dibenzo[b,f]azepin-5-yl)-N-(1-phenylethyl)ethan-1-amine (NY0553) | 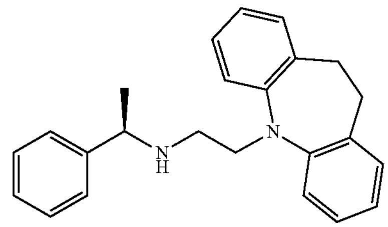 [SMILES: C[C@@H](NCCN1c2ccccc2CCc2ccccc21)c1ccccc1] |
| methyl (R)-2-(3-(tert-butyl)-1-(3,3-diphenylallyl)ureido)-2-phenylacetate (NY0544) | 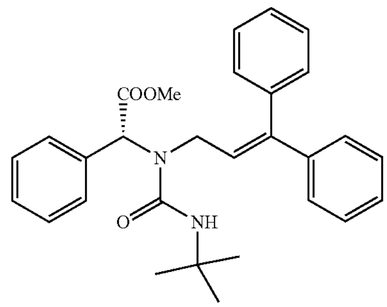 [SMILES: COC(=O)[C@@H](c1ccccc1)N(CC=C(c1ccccc1)c1ccccc1)C(=O)NC(C)(C)C] |
| (R)-2-((3,3-diphenylallyl)amino)-2-phenylacetic acid (NY0555) | 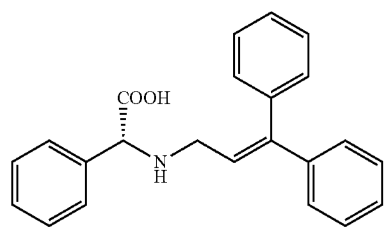 [SMILES: O=C(O)[C@H](NCC=C(c1ccccc1)c1ccccc1)c1ccccc1] |
| (R)-2-((3,3-diphenylallyl)amino)-1-(4-methylpiperazin-1-yl)-2-phenylethan-1-one (NY0557) | 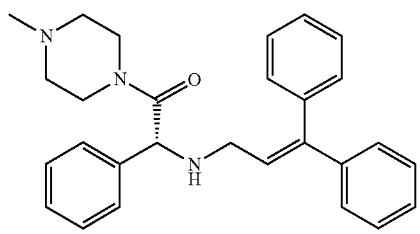 [SMILES: CN1CCN(C(=O)[C@H](NCC=C(c2ccccc2)c2ccccc2)c2ccccc2)CC1] |
| methyl ((R)-2-((3,3-diphenylallyl)amino)-2-phenylacetyl)-L-leucinate (NY0566) | 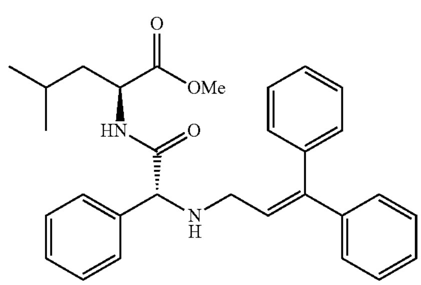 [SMILES: COC(=O)[C@H](CC(C)C)NC(=O)[C@H](NCC=C(c1ccccc1)c1ccccc1)c1ccccc1] |
| (R)-N'-acetyl-2-((3,3-diphenylallyl)amino)-2-phenylacetohydrazide (NY0568) | 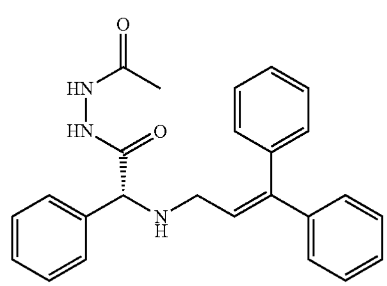 [SMILES: CC(=O)NNC(=O)[C@H](NCC=C(c1ccccc1)c1ccccc1)c1ccccc1] |

| Compound Label | Structure |
| --- | --- |
| (R)-2-((3,3-diphenylallyl)amino)-2-phenylacetamide (NY0569) | 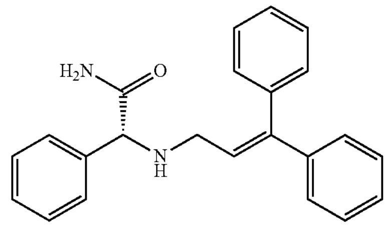 [SMILES: NC(=O)[C@H](NCC=C(c1ccccc1)c1ccccc1)c1ccccc1] |
| (R)-N-((5-methyl-1,3,4-oxadiazol-2-yl)(phenyl)methyl)-3,3-diphenylprop-2-en-1-amine (NY0570) | 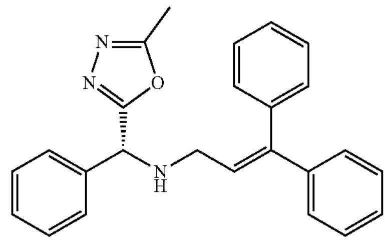 [SMILES: Cc1nnc([C@H](NCC=C(c2ccccc2)c2ccccc2)c2ccccc2)o1] |
| (R)-1-(10H-phenothiazin-10-yl)-2-((1-phenylethyl)amino)ethan-1-one (NY0572) | 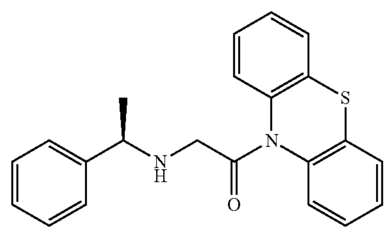 [SMILES: C[C@@H](NCC(=O)N1c2ccccc2Sc2ccccc21)c1ccccc1] |
| (R)-2-((1-(4-fluorophenyl)ethyl)amino)-1-(10H-phenothiazin-10-yl)ethan-1-one (NY0573) | 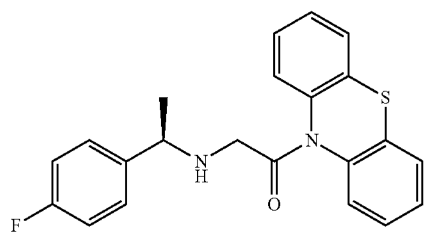 [SMILES: C[C@@H](NCC(=O)N1c2ccccc2Sc2ccccc21)c1ccc(F)cc1] |
| (R)-N-(2-(10H-phenothiazin-10-yl)ethyl)-1-phenylethan-1-amine (NY0574) | 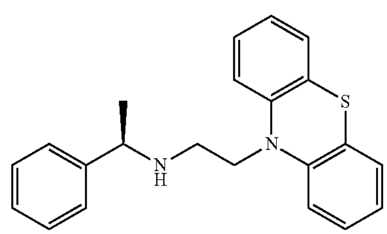 [SMILES: C[C@@H](NCCN1c2ccccc2Sc2ccccc21)c1ccccc1] |
| (R)-N-(2-(10H-phenothiazin-10-yl)ethyl)-1-(4-fluorophenyl)ethan-1-amine (NY0575) | 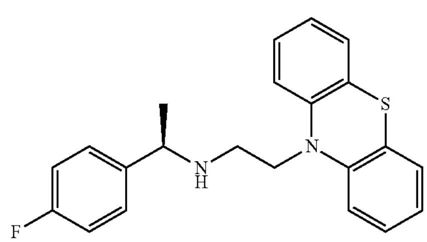 [SMILES: C[C@@H](NCCN1c2ccccc2Sc2ccccc21)c1ccc(F)cc1] |

| Compound Label | Structure |
|---|---|
| (R)-1-(10,11-dihydro-5H-dibenzo[b,f]azepin-5-yl)-2-((1-(4-fluorophenyl)ethyl)amino)ethan-1-one (NY0583) | 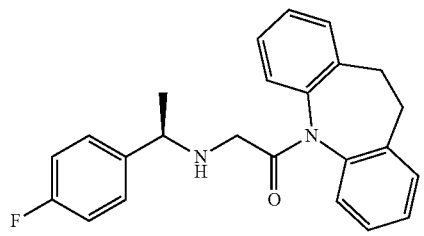 [SMILES: C[C@@H](NCC(=O)N1c2ccccc2CCc2ccccc21)c1ccc(F)cc1] |
| (R)-1-(10,11-dihydro-5H-dibenzo[b,f]azepin-5-yl)-2-((1-phenylethyl)amino)ethan-1-one (NY0584) | 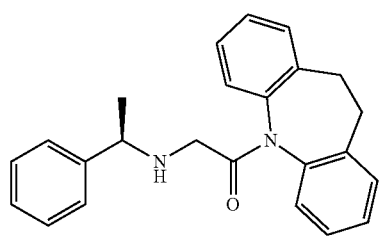 [SMILES: C[C@@H](NCC(=O)N1c2ccccc2CCc2ccccc21)c1ccccc1] |
| (R)-N-(tert-butyl)-4-(2-((3,3-diphenylallyl)(1-(4-methoxyphenyl)ethyl)amino)ethyl) piperazine-1-carboxamide (NY0587) | 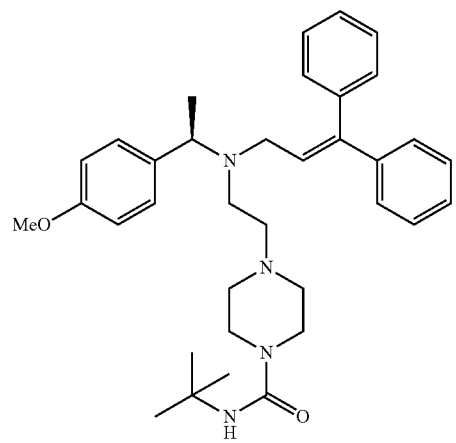 [SMILES: COc1ccc([C@@H](C)N(CC=C(c2ccccc2)c2ccccc2)CCN2CCN(C(=O)NC(C)(C)C)CC2)cc1] |
| (R)-N-(2-(4-ethylpiperazin-1-yl)ethyl)-N-(1-(4-methoxyphenyl)ethyl)-3,3-diphenylprop-2-en-1-amine (NY0589) | 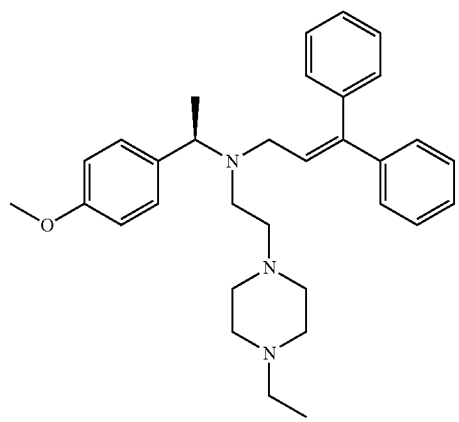 [SMILES: CCN1CCN(CCN(CC=C(c2ccccc2)c2ccccc2)[C@H](C)c2ccc(OC)cc2)CC1] |

| Compound Label | Structure |
|---|---|
| (1R,2S)-N-(3,3-diphenylallyl)-N-(2-(4-methylpiperazin-1-yl)ethyl)-2-phenylcyclopropan-1-amine (NY0590) | 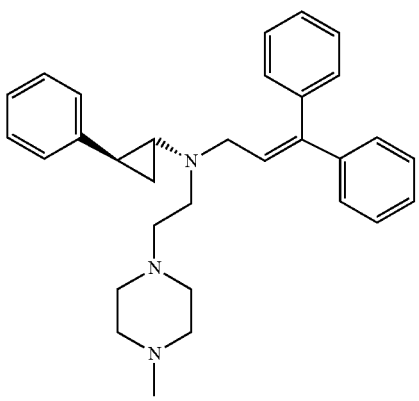 |
| 1-(4-(2-((3,3-diphenylallyl)((R)-1-(4-methoxyphenyl)ethyl)amino)ethyl)piperazin-1-yl)-2-fluoropropan-1-one (NY0591) | 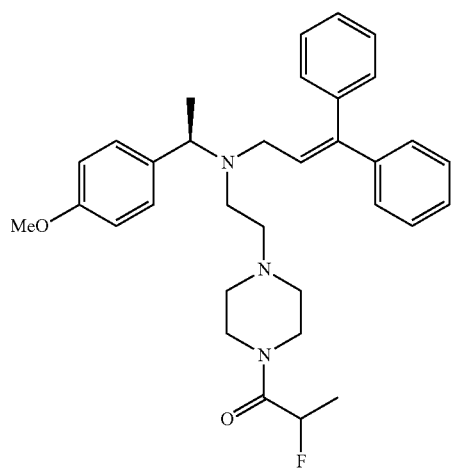 |
| (1R,2S)-N-(3,3-diphenylallyl)-2-phenyl-N-(2-(pyrrolidin-1-yl)ethyl)cyclopropan-1-amine (NY0592) | 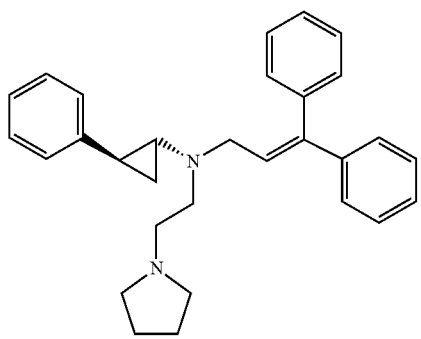 |
| (R)-N-(2-(azetidin-1-yl)ethyl)-N-(1-(4-methoxyphenyl)ethyl)-3,3-diphenylprop-2-en-1-amine (NY0593) | 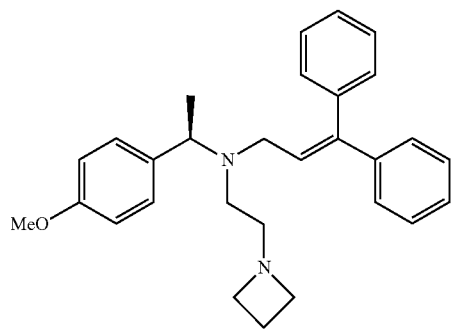 [SMILES: COc1ccc([C@@H](C)N(CC=C(c2ccccc2)c2ccccc2)CCN2CCC2)cc1] |

-continued

| Compound Label | Structure |
|---|---|
| (R)-N-(2-(4-propylpiperazin-1-yl)ethyl)-N-(1-(4-methoxyphenyl)ethyl)-3,3-diphenylprop-2-en-1-amine (NY0594) | 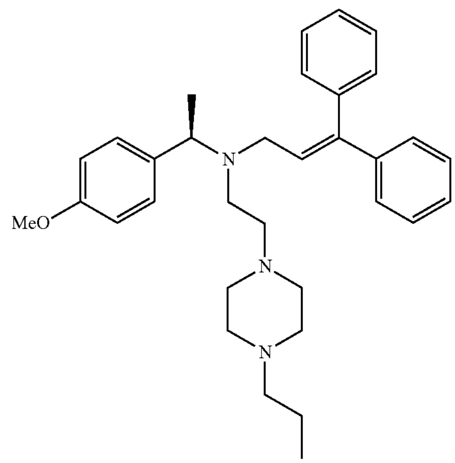 |
| (R)-N-(3,3-diphenylallyl)-N-(1-(4-methoxyphenyl)ethyl)-2-(pyrrolidin-1-yl)acetamide (PW124) | 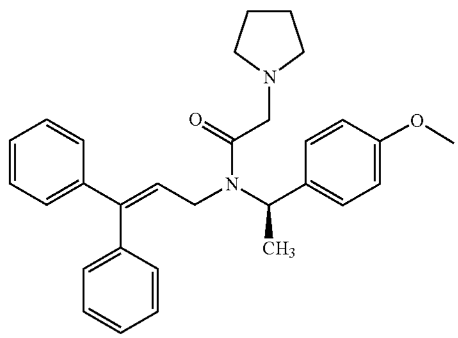 [SMILES: COc1ccc([C@@H](C)N(CC=C(c2ccccc2)c2ccccc2)C(=O)CN2CCCC2)cc1] |
| (R)-N-(3,3-diphenylallyl)-N-(1-(4-methoxyphenyl)ethyl)-2-(4-methylpiperazin-1-yl)acetamide (PW125) | 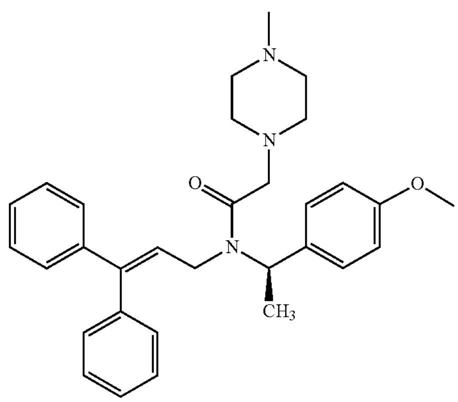 [SMILES: COc1ccc([C@@H](C)N(CC=C(c2ccccc2)c2ccccc2)C(=O)CN2CCN(C)CC2)cc1] |
| (R)-N-(3,3-diphenylallyl)-2-(4-hydroxypiperidin-1-yl)-N-(1-(4-methoxyphenyl)ethyl)acetamide (PW126) | 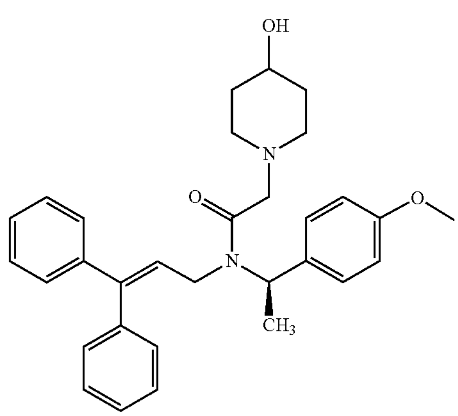 [SMILES: COc1ccc([C@@H](C)N(CC=C(c2ccccc2)c2ccccc2)C(=O)CN2CCC(O)CC2)cc1] |

| Compound Label | Structure |
|---|---|
| (R)-N¹-(3,3-diphenylallyl)-N²-(3-(4-fluorophenyl)-1H-pyrazol-5-yl)-N¹-(1-(4-fluorophenyl)ethyl)ethane-1,2-diamine (PW2100) | 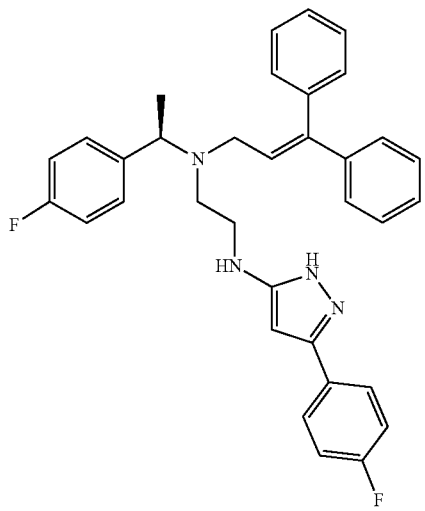 [SMILES: C[C@H](c1ccc(F)cc1)N(CC=C(c1ccccc1)c1ccccc1)CCNc1cc(-c2ccc(F)cc2)n[nH]1] |
| N-(3,3-diphenylallyl)-4-fluoro-N-(2-(pyrrolidin-1-yl)ethyl)benzamide (PW276) | 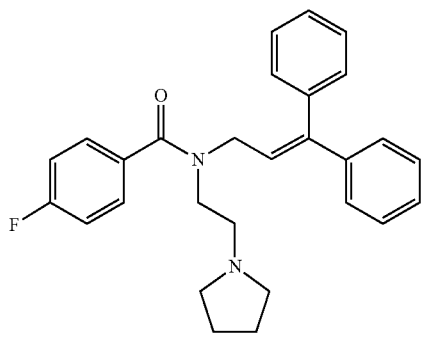 |
| N-(3,3-diphenylallyl)-4-fluoro-N-(2-(pyrrolidin-1-yl)ethyl)benzenesulfonamide (PW277) | 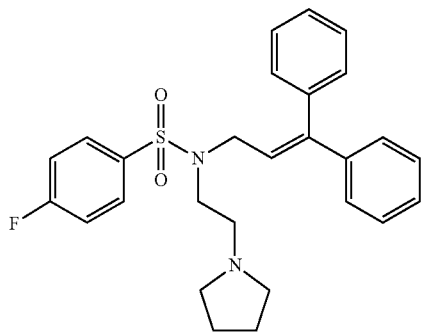 |
| N-(4-fluorobenzyl)-3,3-diphenyl-N-(2-(pyrrolidin-1-yl)ethyl)prop-2-en-1-amine (PW278) | 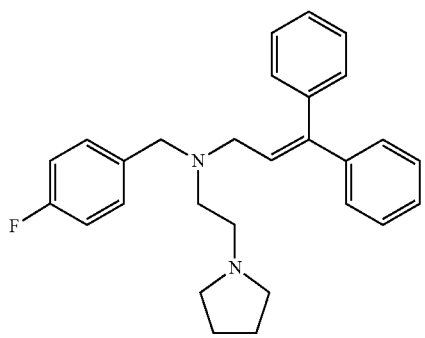 |

| Compound Label | Structure |
|---|---|
| 1-(3,3-diphenylallyl)-3-(4-fluorophenyl)-1-(2-(pyrrolidin-1-yl)ethyl)urea (PW279) | 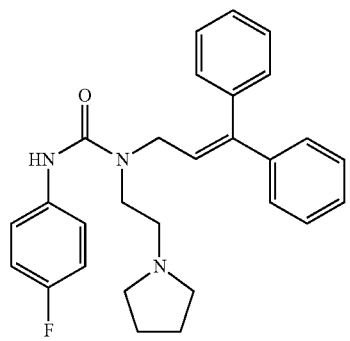 |
| benzyl (3,3-diphenylallyl)(2-(pyrrolidin-1-yl)ethyl)carbamate (PW280) | 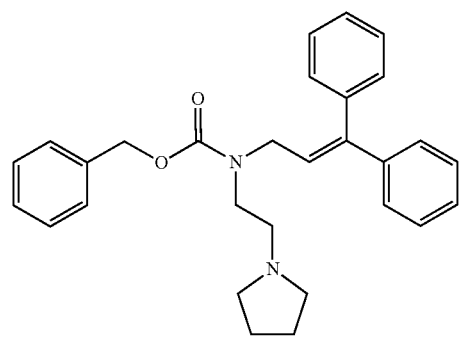 [SMILES: O=C(OCc1ccccc1)N(CC=C(c1ccccc1)c1ccccc1)CCN1CCCC1] |
| 3-amino-N-(3,3-diphenylallyl)-N-(2-(pyrrolidin-1-yl)ethyl)pyrazine-2-carboxamide (PW282) | 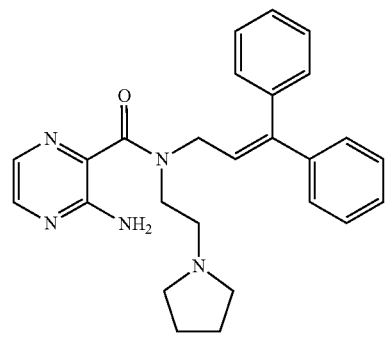 [SMILES: Nc1nccnc1C(=O)N(CC=C(c1ccccc1)c1ccccc1)CCN1CCCC1] |
| 5-(4-chlorophenyl)-N-(3,3-diphenylallyl)-N-(2-(pyrrolidin-1-yl)ethyl)isoxazole-3-carboxamide(PW283) | 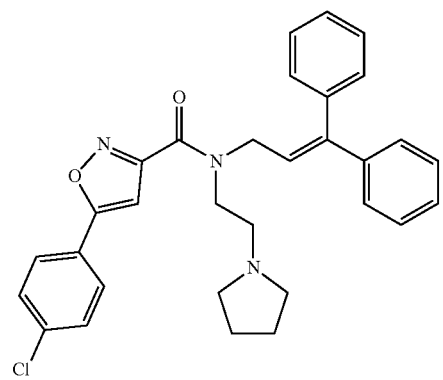 [SMILES: O=C(c1cc(-c2ccc(Cl)cc2)on1)N(CC=C(c1ccccc1)c1ccccc1)CCN1CCCC1] |

| Compound Label | Structure |
|---|---|
| N-(3,3-diphenylallyl)-N-(2-(pyrrolidin-1-yl)ethyl)cinnamamide (PW284) | 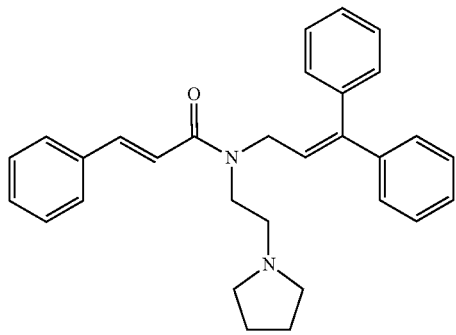 [SMILES: O=C(/C=C/c1ccccc1)N(CC=C(c1ccccc1)c1ccccc1)CCN1CCCC1] |
| N-(3,3-diphenylallyl)-N-(2-(pyrrolidin-1-yl)ethyl)quinoxaline-2-carboxamide (PW285) | 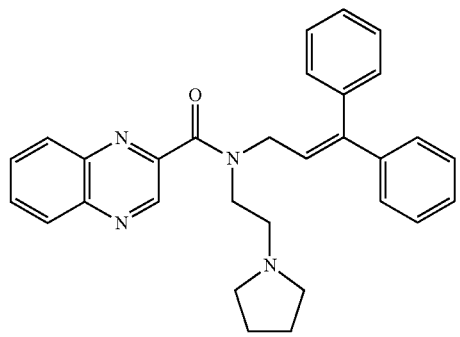 [SMILES: O=C(c1cnc2ccccc2n1)N(CC=C(c1ccccc1)c1ccccc1)CCN1CCCC1] |
| N-(3,3-diphenylallyl)-N-(2-(pyrrolidin-1-yl)ethyl)pyrazolo[1,5-a]pyridine-2-carboxamide (PW286) | 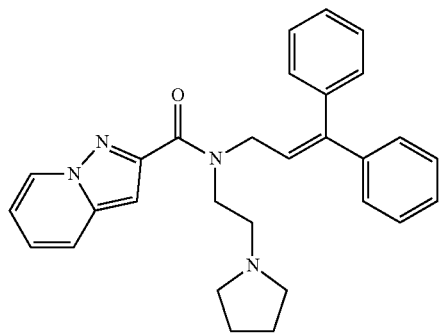 [SMILES: O=C(c1cc2ccccn2n1)N(CC=C(c1ccccc1)c1ccccc1)CCN1CCCC1] |
| N-((1H-pyrrolo[2,3-b]pyridin-2-yl)methyl)-3,3-diphenyl-N-(2-(pyrrolidin-1-yl)ethyl)prop-2-en-1-amine (PW293) | 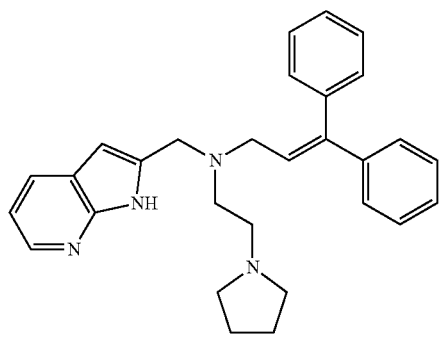 [SMILES: C(CN(CCN1CCCC1)Cc1cc2cccnc2[nH]1)=C(c1ccccc1)c1ccccc1] |

| Compound Label | Structure |
|---|---|
| N-((6-bromopyridin-2-yl)methyl)-3,3-diphenyl-N-(2-(pyrrolidin-1-yl)ethyl)prop-2-en-1-amine (PW295) | 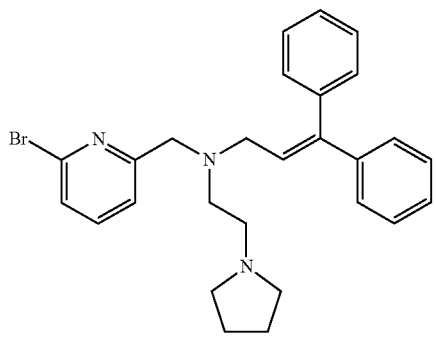 [SMILES: Brc1cccc(CN(CC=C(c2ccccc2)c2ccccc2)CCN2CCCC2)n1] |
| (R)-N-(2-(1H-pyrrolo[2,3-b]pyridin-1-yl)ethyl)-N-(1-(4-fluorophenyl)ethyl)-3,3-diphenylprop-2-en-1-amine (PW297) | 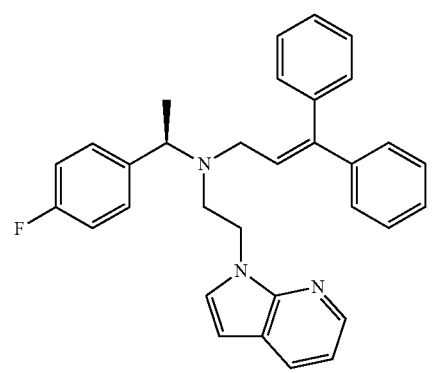 [SMILES: C[C@H](c1ccc(F)cc1)N(CC=C(c1ccccc1)c1ccccc1)CCn1ccc2cccnc21] |
| (R)-N-(2-(3,5-dimethyl-1H-pyrazol-1-yl)ethyl)-N-(1-(4-fluorophenyl)ethyl)-3,3-diphenylprop-2-en-1-amine (PW299) | 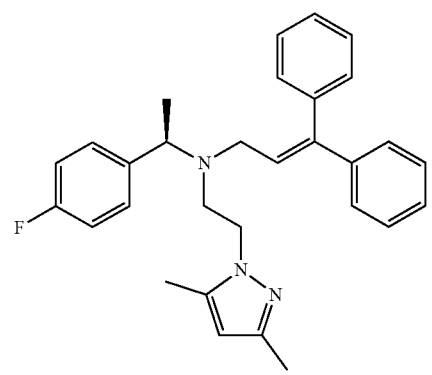 [SMILES: Cc1cc(C)n(CCN(CC=C(c2ccccc2)c2ccccc2)[C@H](C)c2ccc(F)cc2)n1] |
| (R)-2-(1-(2-((3,3-diphenylallyl)(1-(4-fluorophenyl)ethyl)amino)ethyl)-1H-1,2,3-triazol-4-yl)ethan-1-ol (PW303) | 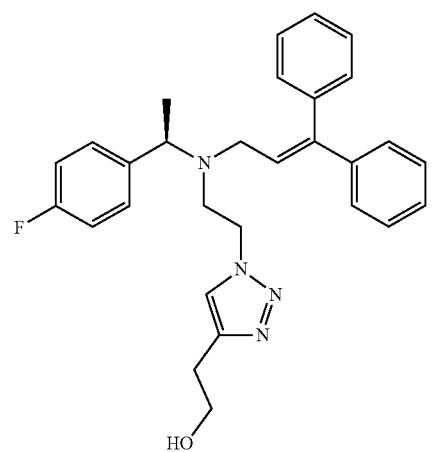 [SMILES: C[C@H](c1ccc(F)cc1)N(CC=C(c1ccccc1)c1ccccc1)CCn1cc(CCO)nn1] |

| Compound Label | Structure |
|---|---|
| (R)-(1-(2-((3,3-diphenylallyl)(1-(4-fluorophenyl)ethyl)amino)ethyl)-1H-1,2,3-triazol-4-yl)methanol (PW304) | 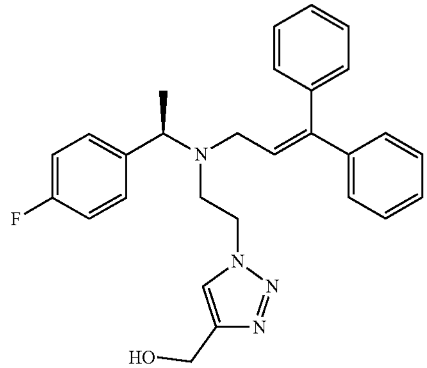 [SMILES: C[C@H](c1ccc(F)cc1)N(CC=C(c1ccccc1)c1ccccc1)CCn1cc(CO)nn1] |
| (R)-N-(2-(4-(aminomethyl)-1H-1,2,3-triazol-1-yl)ethyl)-N-(1-(4-fluorophenyl)ethyl)-3,3-diphenylprop-2-en-1-amine (PW305) | 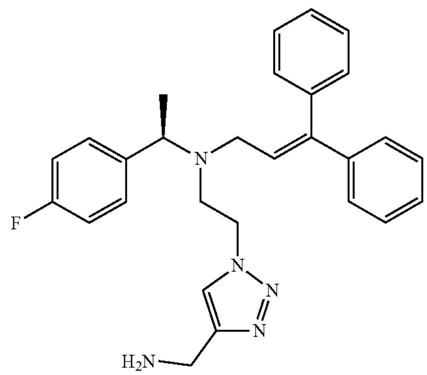 [SMILES: C[C@H](c1ccc(F)cc1)N(CC=C(c1ccccc1)c1ccccc1)CCn1cc(CN)nn1] |
| (R)-N-(2-(4-((dimethylamino)methyl)-1H-1,2,3-triazol-1-yl)ethyl)-N-(1-(4-fluorophenyl)ethyl)-3,3-diphenylprop-2-en-1-amine (PW306) | 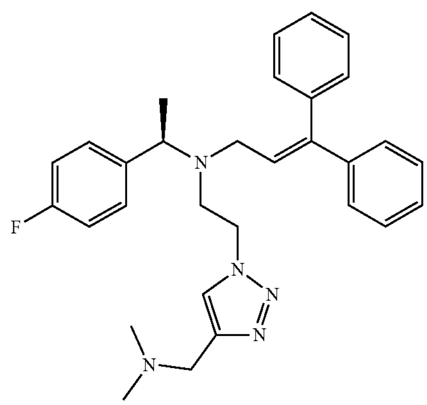 [SMILES: C[C@H](c1ccc(F)cc1)N(CC=C(c1ccccc1)c1ccccc1)CCn1cc(CN(C)C)nn1] |
| methyl (R)-1-(2-((3,3-diphenylallyl)(1-(4-fluorophenyl)ethyl)amino)ethyl)-1H-1,2,3-triazole-4-carboxylate (PW307) | 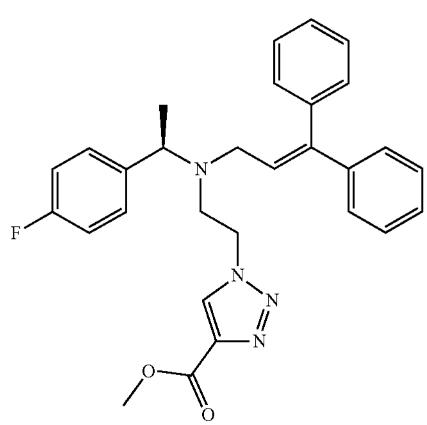 [SMILES: COC(=O)c1cn(CCN(CC=C(c2ccccc2)c2ccccc2)[C@H](C)c2ccc(F)cc2)nn1] |

-continued

| Compound Label | Structure |
|---|---|
| (R)-N-(2-(4-(4-fluorophenyl)-1H-1,2,3-triazol-1-yl)ethyl)-N-(1-(4-fluorophenyl)ethyl)-3,3-diphenylprop-2-en-1-amine (PW308) | 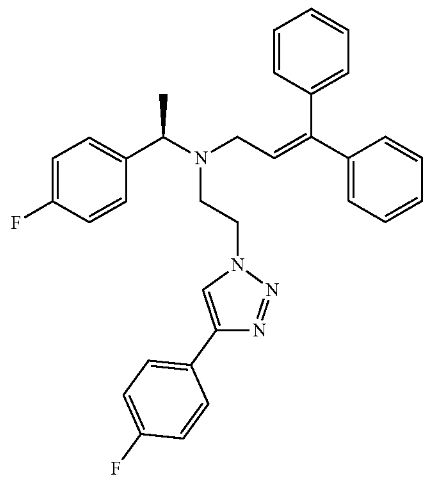 [SMILES: C[C@H](c1ccc(F)cc1)N(CC=C(c1ccccc1)c1ccccc1)CCn1cc(-c2ccc(F)cc2)nn1] |
| (R)-1-(1-(4-Fluorophenyl)ethyl)-1-(2-(pyrrolidin-1-yl)ethyl)-3-(4-(trifluoromethyl)phenyl)urea (PW0321) | 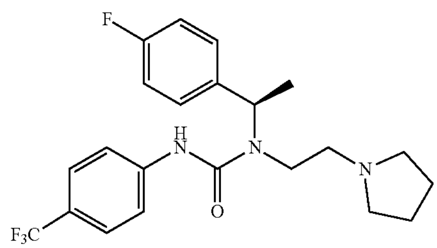 [SMILES: C[C@H](c1ccc(F)cc1)N(CCN1CCCC1)C(=O)Nc1ccc(C(F)(F)F)cc1] |
| (R)-N-(1-(4-Fluorophenyl)ethyl)-N-(2-(pyrrolidin-1-yl)ethyl)-4-(trifluoromethyl)benzamide (PW0322) | 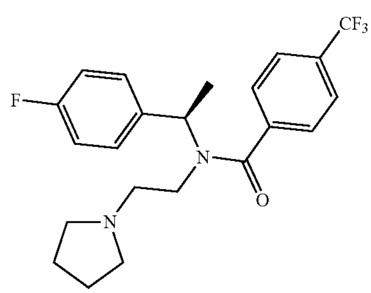 [SMILES: C[C@H](c1ccc(F)cc1)N(CCN1CCCC1)C(=O)c1ccc(C(F)(F)F)cc1] |
| (R)-N-(1-(4-Fluorophenyl)ethyl)-5-(4-methoxyphenyl)-N-(2-(pyrrolidin-1-yl)ethyl)isoxazole-3-carboxamide (PW0323) | 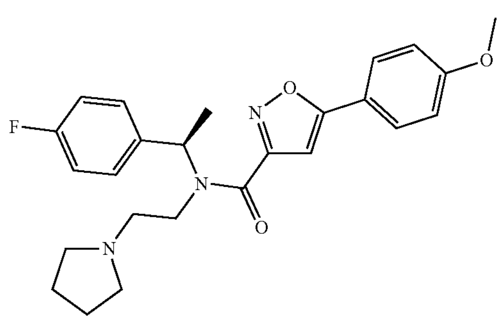 [SMILES: COc1ccc(-c2cc(C(=O)N(CCN3CCCC3)[C@H](C)c3ccc(F)cc3)no2)cc1] |
| (R)-N-(1-(4-Fluorophenyl)ethyl)-4-phenyl-N-(2-(pyrrolidin-1-yl)ethyl)picolinamide (PW0324) | 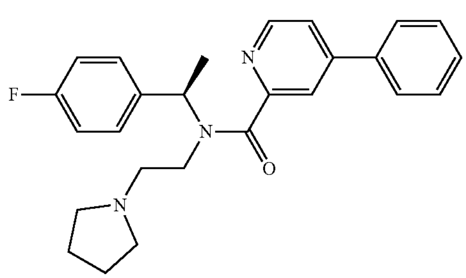 [SMILES: C[C@H](c1ccc(F)cc1)N(CCN1CCCC1)C(=O)c1cc(-c2ccccc2)ccn1] |

| Compound Label | Structure |
| --- | --- |
| (R)-N-(1-(4-Fluorophenyl)ethyl)-N-(2-(pyrrolidin-1-yl)ethyl)-3,3-di-p-tolylprop-2-en-1-amine (PW0327) | 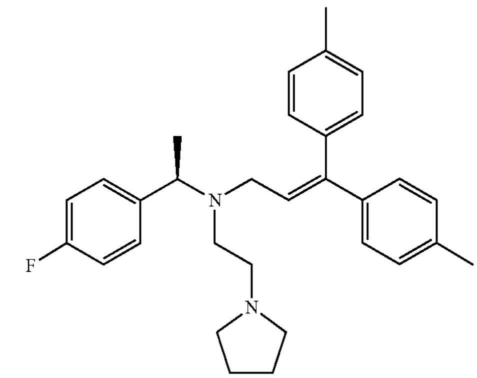 [SMILES: Cc1ccc(C(=CCN(CCN2CCCC2)[C@H](C)c2ccc(F)cc2)c2ccc(C)cc2)cc1] |
| (R)-N-(1-(4-Fluorophenyl)ethyl)-3,3-bis(4-methoxyphenyl)-N-(2-(pyrrolidin-1-yl)ethyl)prop-2-en-1-amine (PW0356) | 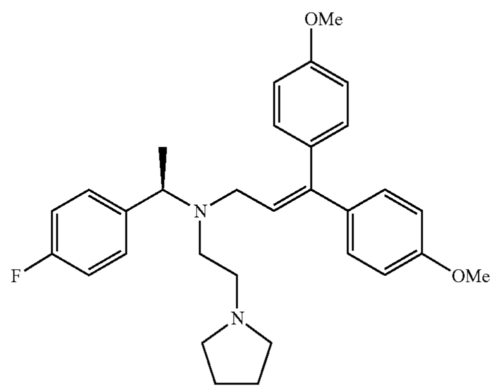 [SMILES: COc1ccc(C(=CCN(CCN2CCCC2)[C@H](C)c2ccc(F)cc2)c2ccc(OC)cc2)cc1] |
| (R)-N-(1-(4-Fluorophenyl)ethyl)-3,3-bis(3-methoxyphenyl)-N-(2-(pyrrolidin-1-yl)ethyl)prop-2-en-1-amine (PW0357) | 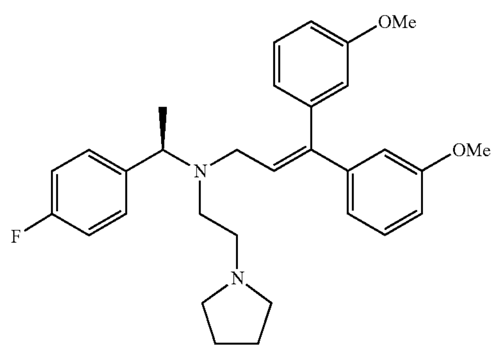 [SMILES: COc1cccc(C(=CCN(CCN2CCCC2)[C@H](C)c2ccc(F)cc2)c2cccc(OC)c2)c1] |
| (R)-N-(1-(4-Fluorophenyl)ethyl)-N-(2-(pyrrolidin-1-yl)ethyl)-3,3-bis(3,4,5-trimethoxyphenyl)prop-2-en-1-amine (PW0358) | 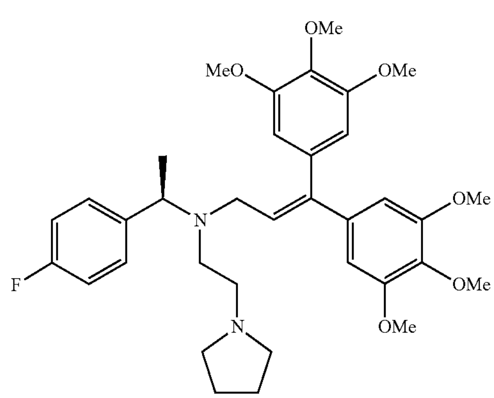 [SMILES: COc1cc(C(=CCN(CCN2CCCC2)[C@H](C)c2ccc(F)cc2)c2cc(OC)c(OC)c(OC)c2)cc(OC)c1OC] |

| Compound Label | Structure |
| --- | --- |
| (R)-N-(1-(4-Fluorophenyl)ethyl)-N-(2-(pyrrolidin-1-yl)ethyl)-3,3-di-p-tolylprop-2-en-1-amine (PW0448) | 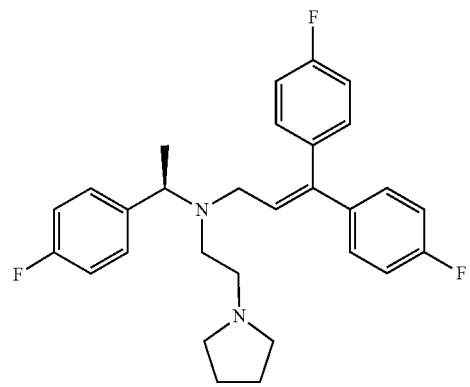 [SMILES: C[C@H](c1ccc(F)cc1)N(CC=C(c1ccc(F)cc1)c1ccc(F)cc1)CCN1CCCC1] |
| (R,E)-3-(4-fluorophenyl)-N-(1-(4-fluorophenyl)ethyl)-3-(4-methoxyphenyl)-N-(2-(pyrrolidin-1-yl)ethyl)prop-2-en-1-amine (PW0454) | 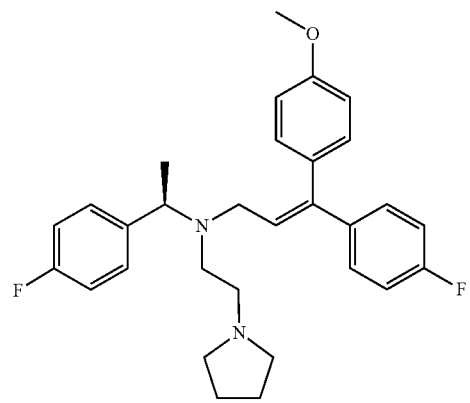 [SMILES: COc1ccc(/C(=C\CN(CCN2CCCC2)[C@H](C)c2ccc(F)cc2)c2ccc(F)cc2)cc1] |
| (R,E)-3-(4-fluorophenyl)-N-(1-(4-fluorophenyl)ethyl)-N-(2-(pyrrolidin-1-yl)ethyl)-3-(4-(trifluoromethyl)phenyl)prop-2-en-1-amine (PW0455) | 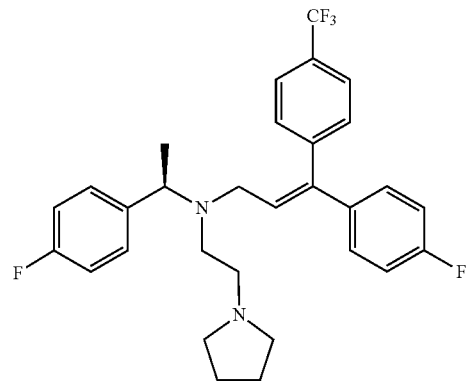 [SMILES: C[C@H](c1ccc(F)cc1)N(C/C=C(/c1ccc(F)cc1)c1ccc(C(F)(F)F)cc1)CCN1CCCC1] |
| (R,Z)-N-(1-(4-fluorophenyl)ethyl)-3-(4-methoxyphenyl)-3-phenyl-N-(2-(pyrrolidin-1-yl)ethyl)prop-2-en-1-amine (PW460) | 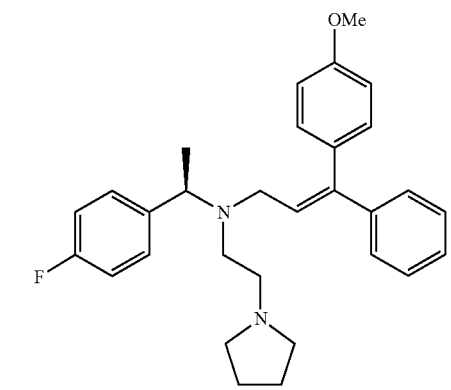 [SMILES: COc1ccc(/C(=C\CN(CCN2CCCC2)[C@H](C)c2ccc(F)cc2)c2ccccc2)cc1] |

| Compound Label | Structure |
|---|---|
| (R,Z)-N-(1-(4-fluorophenyl)ethyl)-3-phenyl-N-(2-(pyrrolidin-1-yl)ethyl)-3-(4-(trifluoromethoxy)phenyl)prop-2-en-1-amine (PW361) | 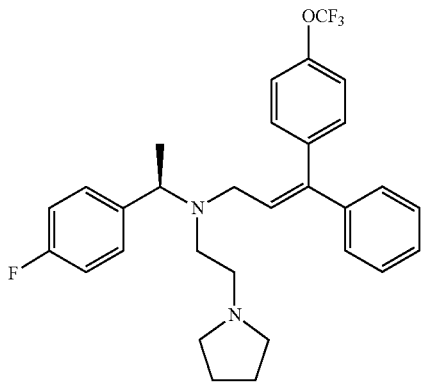 [SMILES: C[C@H](c1ccc(F)cc1)N(C/C=C(/c1ccccc1)c1ccc(OC(F)(F)F)cc1)CCN1CCCC1] |

2.1. Synthesis of Compounds of the Invention

The description of preparation of certain compounds of the invention is meant to be exemplary of certain embodiments of the invention. The reagents and reactant used for synthetic conversions outlined herein and below is merely exemplary. The invention contemplates using the same or different reagents discussed herein to achieve preparation of the compounds of the invention.

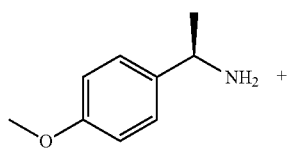

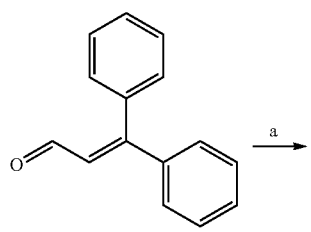

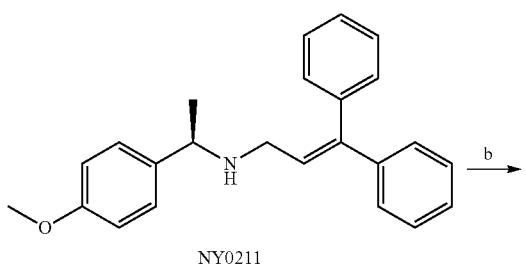

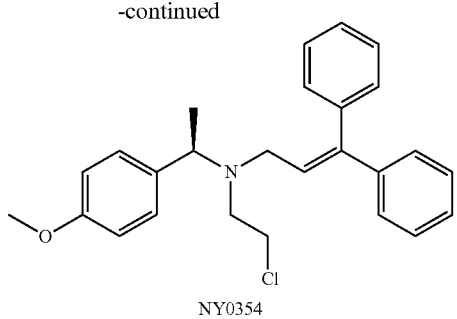

Reagents and conditions: (a) (i) Ti(OiPr)$_4$, 4 Å MS, THF, 65° C., 2 h; ii) NaBH$_4$, MeOH/THF. 0° C., 30 min (b) chloroacetaldehyde, NaBH(OAc)$_3$, ClCH$_2$CH$_2$Cl, 0° C., 2 h In some embodiments, commercially available (R)-1-(4-methoxyphenyl)ethylamine (9a) may be used as the starting synthetic material. Intermediate 10a was prepared via stepwise reductive amination of 9a and β-phenylcinnamylaldehyde as the sole product in a yield of 68%. Alkylation of amine 10a with corresponding alkylating agents yielded compounds 11a, 11c, 11e and 11f in the presence of K$_2$CO$_3$ and KI at reflux. Further reductive amination of 10a with acetaldehyde and 2-chloroacetaldehyde using NaBH(OAc)$_3$ as a reducing agent provided compounds 11b and 11d. Compounds 12a-i were obtained by further substitution of 11 d with the corresponding acyclic or cyclic amines.

In further embodiments, the three pharmacophore moieties (P1, P2 and P3) were systematically modified. A more polar nitrogen atom may be introduced at the terminal of P3 moiety to improve the aqueous solubility and form N,N-dialkylamino, or cyclic amino groups to replace the highly lipophilic diphenyl moiety (see e.g., compounds 11, 12 and 14). The other diphenyl group in P2 moiety (of Compound 7) may also be modified. As outlined in Scheme 1, further simplified diphenyl ring analogs 14a-b can be produced through an alternative approach, in which amino linker was introduced, leading to compound 13, followed by installation of allyl or cinnamyl groups.

Scheme 1. Synthetic Route of (R)—N-Substituted-N-(1-(4-methoxypheny)ethyl)-3,3-diphenylprop-2-en-1-amine Derivatives 11a-c, 12a-i and 14a-b[a]
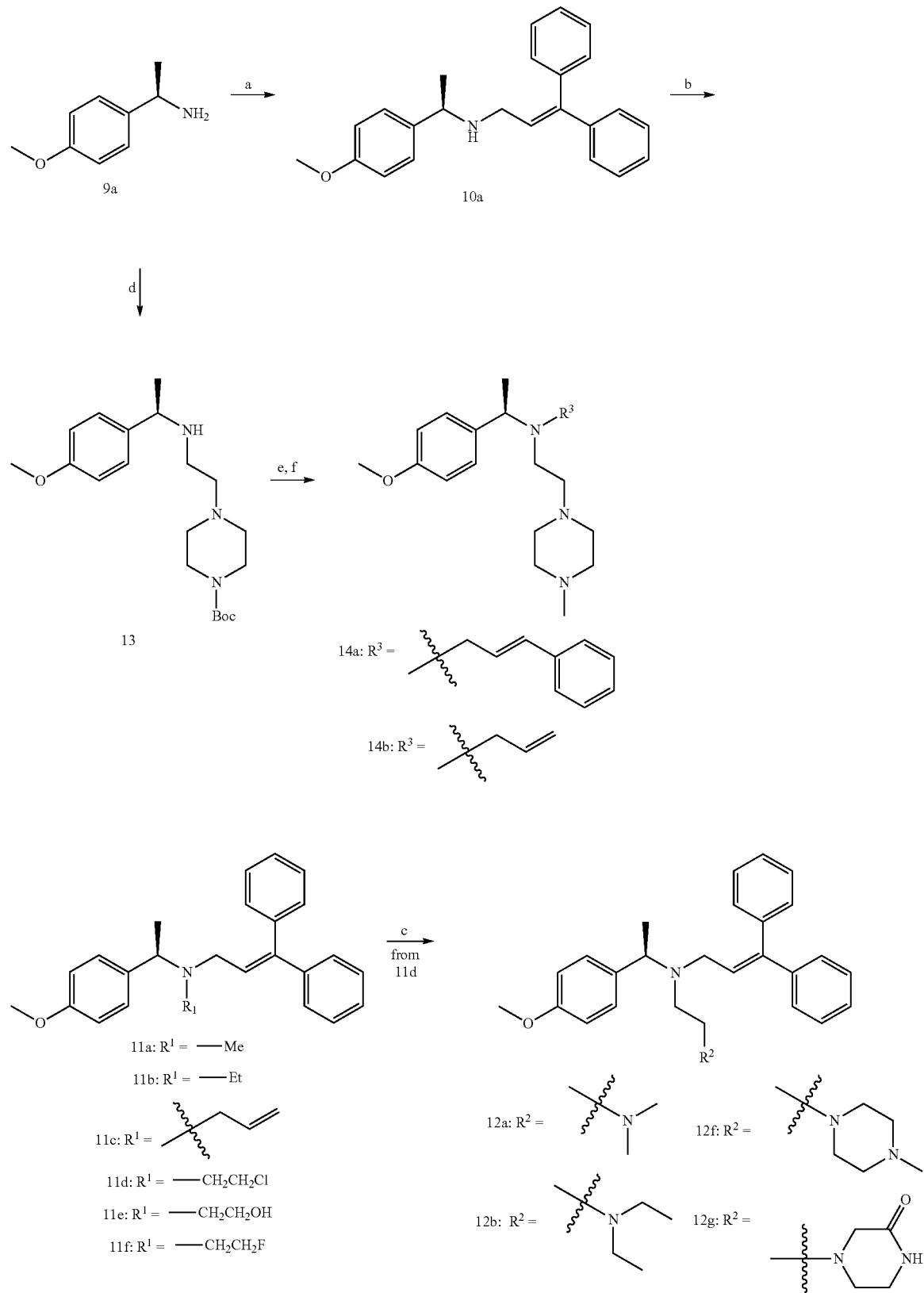

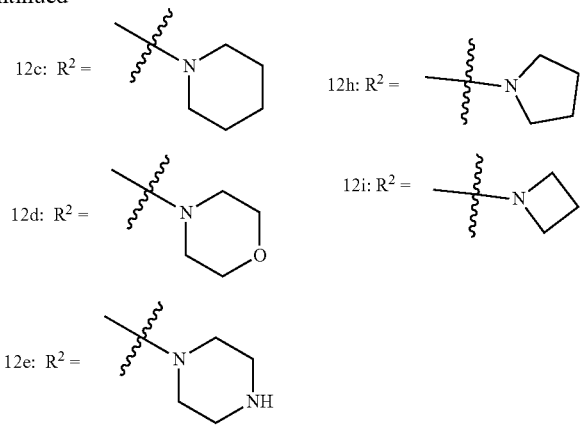

12c: R² = [piperidine]
12d: R² = [morpholine]
12e: R² = [piperazine-NH]
12h: R² = [pyrrolidine]
12i: R² = [azetidine]

<sup>a</sup>Reagents and conditions: (a) i) β-phenylcinnamylaldehyde, 4 Å molecular sieves, anhydrous Na$_2$SO$_4$, THF, rt, 48 h; ii) NaBH$_4$, MeOH, 0° C., 2 h, 68% for two steps; (b) for 11a, MeI, K$_2$CO$_3$, MeCN, reflux, overnight, 34%; for 11b, CH$_3$CHO, NaBH(OAc)$_3$, HOAc, DCE, rt, 24 h, 80%; for 11c, allyl bromide, K$_2$CO$_3$, acetone, 50° C., 6 h, 77%; for 11d, 45 wt. % 2-chloroacetaldehyde aq., NaBH(OAc)$_3$, HOAc, DCE, rt, 2 h, 90%; for 11e, 2-bromoethan-1-ol, DIPEA, MeCN, 80° C., 24 h, 18%; and for 11f, 1-bromo-2-fluoroethane, DIPEA, DMF, 80° C., 16 h, 70%; (c) for 12a-i, R2H, K$_2$CO$_3$, KI, MeCN, reflux, overnight, 31-69%; (d) tert-butyl 4-(2-chloroethyl)piperazine-1-carboxylate, K$_2$CO$_3$, KI, MeCN, 50° C. to reflux, quant.; (e) for 14a, cinnamylaldehyde, NaBH(OAc)$_3$, phosphotungstic acid hydrate, DCE, rt, 48 h, 45% for two steps; for 14b, allyl bromide, K$_2$CO$_3$, KI, MeCN, 50° C., 3 h, 41% for two steps; (f) i) 6N HCl, EtOH, 0° C. to rt, overnight; ii) 37 wt. % formaldehyde aq., NaBH(OAc)$_3$, HOAc, DCE, rt, 24 h, 67% for two steps for 14a, 64% for two steps for 14b.

Scheme 2. Syntheses of N-(1-(Substituted phenyDethyl)-N-(2-(4-methylpiperazin-1-yl)ethyl)-3,3-diphenylprop-2-en-1-amine Derivatives 15a-h<sup>a</sup>

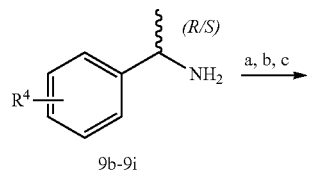

9b-9i a, b, c →

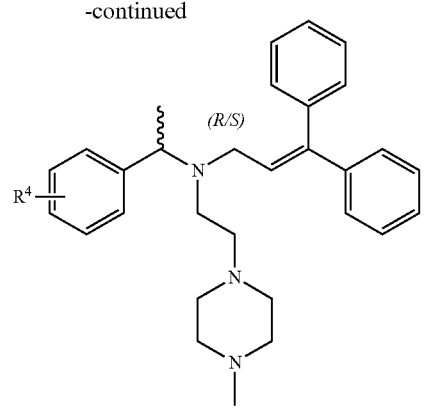

(S) 15a: R⁴ = -4-OMe
(R) 15b: R⁴ = -2-OMe
(R) 15c: R⁴ = -3-OMe
(R) 15d: R⁴ = -H
(R) 15e: R⁴ = -4-F
(R) 15f: R⁴ = -4-Cl
(R) 15g: R⁴ = -3-Cl
(R) 15h: R⁴ = -4-NO$_2$

Reagents and conditions: (a) i) β-phenylcinnamylaldehyde, 4 Å molecular sieves, anhydrous Na$_2$SO$_4$, THF, rt, 48 h; ii) NaBH$_4$, MeOH, 0° C., 2 h, used directly for next step; (b) 45 wt. % 2-chloroacetaldehyde aq., NaBH(OAc)$_3$, HOAc, DCE, rt, 2 h, used directly for next step; (c)1-methylpiperazine, K$_2$CO$_3$, KI, MeCN, 50° C. to reflux, overnight, 15-53% for three steps.

As shown in Scheme 3, novel compounds 18, 20, 22 and 25 were prepared by introducing different 4-methylpiperazine bearing linkers into 10a. Alkylation of 10a with methyl 2-chloroacetate following the similar procedure to that of 11c afforded intermediate 16. Compound 18 may be obtained by hydrolysis of 16 to compound 17, followed by coupling of intermediate 17 with 1-methylpiperazine. Reaction of 10a with 2-chloroacetyl chloride in the presence of Et$_3$N affords intermediate 19. Compound 20 may be produced via a similar procedure to that of compound 12f (NY0244). The intermediates 21 and 23 were obtained by alkylation of 10a with 1-bromo-3-chloropropane and 4-chloro-1,1-diethoxybutane, respectively. Starting from intermediate 21, following a similar procedure to that of 12f (NY0244) produced the final compound 22 (NY0335). Deprotection of intermediate 23 using aqueous HCl resulted in compound 24. Compound 25 may be obtained by coupling of aldehyde 24 with 1-methylpiperazine under a standard reductamination condition.

Scheme 3. Syntheses of (R)—N-(1-(4-methoxyphenyl)ethyl)-N-(2-(4-methylpiperazin-1-yl)ethyl)-3,3-diphenyl-prop-2-en-1-amine Derivatives 18, 20, 22 and 25a

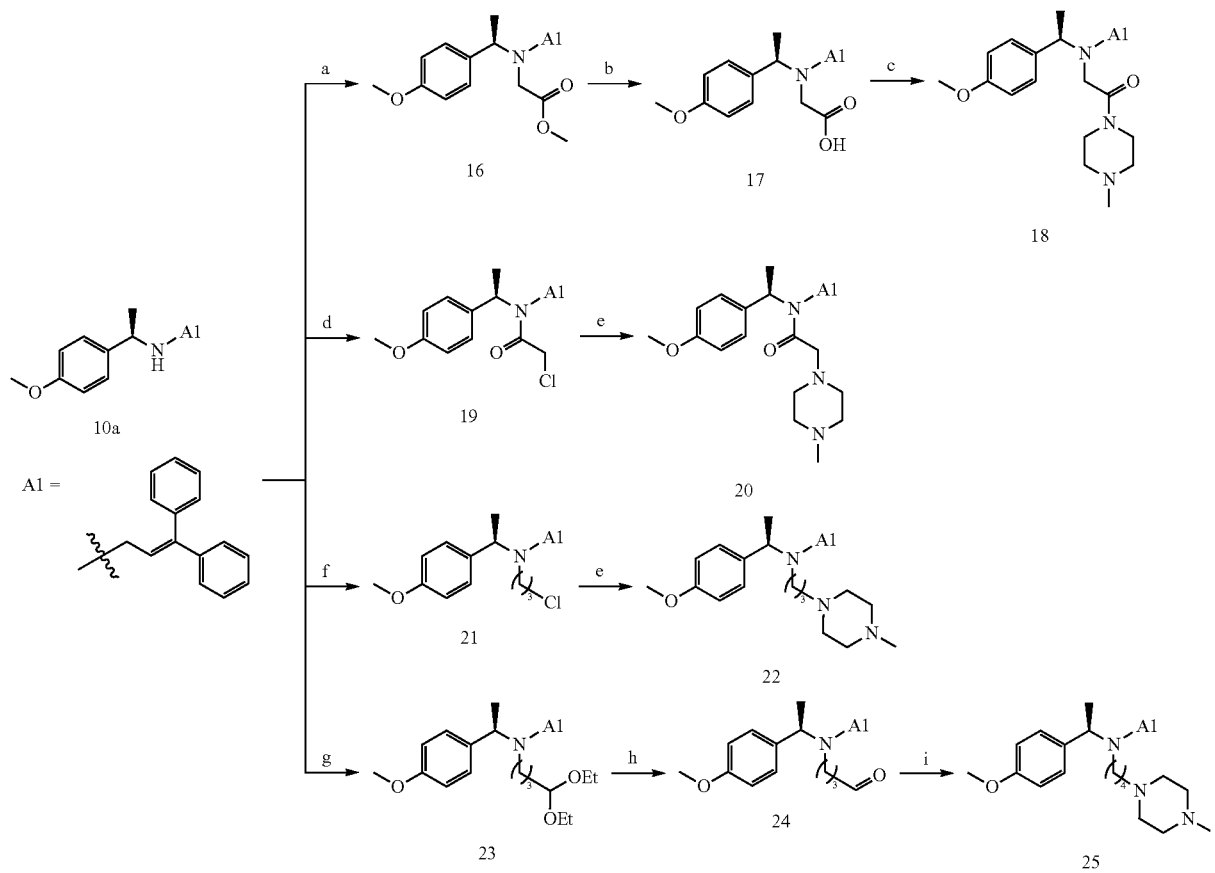

*Reagents and conditions: (a) methyl 2-chloroacetate, K₂CO₃, KI, MeCN, reflux, overnight, 92%; (b) i) LiOH, THF, rt, overnight; ii) 2 N HCl, 93%; (c) 1-methylpiperazine, EDCI, HOBt, DIPEA, CH₂Cl₂, rt, overnight, 83%; (d) 2-chloroacetyl chloride, Et₃N, rt, 2 h, 72%; (e) 1-methylpiperazine, K₂CO₃, KI, MeCN, 50° C. to reflux, overnight, 44% for 20, 60% for 22; (f) 1-bromo-3-chloropropane, DIPEA, DMF, 80° C., 16 h, 24%; (g) 4-chloro-1,1-diethoxybutane, K₂CO₃, KI, MeCN, reflux, 2 d, 43%; (h) 6 N HCl, 1,4-dioxane, 50° C., 2 h, 92%; (i) 1-methylpiperazine, NaBH(OAc)₃, DCE, rt, overnight, 52%.

(R)—N-(1-(4-Methoxyphenyl)ethyl)-3,3-diphenyl-prop-2-en-1-amine (NY0211)

A RB flask with activated 4 Å molecular sieves was charged with THF (10 mL), (R)-1-(4-methoxyphenyl)ethan-1-amine (755 mg, 5 mmol) and β-phenylcinnamylaldehyde (1040 mg, 5 mmol) under a nitrogen atmosphere. Ti(OiPr)₄ (1.7 g, 6 mmol) was added to the solution and the reaction mixture was stirred at 65° C. for 3 h, and then added the MeOH (10 mL). To the solution was added NaBH₄ (190 mg, 5 mmol) at 0° C. and reacted for 1 h. After the reaction completed, the residue was added with water (10 mL) and EtOAc (20 mL), then filtered through a pad of Celite, and the pad was washed with water and ethyl acetate. The filtrate was extracted with EtOAc (20 mL×3). The combined organic extracts were concentrated under reduced pressure. Purification by silica gel chromatography (Gradient: 3% to 5% MeOH in CH₂Cl₂) provided product NY0211 (1.56 g, 91%) as a light yellow oil. $^1$H NMR (300 MHz, CDCl₃) δ 7.33-7.25 (m, 3H), 7.24-7.18 (m, 5H), 7.17-7.11 (m, 2H), 7.11-7.04 (m, 2H), 6.83-6.76 (m, 2H), 6.17 (t, J=6.9 Hz, 1H), 3.75 (s, 3H), 3.70 (q, J=6.5 Hz, 1H), 3.17 (d, J=7.0 Hz, 2H), 2.06 (s, 1H), 1.29 (d, J=6.5 Hz, 3H). $^{13}$C NMR (75 MHz, CDCl₃) δ 158.59, 143.44, 142.25, 139.55, 137.18, 129.76, 128.14, 127.69, 127.61, 127.46, 127.26, 127.20, 113.83, 57.16, 55.28, 46.41, 24.15.

(R)—N-(2-Chloroethyl)-N-(1-(4-methoxyphenyl)ethyl)-3,3-diphenylprop-2-en-1-amine (NY0354)

A RB flask with magnetic stir bar was charged with 1,2-dichloroethane (20 mL), NY0211 (1.7 g, 5 mmol) and 45 wt. % 2-chloroacetaldehyde aqueous solution (2.8 mL, 20 mmol). The mixture solution was cooled to 0° C. with ice bath. To the stirred reaction solution under a nitrogen atmosphere was added NaBH(OAc)₃ (2.12 g, 10 mmol). The flask was sealed under nitrogen and stirred at 0° C. for 2 h. The reaction was worked up by the addition of sat. aq. NaHCO₃ and EtOAc extraction. The combined EtOAc extracts were washed with brine, dried over Na₂SO₄, filtered, and condensed by rotary evaporation. Purification by silica gel chromatography (Gradient: 10% to 20% ethyl acetate in petroleum ether) provided product NY0354 (1.6 g, 80%) as a light yellow oil. $^1$H NMR (300 MHz, CDCl$_3$) δ 7.43-7.22 (m, 10H), 7.16 (d, J=6.7 Hz, 2H), 6.86 (d, J=7.6 Hz, 2H), 6.21 (t, J=6.2 Hz, 1H), 3.96-3.86 (q, J=9.0 Hz, 1H), 3.83 (s, 3H), 3.46-3.33 (m, 2H), 3.31-3.15 (m, 2H), 2.79 (m, 2H), 1.30 (d, J=6.3 Hz, 3H). $^{13}$C NMR (75 MHz, CDCl$_3$) δ 158.49, 143.50, 142.19, 139.54, 135.91, 129.84, 128.61, 128.18, 127.58, 127.36, 127.27, 113.52, 59.11, 55.25, 52.17, 49.76, 42.54, 16.93.

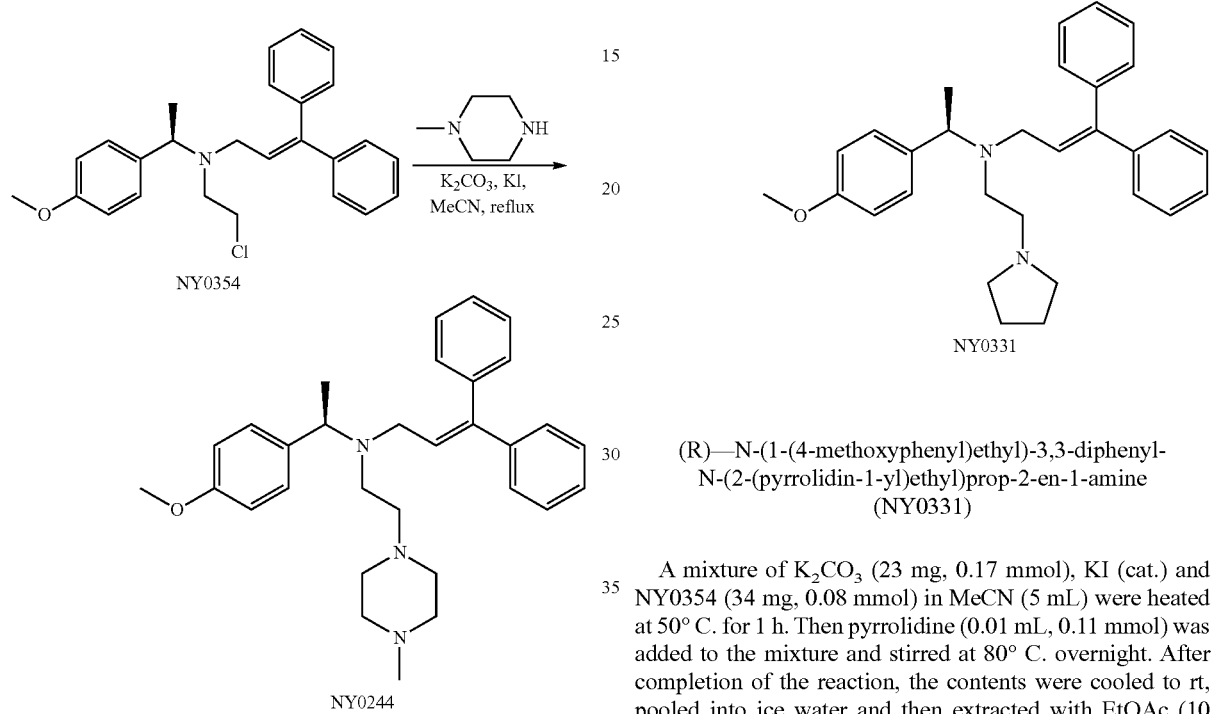

(R)—N-(1-(4-methoxyphenyl)ethyl)-N-(2-(4-methylpiperazin-1-yl)ethyl)-3,3-diphenylprop-2-en-1-amine (NY0244)

A mixture of NY0354 (405 mg, 1 mmol), K$_2$CO$_3$ (276 mg, 2 mmol), KI (cat.) and 1-methyl-piperazine (150 mg, 1.5 mmol) in MeCN (8 mL) were heated at 60° C. overnight. After completion of the reaction, the contents were cooled to room temperature, removed the solvent, diluted with water and then extracted with EtOAc (30 mL×3). The organic phase was washed with brine, dried over Na$_2$SO$_4$, and then concentrated under reduced pressure. The residue was purification by silica gel chromatography (Gradient: 1% to 5% MeOH in DCM) provided product NY0244 as a light yellow oil (351 mg, 75%). $^1$H NMR (300 MHz, CDCl$_3$) δ 7.40-7.22 (m, 10H), 7.15 (dd, J=7.6, 1.8 Hz, 2H), 6.86-6.79 (m, 2H), 6.22 (t, J=6.6 Hz, 1H), 3.89 (q, J=6.7 Hz, 1H), 3.80 (s, 3H), 3.33-3.16 (m, 2H), 2.71-2.29 (m, 12H), 2.28 (s, 3H), 1.27 (d, J=6.8 Hz, 3H). $^{13}$C NMR (75 MHz, CDCl$_3$) δ 158.29, 142.85, 142.45, 139.65, 136.26, 129.92, 128.66, 128.27, 128.10, 128.04, 127.37, 127.14, 127.08, 113.35, 58.98, 57.20, 55.22, 55.03, 53.52, 49.51, 47.28, 46.03, 16.96. HRMS (ESI) calcd. for C$_{31}$H$_{40}$N$_3$O 470.3171 (M+H)$^+$, found 470.3172.

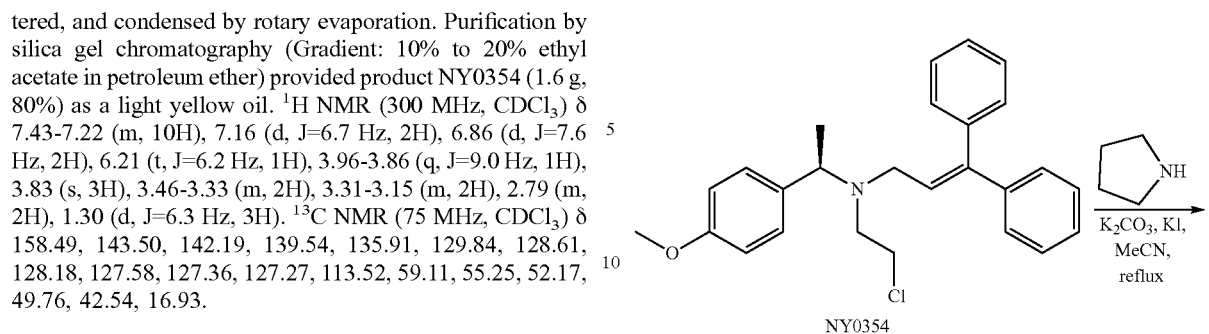

(R)—N-(1-(4-methoxyphenyl)ethyl)-3,3-diphenyl-N-(2-(pyrrolidin-1-yl)ethyl)prop-2-en-1-amine (NY0331)

A mixture of K$_2$CO$_3$ (23 mg, 0.17 mmol), KI (cat.) and NY0354 (34 mg, 0.08 mmol) in MeCN (5 mL) were heated at 50° C. for 1 h. Then pyrrolidine (0.01 mL, 0.11 mmol) was added to the mixture and stirred at 80° C. overnight. After completion of the reaction, the contents were cooled to rt, pooled into ice water and then extracted with EtOAc (10 mL×3). The combined organic phase was washed with brine, dried over Na$_2$SO$_4$, and then concentrated under reduced pressure. The residue was purified by preparative TLC plates (DCM/MeOH=15/1) to give NY0331 (21 mg, 59%) as a colorless oil. HPLC purity 97.2% (t$_R$=17.55 min). $^1$H NMR (300 MHz, CDCl$_3$) δ 7.43-7.20 (m, 10H), 7.15 (d, J=6.7 Hz, 2H), 6.82 (d, J=7.8 Hz, 2H), 6.22 (t, J=6.2 Hz, 1H), 3.88 (dd, J=13.2, 6.5 Hz, 1H), 3.81 (s, 3H), 3.35-3.14 (m, 2H), 2.73-2.48 (m, 4H), 2.47-2.35 (m, 4H), 1.84-1.64 (m, 4H), 1.28 (d, J=6.1 Hz, 3H). $^{13}$C NMR (75 MHz, CDCl$_3$) δ 158.30, 142.83, 142.50, 139.70, 136.31, 129.95, 128.68, 128.32, 128.09, 128.04, 127.39, 127.13, 127.06, 113.36, 59.04, 55.23, 55.15, 54.45, 49.59, 49.02, 23.36, 17.10. HRMS (ESI) calcd for C$_{30}$H$_{37}$N$_2$O 441.2906 (M+H)+, found 441.2906.

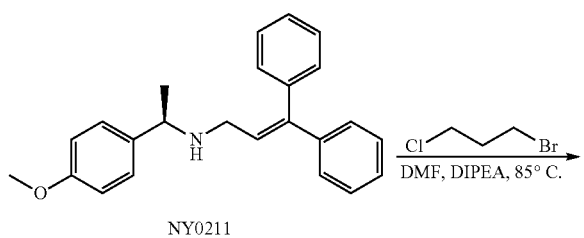

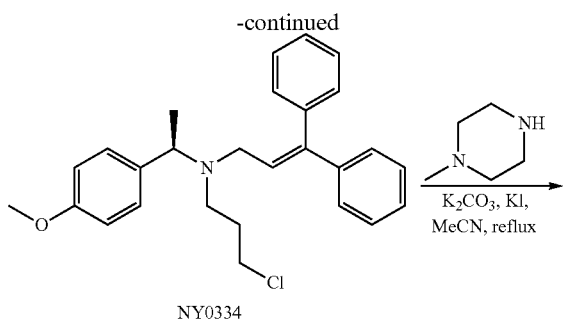

NY0334

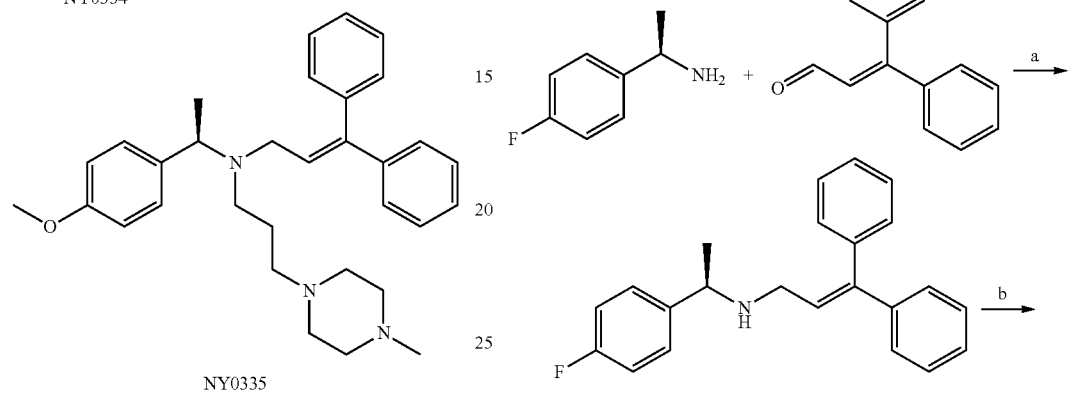

NY0335

(R)—N-(3-chloropropyl)-N-(1-(4-methoxyphenyl) ethyl)-3,3-diphenylprop-2-en-1-amine (NY0334)

A mixture of NY0211 (85 mg, 0.25 mmol), DIPEA (0.22 mL, 1.25 mmol), and 1-bromo-3-chloropropane (0.20 mL, 2.0 mmol) in DMF (4 mL) were heated at 80° C. for 16 h. After completion of the reaction, the contents were cooled to rt, pooled into ice water and then extracted with EtOAc. The combined organic phase was washed with brine, dried over $Na_2SO_4$, and then concentrated under reduced pressure. The residue was purified by preparative TLC plates (Hexane: EtOAc=10/1) to give NY0334 as yellow oil (25 mg, 24%). $^1$H NMR (300 MHz, CDCl$_3$) δ 7.28 (m, 10H), 6.85 (d, J=7.9 Hz, 2H), 6.21 (t, J=6.4 Hz, 1H), 3.95-3.85 (m, 1H), 3.82 (s, 3H), 3.66-3.48 (m, 2H), 3.28-3.10 (m, 2H), 2.70-2.44 (m, 2H), 1.91-1.70 (m, 2H), 1.29 (d, J=6.8 Hz, 3H). $^{13}$C NMR (75 MHz, CDCl$_3$) δ 158.36, 143.09, 142.40, 139.69, 135.97, 130.77, 129.89, 128.71, 128.66, 128.38, 128.15, 128.11, 127.37, 127.19, 127.16, 113.41, 58.42, 55.24, 48.83, 46.76, 43.34, 30.81, 16.42.

(R)—N-(1-(4-methoxyphenyl)ethyl)-N-(3-(4-methylpiperazin-1-yl)propyl)-3,3-diphenylprop-2-en-1-amine (NY0335)

A mixture of NY0334 (25 mg, 0.06), KI (cat.) and $K_2CO_3$ (15 mg, 0.11 mmol) in MeCN (5 mL) were heated at 50° C. for 1 h. Then 1-methylpiperazine (0.01 mL, 0.09 mmol) was added to the mixture and stirred at 80° C. overnight. After completion of the reaction, the contents were cooled to rt, pooled into ice water and then extracted with EtOAc (10 mL×3). The combined organic phase was washed with brine, dried over $Na_2SO_4$, and then concentrated under reduced pressure. The residue was purified by preparative TLC plates (DCM/MeOH=15/1) to give NY0335 (17 mg, 60%) as colorless oil. HPLC purity 95.2% ($t_R$=16.49 min). $^1$H NMR (300 MHz, Chloroform-d) δ 7.40-7.19 (m, 10H), 7.14 (d, J=6.8 Hz, 2H), 6.82 (d, J=8.5 Hz, 2H), 6.23-6.16 (m, 1H), 3.85 (q, J=6.2 Hz, 1H), 3.80 (s, 3H), 3.19 (m, 2H), 2.65-2.21 (m, 12H), 2.28 (s, 3H), 1.61-1.45 (m, 2H), 1.24 (d, J=6.6 Hz, 3H). $^{13}$C NMR (75 MHz, CDCl$_3$) δ 158.24, 142.72, 142.49, 139.74, 136.51, 129.90, 128.67, 128.50, 128.09, 128.04, 127.34, 127.09, 127.05, 113.33, 58.44, 56.58, 55.21, 55.14, 53.19, 48.72, 47.76, 46.05, 24.71, 16.86. HRMS (ESI) calcd. for $C_{32}H_{42}N_3O$ 484.3328 (M+H)+, found 484.3325.

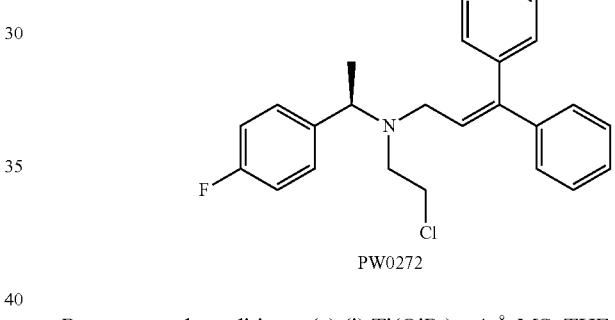

PW0270

Reagents and conditions: (a) (i) Ti(OiPr)$_4$, 4 Å MS, THF, 65° C., 2 h; ii) NaBH$_4$, MeOH/THF. 0° C., 30 min (b) chloroacetaldehyde, NaBH(OAc)$_3$, ClCH$_2$CH$_2$Cl, 0° C., 2 h

R)—N-(1-(4-Fluorophenyl)ethyl)-3,3-diphenylprop-2-en-1-amine (PW0270)

A RB flask with activated 4 Å molecular sieves was charged with THF (10 mL), (R)-1-(4-fluorophenyl)ethan-1-amine (695 mg, 5 mmol) and/3-phenylcinnamylaldehyde (1040 mg, 5 mmol) under a nitrogen atmosphere. Ti(OiPr)$_4$ (1.7 g, 6 mmol) was added to the solution and the reaction mixture was stirred at 65° C. for 3 h, and then added the MeOH (10 mL). To the solution was added NaBH$_4$ (190 mg, 5 mmol) at 0° C. and reacted for 1 h. After the reaction completed, the residue was added with water (10 mL) and EtOAc (20 mL), then filtered through a pad of Celite, and the pad was washed with water and ethyl acetate. The filtrate was extracted with EtOAc (20 mL×3). The combined organic extracts were concentrated under reduced pressure. Purification by silica gel chromatography (Gradient: 3% to 5% MeOH in CH$_2$Cl$_2$) provided product PW0270 (1.44 g, 87%) as a light yellow oil. $^1$H NMR (300 MHz, Chloroform-d) δ 7.40-7.19 (m, 10H), 7.16-7.09 (m, 2H), 7.03-6.93 (m, 2H), 6.19 (t, J=7.0 Hz, 1H), 3.77 (q, J=6.6 Hz, 1H), 3.19 (d, J=7.0 Hz, 2H), 1.32 (d, J=6.6 Hz, 3H).

(R)—N-(2-Chloroethyl)-N-(1-(4-fluorophenyl)ethyl)-3,3-diphenylprop-2-en-1-amine (PW0272)

A RB flask with magnetic stir bar was charged with 1,2-dichloroethane (20 mL), PW0270 (1.66 g, 5 mmol) and 45 wt. % 2-chloroacetaldehyde aqueous solution (2.8 mL, 20 mmol). The mixture solution was cooled to 0° C. with ice bath. To the stirred reaction solution under a nitrogen atmosphere was added NaBH(OAc)$_3$ (2.12 g, 10 mmol). The flask was sealed under nitrogen and stirred at 0° C. for 2 h. The reaction was worked up by the addition of sat. aq. NaHCO$_3$ and EtOAc extraction. The combined EtOAc extracts were washed with brine, dried over Na$_2$SO$_4$, filtered, and condensed by rotary evaporation. Purification by silica gel chromatography (Gradient: 10% to 20% ethyl acetate in petroleum ether) provided product PW0272 (1.47 g, 75%) as a light yellow oil. $^1$H NMR (300 MHz, Chloroform-d) δ 7.45-7.24 (m, 10H), 7.18-7.09 (m, 2H), 7.05-6.95 (m, 2H), 6.19 (t, J=6.7 Hz, 1H), 3.92 (q, J=6.7 Hz, 1H), 3.47-3.33 (m, 2H), 3.33-3.17 (m, 2H), 2.79 (ddd, J=7.8, 6.5, 3.3 Hz, 2H), 1.29 (d, J=6.7 Hz, 3H).

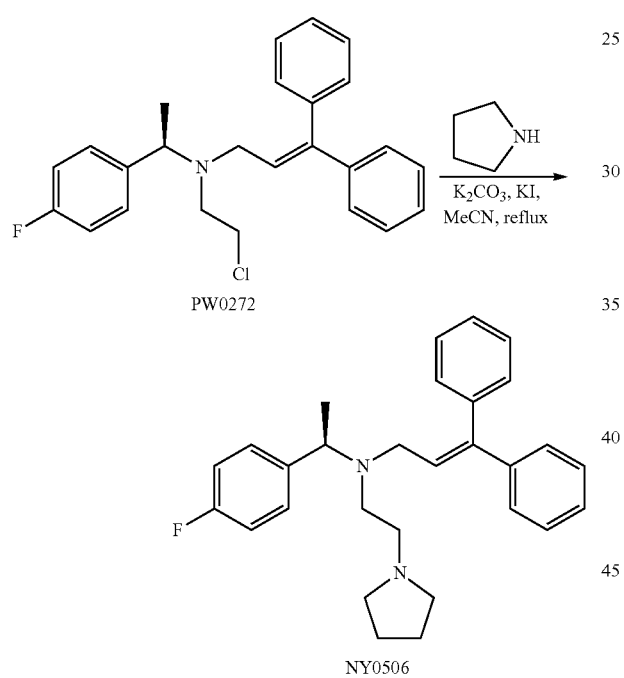

(R)—N-(1-(4-fluorophenyl)ethyl)-3,3-diphenyl-N-(2-(pyrrolidin-1-yl)ethyl)prop-2-en-1-amine (NY0506)

A mixture of PW0272 (786 mg, 2 mmol), K$_2$CO$_3$ (552 mg, 4 mmol), KI (cat.) and pyrrolidine (284 mg, 2 mmol) in MeCN (20 mL) were heated at 80° C. overnight. After completion of the reaction, the contents were cooled to room temperature, removed the solvent, diluted with water and then extracted with EtOAc (30 mL×3). The organic phase was washed with brine, dried over Na$_2$SO$_4$, and then concentrated under reduced pressure. The residue was purification by silica gel chromatography (Gradient: 1% to 5% MeOH in DCM) provided product NY0506 as a light yellow oil (790 mg, 92%). HPLC purity 97.6% (t$_R$=17.89 min). $^1$H NMR (300 MHz, CDCl$_3$) δ 7.39-7.23 (m, 10H), 7.18-7.11 (m, 2H), 7.01-6.93 (m, 2H), 6.22 (t, J=6.6 Hz, 1H), 3.91 (q, J=6.7 Hz, 1H), 3.33-3.16 (m, 2H), 2.71-2.40 (m, 8H), 1.86-1.69 (m, 4H), 1.28 (d, J=6.7 Hz, 3H). $^{13}$C NMR (75 MHz, CDCl$_3$) δ 161.66 (d, J=242.9 Hz), 143.18, 142.38, 139.97, 139.93, 139.59, 129.90, 129.14, 129.03, 128.14, 128.09, 127.84, 127.38, 127.22, 127.18, 114.88, 114.60, 58.97, 55.07, 54.41, 49.56, 48.79, 23.35, 16.93. HRMS (ESI) calcd. for C$_{29}$H$_{34}$N$_2$F 429.2706 (M+H)+, found 429.2694.

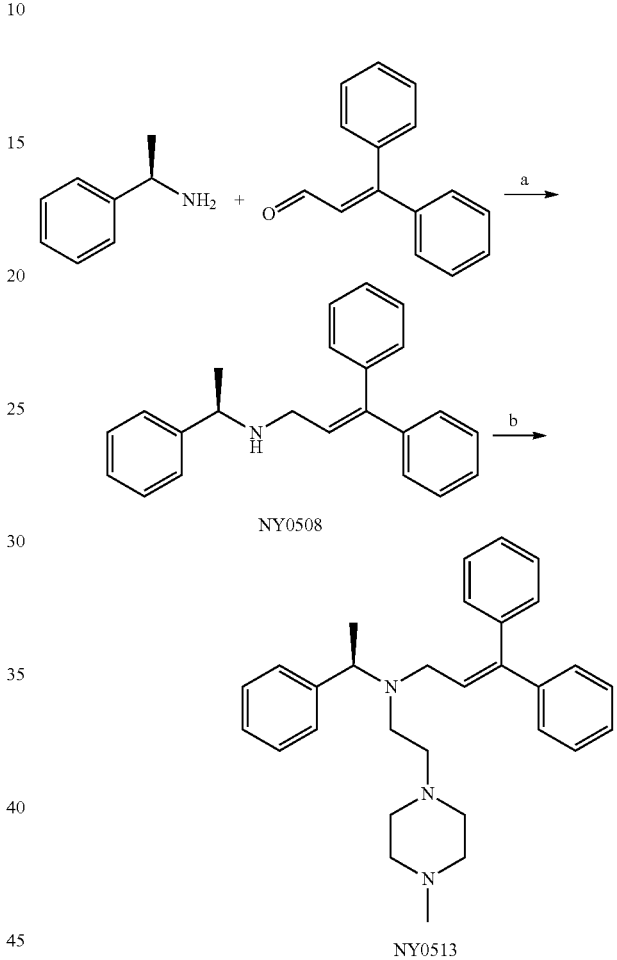

Reagents and conditions: (a) (i) Ti(OiPr)$_4$, 4 Å MS, THF, 65° C., 2 h; (ii) NaBH$_4$, MeOH/THF. 0° C., 30 min (b) (i) chloroacetaldehyde, NaBH(OAc)$_3$, ClCH$_2$CH$_2$Cl, 0° C., 2 h; (ii) K$_2$CO$_3$, KI, 1-methyl-piperazine, MeCN, 60° C., 12 h.

(R)-3,3-Diphenyl-N-(1-phenylethyl)prop-2-en-1-amine (NY0211)

A RB flask with activated 4 Å molecular sieves was charged with THF (10 mL), (R)-1-phenylethan-1-amine (605 mg, 5 mmol) and β-phenylcinnamylaldehyde (1040 mg, 5 mmol) under a nitrogen atmosphere. Ti(OiPr)$_4$ (1.7 g, 6 mmol) was added to the solution and the reaction mixture was stirred at 65° C. for 3 h, and then added the MeOH (10 mL). To the solution was added NaBH$_4$ (190 mg, 5 mmol) at 0° C. and reacted for 1 h. After the reaction completed, the residue was added with water (10 mL) and EtOAc (20 mL), then filtered through a pad of Celite, and the pad was washed with water and ethyl acetate. The filtrate was extracted with EtOAc (20 mL×3). The combined organic extracts were concentrated under reduced pressure. Purification by silica gel chromatography (Gradient: 3% to 5% MeOH in $CH_2Cl_2$) provided product NY0508 (1.4 g, 89%) as a light yellow oil. $^1$H NMR (300 MHz, Chloroform-d) δ 7.37-7.28 (m, 15H), 6.25 (t, J=6.9 Hz, 1H), 3.82 (d, J=6.6 Hz, 1H), 3.26 (d, J=6.9 Hz, 2H), 1.39 (d, J=6.6 Hz, 3H).

(R)—N-(2-(4-methylpiperazin-1-yl)ethyl)-3,3-diphenyl-N-(1-phenylethyl)prop-2-en-1-amine (NY0513)

A RB flask with magnetic stir bar was charged with 1,2-dichloroethane (5 mL), NY0508 (313 mg, 1 mmol) and 45 wt. % 2-chloroacetaldehyde aqueous solution (0.7 mL, 4 mmol). The mixture solution was cooled to 0° C. with ice bath. To the stirred reaction solution under a nitrogen atmosphere was added $NaBH(OAc)_3$ (424 mg, 2 mmol). The flask was sealed under nitrogen and stirred at 0° C. for 2 h. The reaction was worked up by the addition of sat. aq. $NaHCO_3$ and EtOAc extraction. The combined EtOAc extracts were washed with brine, dried over $Na_2SO_4$, filtered, and condensed by rotary evaporation. The residue and a mixture of $K_2CO_3$ (276 mg, 2 mmol), KI (cat.) and 1-methyl-piperazine (150 mg, 1.5 mmol) in MeCN (8 mL) were heated at 60° C. overnight. After completion of the reaction, the contents were cooled to room temperature, removed the solvent, diluted with water and then extracted with EtOAc (30 mL×3). The organic phase was washed with brine, dried over $Na_2SO_4$, and then concentrated under reduced pressure. The residue was purification by silica gel chromatography (Gradient: 1% to 5% MeOH in DCM) provided product NY0513 as a light yellow oil (251 mg, 57% for two steps). HPLC purity 99.3% ($t_R$=16.83 min). $^1$H NMR (300 MHz, $CDCl_3$) δ 7.39-7.22 (m, 13H), 7.18-7.13 (m, 2H), 6.23 (t, J=6.6 Hz, 1H), 3.93 (d, J=6.7 Hz, 1H), 3.27 (t, J=6.3 Hz, 2H), 2.65-2.57 (m, 2H), 2.56-2.30 (m, 10H), 2.28 (s, 3H), 1.30 (d, J=6.7 Hz, 3H). $^{13}$C NMR (75 MHz, $CDCl_3$) δ 144.36, 143.00, 142.45, 139.65, 129.93, 128.13, 128.11, 128.08, 128.06, 127.67, 127.39, 127.18, 127.13, 126.66, 59.72, 57.14, 55.02, 53.50, 49.58, 47.36, 46.02, 16.99. HRMS (ESI) calcd for $C_{30}H_{38}N_3$ 440.3066 (M+H)$^+$, found 440.3066.

Reagents and conditions: (a) $K_2CO_3$, KI, MeCN, reflux, 24 h, 75%. (b) 5-(4-methoxyphenyl)isoxazole-3-carboxylic acid, HBTU, HOBt, DIPEA, $CH_2Cl_2$, r.t. 12 h, 67%.

(R)-1-(4-Fluorophenyl)-N-(2-(pyrrolidin-1-yl)ethyl) ethan-1-amine (PW0316)

A mixture of $K_2CO_3$ (276 mg, 2 mmol), KI (cat.) and 1-(2-chloroethyl)pyrrolidine hydrochloride (171 mg, 1 mmol) in MeCN (4 mL) were heated at 50° C. for 1 h. Then (R)-1-(4-fluorophenyl)ethan-1-amine (278 mg, 2 mmol) was added to the mixture and stirred at 80° C. overnight. After completion of the reaction, the reaction mixture was concentrated under reduced pressure. Purification by silica gel chromatography (Gradient: 5% to 10% MeOH in DCM) provided product PW0316 (177 mg, 75%) as a light yellow oil. $^1$H NMR (300 MHz, Chloroform-d) δ 7.32-7.28 (m, 2H), 7.06-6.99 (m, 2H), 3.76 (q, J=6.6 Hz, 1H), 2.57 (ddd, J=9.9, 3.9, 1.8 Hz, 4H), 2.49-2.39 (m, 4H), 1.76 (td, J=4.3, 2.0 Hz, 4H), 1.35 (d, J=6.7 Hz, 3H).

(R)—N-(1-(4-Fluorophenyl)ethyl)-5-(4-methoxyphenyl)-N-(2-(pyrrolidin-1-yl)ethyl)isoxazole-3-carboxamide (PW0323)

PW0316 (50 mg, 0.21 mmol) and the 5-(4-methoxyphenyl)isoxazole-3-carboxylic acid (46 mg, 0.21 mmol) were dissolved in 5 mL DCM and the mixture solution was cooled to 0° C. with ice bath. HOBt (28 mg, 0.21 mmol), HBTU (159 mg, 0.42 mmol) and DIPEA (0.08 mL, 0.68 mmol) were added to the solution at 0° C. Then removed the ice bath, the mixture solution was stirred at room temperature overnight. After the reaction completed (detected by TLC). The reaction was worked up by the addition of water and EtOAc extraction. The combined EtOAc extracts were washed with brine, dried $Na_2SO_4$, filtered, and condensed by rotary evaporation to yield a yellow oil. This material was further purified by preparative TLC plates using $CH_2Cl_2$/MeOH=50:1 as the eluent to yield PW0323 as a light yellow oil (61 mg, 67%). $^1$H NMR (300 MHz, Chloroform-d) δ 7.75 (d, J=8.4 Hz, 2H), 7.49-7.32 (m, 2H), 7.12-6.96 (m, 4H), 6.74 (d, J=11.4 Hz, 1H), 5.95 (dd, J=45.2, 7.2 Hz, 1H), 3.88 (s, 3H), 3.69-3.32 (m, 2H), 2.80-2.09 (m, 6H), 1.84-1.54 (m, 7H). $^{13}$C NMR (75 MHz, $CDCl_3$) δ 163.89, 161.47, 161.20, 160.61, 159.60, 129.23, 127.57, 119.53, 115.54, 115.26, 114.53, 99.14, 55.41, 54.16, 53.83, 42.04, 23.39, 18.00.

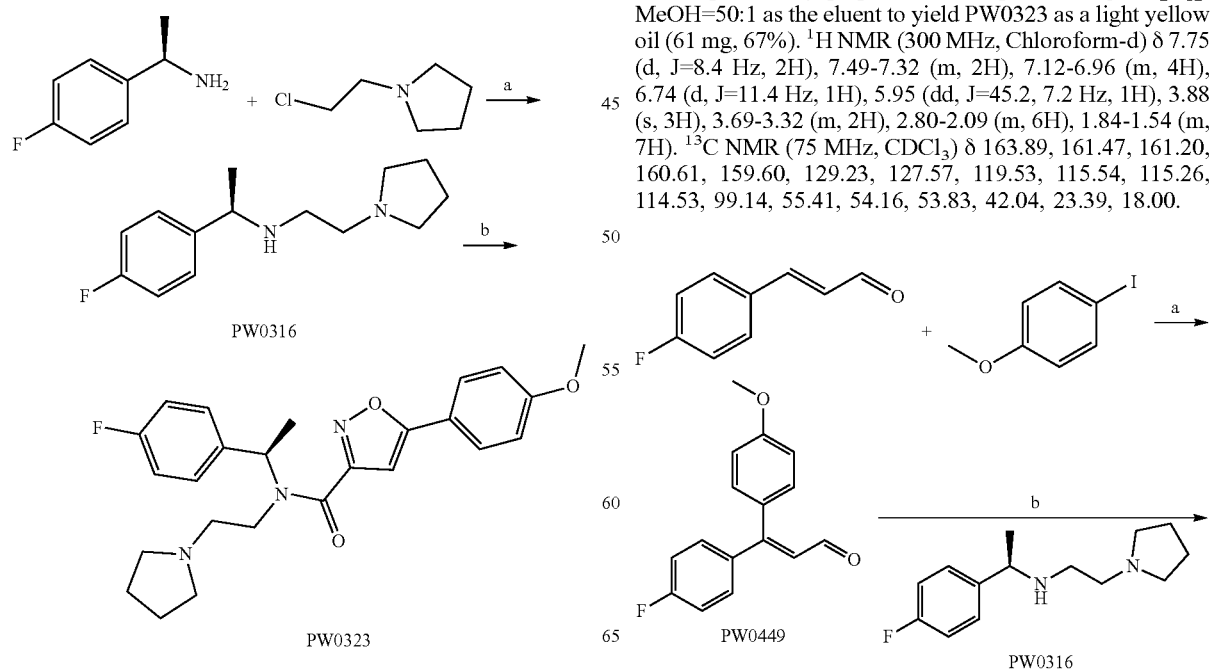

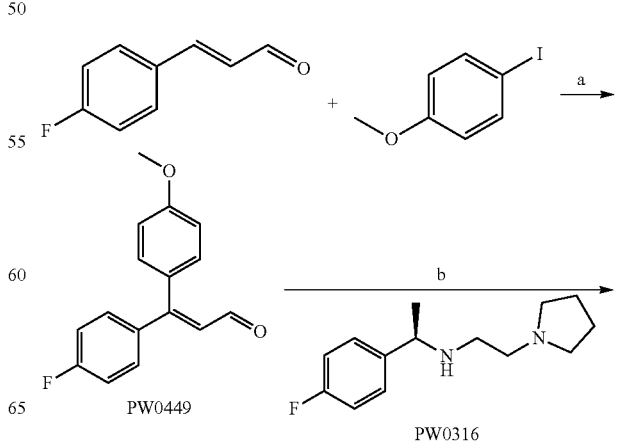

-continued

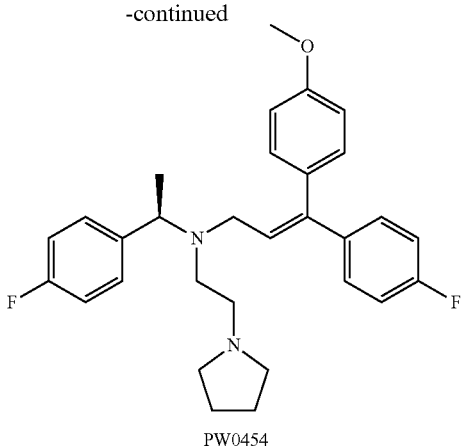

PW0454

Reagents and conditions: (a) NaOAc, TBAI, Pd(OAc)$_2$, DMF, 120° C., 24 h; (b) NaBH(OAc)$_3$, C$_1$CH$_2$CH$_2$Cl, 0° C., 12 h.

(E)-3-(4-Fluorophenyl)-3-(4-methoxyphenyl)acrylaldehyde (PW0449)

A mixture of NaOAc (246 mg, 3 mmol), (E)-3-(4-fluorophenyl)acrylaldehyde (300 mg, 2 mmol), 1-iodo-4-methoxybenzene (666 mg, 3 mmol) and TBAI (738 mg, 2 mmol) in dry DMF (2 mL) was heated to 120° C. Pd(OAc)$_2$ was dissolved in DMF (2 mL). After the catalyst had dissolved completely, this solution was added to the reaction mixture. After heated at 120° C. for 24 hours, the reaction was cooled to room temperature and poured in water, and then extracted with EtOAc (10 mL×3). The organic phase was washed with brine, dried over Na$_2$SO$_4$, and then concentrated under reduced pressure. The residue was purification by silica gel chromatography (Gradient: 1% to 5% EtOAc in hexane) provided product PW0449 as a light yellow oil (272 mg, 53%). $^1$H NMR (300 MHz, Chloroform-d) δ 9.47 (d, J=8.1 Hz, 1H), 7.40-6.89 (m, 8H), 6.57 (d, J=8.1 Hz, 1H), 3.86 (s, 3H).

(R,E)-3-(4-fluorophenyl)-N-(1-(4-fluorophenyl) ethyl)-3-(4-methoxyphenyl)-N-(2-(pyrrolidin-1-yl) ethyl)prop-2-en-1-amine (PW0454)

A RB flask with magnetic stir bar was charged with 1,2-dichloroethane (2 mL), phosphotungstic acid hydrate (cat.), PW0449 (51 mg, 0.2 mmol) and PW0316 (47 mg, 0.2 mmol). To the stirred reaction solution under a nitrogen atmosphere was added NaBH(OAc)$_3$ (64 mg, 0.3 mmol). The flask was sealed under nitrogen and stirred at room temperature for 24 hours. The reaction was worked up by the addition of sat. aq. NaHCO$_3$ and EtOAc. The combined EtOAc extracts were washed with brine, dried over NaSO$_4$, filtered, and condensed by rotary evaporation to yield an oil. The residue was purification by silica gel chromatography (Gradient: 10% to 20% EtOAc in hexane) provided product NY0454 (48 mg, 51%) as a light yellow oil. $^1$H NMR (300 MHz, Chloroform-d) δ 7.25-6.76 (m, 12H), 6.11 (dt, J=9.1, 6.6 Hz, 1H), 3.95-3.75 (m, 4H), 3.22 (dt, J=13.7, 6.8 Hz, 2H), 2.49 (d, J=5.7 Hz, 8H), 1.78 (q, J=3.3 Hz, 4H), 1.28 (d, J=2.7 Hz, 3H). $^{13}$C NMR (75 MHz, CDCl$_3$) δ 139.91, 139.01, 134.83, 131.00, 129.15, 129.04, 128.42, 126.24, 115.12, 114.89, 114.61, 113.56, 113.51, 58.97, 55.26, 55.01, 54.39, 49.53, 23.33.

(R)—N-(1-(4-Methoxyphenyl)ethyl)-3,3-diphenyl-prop-2-en-1-amine (10a)

A RB flask with activated 4 Å molecular sieves and dried anhydrous Na$_2$SO$_4$ was charged with THF (8 mL), (R)-1-(4-methoxy-phenyl)-ethylamine 9a (360 mg, 2.4 mmol) and β-phenylcinnamylaldehyde (500 mg, 2.4 mmol) under a nitrogen atmosphere. The reaction mixture was stirred at rt for 48 h, and then removed the solvent and refilled with MeOH (10 mL). To the solution was added NaBH$_4$ (140 mg, 3.7 mmol) at 0° C. and reacted for 2 h. After removing the solvent, the residue was diluted with water (10 mL) and extracted with EtOAc (20 mL×3). The combined organic phase was acidized with 4 N aq. HCl to pH<3 and extracted with Et$_2$O (15 mL×3). The water phase was separated and basified with 10 N aq. NaOH to pH>9, and then extracted with EA (15 mL×3). The combined EtOAc extracts were washed with brine, dried with NaSO$_4$, filtered, and condensed by rotary evaporation to yield 10a as a colorless oil used directly for next step (560 mg, 68%). $^1$H NMR (300 MHz, CDCl$_3$) δ 7.33-7.25 (m, 3H), 7.24-7.18 (m, 5H), 7.17-7.11 (m, 2H), 7.11-7.04 (m, 2H), 6.83-6.76 (m, 2H), 6.17 (t, J=6.9 Hz, 1H), 3.75 (s, 3H), 3.70 (q, J=6.5 Hz, 1H), 3.17 (d, J=7.0 Hz, 2H), 2.06 (s, 1H), 1.29 (d, J=6.5 Hz, 3H). $^{13}$C NMR (75 MHz, CDCl$_3$) δ 158.6, 143.4, 142.3, 139.6, 137.2, 129.8, 128.1, 127.7, 127.6, 127.5, 127.3, 127.2, 113.8, 57.2, 55.3, 46.4, 24.2.

(R)—N-(1-(4-Methoxyphenyl)ethyl)-N-methyl-3,3-diphenylprop-2-en-1-amine (11a)

To a solution of 10a (34.3 mg, 0.1 mmol) in MeCN (2 mL) was added K$_2$CO$_3$ (27.6 mg, 0.2 mmol) and iodomethane (21.3 mg, 0.15 mmol). Then the mixture was stirred at reflux overnight. After removing the solvent, the residue was diluted with water (8 mL) and extracted with EtOAc (15 mL×3). The combined EtOAc extracts were washed with brine, dried over NaSO$_4$, filtered, and condensed by rotary evaporation to yield an oil. This material was further purified by preparative TLC plates using EtOAc/hexane as the eluant to yield a colorless oil 11a (12 mg, 34%). $^1$H NMR (300 MHz, CDCl$_3$) δ 7.40-7.19 (m, 10H), 7.15 (dd, J=7.7, 1.8 Hz, 2H), 6.88-6.79 (m, 2H), 6.25 (t, J=6.7 Hz, 1H), 3.82 (s, 3H), 3.55 (q, J=6.7 Hz, 1H), 3.18 (dd, J=14.5, 6.4 Hz, 1H), 3.02 (dd, J=14.4, 7.1 Hz, 1H), 2.21 (s, 3H), 1.31 (d, J=6.7 Hz, 3H). $^{13}$C NMR (75 MHz, CDCl$_3$) δ 158.4, 143.2, 142.4, 139.7, 136.0, 129.9, 128.6, 128.1, 128.0, 127.6, 127.3, 127.1 (2C), 113.5, 62.2, 55.2, 53.4, 38.8, 18.8. HRMS (ESI) calcd for C$_{25}$H$_{28}$NO 358.2171 (M+H)+, found 358.2169.

(R)—N-Ethyl-N-(1-(4-methoxyphenyl)ethyl)-3,3-diphenylprop-2-en-1-amine (11b)

To a solution of 10a (20 mg, 0.04 mmol) and acetaldehyde (0.01 mL, 0.20 mmol) in 1,2-dichloroethane (4 mL) was added acetic acid (cat.). 10 min later, NaBH(OAc)$_3$ (20 mg, 0.09 mmol) was added to the stirred reaction solution. The flask was stirred at rt for 24 h. The reaction was worked up by the addition of sat. aq. NaHCO$_3$ and EtOAc. The combined EtOAc extracts were washed with brine, dried over Na$_2$SO$_4$, filtered, and condensed under pressure. The residue was further purified by preparative TLC plates using DCM/MeOH (25/1) as the eluant to yield 11b (17 mg, 80%) as a yellow oil. $^1$H NMR (300 MHz, CDCl$_3$) δ 7.43-7.33 (m, 3H), 7.31-7.23 (m, 7H), 7.19-7.12 (m, 2H), 6.88-6.81 (m, 2H), 6.24 (t, J=6.6 Hz, 1H), 3.89-3.78 (m, 1H), 3.82 (s, 3H), 3.28-3.13 (m, 2H), 2.66-2.47 (m, 2H), 1.28 (d, J=6.7 Hz, 3H), 0.94 (t, J=7.1 Hz, 3H). $^{13}$C NMR (75 MHz, CDCl$_3$) δ 158.3, 142.5, 139.8, 129.9, 128.6, 128.1, 128.1 (2C), 127.3, 127.1, 127.0, 113.4, 58.6, 55.2, 48.3, 43.6, 17.8, 12.1. HRMS (ESI) calcd for C$_{26}$H$_{30}$NO 372.2322 (M+H)+, found 372.2315.

(R)—N-Allyl-N-(1-(4-methoxyphenyl)ethyl)-3,3-diphenylprop-2-en-1-amine (11c)

Compound 11c (29 mg, 77%) was prepared by a similar procedure to that of compound 11a from 3-bromo-propene. The title compound was obtained as a colorless oil. $^1$H NMR (300 MHz, CDCl$_3$) δ 7.42-7.23 (m, 10H), 7.17 (dd, J=7.7, 1.8 Hz, 2H), 6.89-6.81 (m, 2H), 6.24 (t, J=6.6 Hz, 1H), 5.83 (m, 1H), 5.18-5.04 (m, 2H), 3.91 (q, J=6.7 Hz, 1H), 3.83 (s, 3H), 3.22 (t, J=6.5 Hz, 2H), 3.09 (dd, J=12.6, 6.3 Hz, 2H), 1.29 (d, J=6.7 Hz, 3H). $^{13}$C NMR (75 MHz, CDCl$_3$) 158.3, 142.8, 142.5, 139.8, 136.7, 136.1, 129.9, 128.7, 128.5, 128.1, 128.0, 127.4, 127.1 (2C), 116.7, 113.4, 58.1, 55.2, 53.0, 48.6, 16.9. HRMS (ESI) calcd for C$_{27}$H$_{30}$NO 384.2327 (M+H)+, found 384.2328.

(R)—N-(2-Chloroethyl)-N-(1-(4-methoxyphenyl)ethyl)-3,3-diphenylprop-2-en-1-amine (11d). Compound 11d (365 mg, 90%) was prepared by a similar procedure to that of compound 11b from 45 wt. % 2-chloroacetaldehyde aqueous solution. The title compound was obtained as a colorless oil. $^1$H NMR (300 MHz, CDCl$_3$) δ 7.43-7.22 (m, 10H), 7.16 (d, J=6.7 Hz, 2H), 6.86 (d, J=7.6 Hz, 2H), 6.21 (t, J=6.2 Hz, 1H), 3.96-3.86 (q, J=9.0 Hz, 1H), 3.83 (s, 3H), 3.46-3.33 (m, 2H), 3.31-3.15 (m, 2H), 2.79 (m, 2H), 1.30 (d, J=6.3 Hz, 3H). $^{13}$C NMR (75 MHz, CDCl$_3$) δ 158.5, 143.50, 142.2, 139.5, 135.9, 129.9, 128.6, 128.2, 127.6, 127.4, 127.3, 113.5, 59.1, 55.3, 52.2, 49.8, 42.5, 16.9. HRMS (ESI) calcd for C$_{26}$H$_{29}$C$_1$NO 406.1938 (M+H)+, found 406.1932.

(R)-2-((3,3-Diphenylallyl)(1-(4-methoxyphenyl)ethyl)amino)ethanol (11e)

Compound 11e (14 mg, 18%) was prepared by a similar procedure to that of compound 11a from 2-bromoethanol with DIPEA as the base. The title compound was obtained as a colorless oil. $^1$H NMR (300 MHz, CDCl$_3$) δ 7.42-7.34 (m, 3H), 7.32-7.24 (m, 5H), 7.17 (t, J=7.6 Hz, 4H), 6.83 (d, J=8.6 Hz, 2H), 6.18 (t, J=6.7 Hz, 1H), 3.99 (q, J=6.9 Hz, 1H), 3.81 (s, 3H), 3.46 (q, J=5.4 Hz, 2H), 3.35-3.14 (m, 2H), 2.70-2.59 (m, 1H), 2.56-2.47 (m, 1H), 2.39 (s, 1H), 1.30 (d, J=6.9 Hz, 4H). $^{13}$C NMR (75 MHz, CDCl$_3$) δ 158.5, 143.8, 142.2, 139.5, 134.7, 129.8, 128.8, 128.2, 127.4, 127.3, 113.6, 58.4, 58.1, 55.2, 50.7, 48.6, 15.8. HRMS (ESI) calcd for C$_{26}$H$_{30}$NO$_2$ 388.2277 (M+H)+, found 388.2273.

(R)—N-(2-Fluoroethyl)-N-(1-(4-methoxyphenyl)ethyl)-3,3-diphenylprop-2-en-1-amine (11f)

Compound 11e (27 mg, 70%) was prepared by a similar procedure to that of compound 11a from 1-bromo-2-fluoroethane with DIPEA as the base. The title compound was obtained as a colorless oil. $^1$H NMR (300 MHz, CDCl$_3$) δ 7.43-7.26 (m, 10H), 7.17 (d, J=7.1 Hz, 2H), 6.86 (d, J=7.7 Hz, 2H), 6.25 (t, J=6.6 Hz, 1H), 4.45 (t, J=5.5 Hz, 1H), 4.29 (t, J=5.5 Hz, 1H), 3.95 (q, J=6.3 Hz, 1H), 3.83 (s, 3H), 3.30 (t, J=6.5 Hz, 2H), 2.90-2.62 (m, 2H), 1.30 (d, J=6.7 Hz, 3H). $^{13}$C NMR (75 MHz, CDCl$_3$) δ 158.4, 143.3, 142.3, 139.6, 135.9, 129.9, 128.7, 128.2 (2C), 128.1, 127.9, 127.4, 127.2 (2C), 113.6, 83.1 (J=166.5 Hz), 59.0, 55.2, 49.9, 49.7 (J=21 Hz), 16.7. HRMS (ESI) calcd for C$_{26}$H$_{29}$NFO 390.2233 (M+H)+, found 390.2235.

(R)—N$^1$-(3,3-Diphenylallyl)-N$^1$-(1-(4-methoxyphenyl)ethyl)-N$^2$,N$^2$-dimethylethane-1,2-diamine (12a)

A mixture of K$_2$CO$_3$ (23 mg, 0.17 mmol), KI (cat.) and 11d (34 mg, 0.08 mmol) in MeCN (5 mL) was heated at reflux for 1 h. Then dimethylamine (0.01 mL, 0.17 mmol) was added to the mixture and stirred at reflux overnight. After completion of the reaction, the contents were cooled to rt, poured into ice water and then extracted with EtOAc. The combined organic phase was washed with brine, dried over Na$_2$SO$_4$, and then concentrated under reduced pressure. The residue was purified by preparative TLC plates (DCM/MeOH=15/1) to give 12a (12 mg, 37%) as a colorless oil. $^1$H NMR (300 MHz, CDCl$_3$) δ 7.41-7.32 (m, 3H), 7.31-7.22 (m, 7H), 7.15 (dd, J=7.7, 1.7 Hz, 2H), 6.87-6.79 (m, 2H), 6.23 (t, J=6.6 Hz, 1H), 3.87 (q, J=6.7 Hz, 1H), 3.81 (s, 3H), 3.26 (qd, J=15.2, 6.7 Hz, 2H), 2.65-2.48 (m, 2H), 2.40-2.21 (m, 2H), 2.15 (s, 6H), 1.29 (d, J=6.7 Hz, 3H). $^{13}$C NMR (75 MHz, CDCl$_3$) δ 158.3, 143.0, 142.5, 139.7, 136.4, 130.0, 128.7, 128.1 (2C), 128.0, 127.4, 127.2, 127.1, 113.4, 59.2, 58.1, 55.2, 49.28, 48.0, 45.8, 17.3. HRMS (ESI) calcd for C$_{28}$H$_{35}$N$_2$O 415.2749 (M+H)$^+$, found 415.2738.

(R)—N$^1$-(3,3-Diphenylallyl)-N$^2$,N$^2$-diethyl-N$^1$-(1-(4-methoxyphenyl)ethyl)ethane-1,2-diamine (12b)

Compound 12b (30 mg, 69%) was prepared by a procedure similar to that used to prepare compound 12a from diethylamine. The title compound was obtained as a colorless oil. $^1$H NMR (300 MHz, CDCl$_3$) δ 7.40-7.21 (m, 10H), 7.15 (d, J=6.1 Hz, 2H), 6.83 (d, J=7.6 Hz, 2H), 6.23 (t, J=6.1 Hz, 1H), 3.88 (q, J=6.5 Hz, 1H), 3.81 (s, 3H), 3.34-3.14 (m, 2H), 2.58-2.38 (m, 8H), 1.28 (d, J=6.3 Hz, 3H), 0.95 (t, J=7.0 Hz, 6H). $^{13}$C NMR (75 MHz, CDCl$_3$) δ 158.3, 142.8, 142.5, 139.7, 136.4, 130.0, 128.7, 128.4, 128.1, 128.0, 127.4, 127.1 (2C), 113.4, 59.1, 55.3, 51.9, 49.8, 48.1, 47.4, 16.9, 11.7. HRMS (ESI) calcd for C$_{30}$H$_{39}$N$_2$O 443.3062 (M+H)+, found 443.3059.

(R)—N-(1-(4-Methoxyphenyl)ethyl)-3,3-diphenyl-N-(2-(piperidin-1-yl)ethyl)prop-2-en-1-amine (12c)

Compound 12c (14 mg, 32%) was prepared by a procedure similar to that used to prepare compound 12a from piperidine. The title compound was obtained as a colorless oil. $^1$H NMR (300 MHz, CDCl$_3$) δ 7.42-7.21 (m, 10H), 7.16 (d, J=7.1 Hz, 2H), 6.83 (d, J=7.6 Hz, 2H), 6.23 (t, J=6.4 Hz, 1H), 3.89 (q, J=6.2 Hz, 1H), 3.81 (s, 3H), 3.24 (t, J=6.5 Hz, 2H), 2.69-2.52 (m, 2H), 2.45-2.23 (m, 6H), 1.63-1.35 (m, 4H), 1.46-1.34 (m, 2H), 1.28 (d, J=6.7 Hz, 3H). $^{13}$C NMR (75 MHz, CDCl$_3$) δ 158.3, 142.7, 142.5, 139.7, 136.3, 130.0, 128.7, 128.5, 128.1 (2C), 127.4, 127.1 (2C), 113.4, 58.9, 58.1, 55.2, 55.0, 49.6, 47.4, 25.9, 24.38, 16.8. HRMS (ESI) calcd for C$_{31}$H$_{39}$N$_2$O 455.3062 (M+H)+, found 455.3062.

(R)—N-(1-(4-Methoxyphenyl)ethyl)-N-(2-morpholinoethyl)-3,3-diphenylprop-2-en-1-amine (12d)

Compound 12d (14 mg, 31%) was prepared by a procedure similar to that used to prepare compound 12a from morpholine. The title compound was obtained as a colorless oil. $^1$H NMR (300 MHz, CDCl$_3$) δ 7.43-7.12 (m, 12H), 6.87 (d, J=8.0 Hz, 2H), 6.22 (t, J=6.5 Hz, 1H), 3.89 (q, J=6.4 Hz, 1H), 3.81 (s, 3H), 3.77-3.61 (m, 4H), 3.26 (t, J=6.2 Hz, 2H), 2.67-2.53 (m, 2H), 2.43-2.29 (m, 6H), 1.28 (d, J=6.7 Hz, 3H). $^{13}$C NMR (75 MHz, CDCl$_3$) 158.3, 143.0, 142.5, 139.7, 136.3, 129.9, 128.7, 128.1 (2C), 127.4, 127.2, 127.1, 113.4, 66.9, 59.0, 57.7, 55.2, 54.1, 49.4, 47.0, 16.9. HRMS (ESI) calcd for $C_{30}H_{37}N_2O_2$ 457.2855 (M+H)+, found 457.2853.

(R)—N-(1-(4-Methoxyphenyl)ethyl)-3,3-diphenyl-N-(2-(piperazin-1-yl)ethyl)prop-2-en-1-amine (12e)

Compound 12e (21 mg, 45%) was prepared by a procedure similar to that used to prepare compound 12a from piperazine. The title compound was obtained as a colorless oil. $^1$H NMR (300 MHz, CDCl$_3$) δ 7.39-7.21 (m, 10H), 7.15 (d, J=6.6 Hz, 2H), 6.82 (d, J=7.0 Hz, 2H), 6.21 (t, J=6.0 Hz, 1H), 3.88 (q, J=5.8 Hz, 1H), 3.80 (s, 3H), 3.34-3.16 (m, 2H), 2.92-2.79 (m, 4H), 2.66-2.45 (m, 2H), 2.43-2.18 (m, 7H), 1.26 (d, J=6.0 Hz, 3H). $^{13}$C NMR (75 MHz, CDCl$_3$) δ 158.3, 142.9, 142.5, 139.7, 136.3, 129.9, 128.7, 128.3, 128.1 (2C), 127.4, 127.2, 127.1, 113.4, 58.9, 57.9, 55.2, 54.8, 49.5, 47.1, 45.9, 16.9. HRMS (ESI) calcd for $C_{30}H_{38}N_3O$ 456.3015 (M+H)+, found 456.3069.

(R)—N-(1-(4-Methoxyphenyl)ethyl)-N-(2-(4-methylpiperazin-1-yl)ethyl)-3,3-diphenylprop-2-en-1-amine (12f (NY0244))

Compound 12f (NY0244) (20 mg, 43%) was prepared by a procedure similar to that used to prepare compound 12a from 1-methylpiperazine. The title compound was obtained as a colorless oil. $^1$H NMR (300 MHz, CDCl$_3$) δ 7.40-7.22 (m, 10H), 7.15 (dd, J=7.6, 1.8 Hz, 2H), 6.86-6.79 (m, 2H), 6.22 (t, J=6.6 Hz, 1H), 3.89 (q, J=6.7 Hz, 1H), 3.80 (s, 3H), 3.33-3.16 (m, 2H), 2.71-2.29 (m, 12H), 2.28 (s, 3H), 1.27 (d, J=6.8 Hz, 3H). $^{13}$C NMR (75 MHz, CDCl$_3$) δ 158.3, 142.9, 142.5, 139.7, 136.3, 129.9, 128.7, 128.3, 128.1, 128.0, 127.4, 127.1 (2C), 113.4, 59.0, 57.2, 55.2, 55.0, 53.5, 49.5, 47.3, 46.0, 17.0. HRMS (ESI) calcd for $C_{31}H_{40}N_3O$ 470.3171 (M+H)+, found 470.3172.

(R)-4-(2-((3,3-Diphenylallyl)(1-(4 methoxyphenyl)ethyl)amino)ethyl)piperazin-2-one (12g)

Compound 12g (18 mg, 38%) was prepared by a procedure similar to that used to prepare compound 12a from piperazin-2-one. The title compound was obtained as a colorless oil. NMR (300 MHz, CDCl$_3$) δ 7.41-7.21 (m, 10H), 7.15 (d, J=7.0 Hz, 2H), 6.83 (d, J=8.0 Hz, 2H), 6.47 (s, 1H), 6.21 (t, J=6.5 Hz, 1H), 3.89 (q, J=6.3 Hz, 1H), 3.81 (s, 3H), 3.37-3.16 (m, 4H), 3.04 (s, 2H), 2.64-2.47 (m, 4H), 2.37 (d, J=6.5 Hz, 2H), 1.27 (d, J=6.5 Hz, 3H). $^{13}$C NMR (75 MHz, CDCl$_3$) δ 169.6, 158.4, 143.3, 142.4, 139.6, 136.1, 129.9, 128.7, 128.2, 128.1, 127.6, 127.4, 127.3, 127.2, 113.4, 59.0, 57.3, 56.0, 55.2, 49.3, 49.2, 47.2, 41.3, 17.0. HRMS (ESI) calcd for $C_{30}H_{36}N_3O_2$ 470.2808 (M+H)+, found 470.2806.

(R)—N-(1-(4-Methoxyphenyl)ethyl)-3,3-diphenyl-N-(2-(pyrrolidin-1-yl)ethyl)prop-2-en-1-amine (12h (NY0331))

Compound 12h (NY0331) (26 mg, 59%) was prepared by a procedure similar to that used to prepare compound 12a from pyrrolidine. The title compound was obtained as a colorless oil. $^1$H NMR (300 MHz, CDCl$_3$) δ 7.43-7.20 (m, 10H), 7.15 (d, J=6.7 Hz, 2H), 6.82 (d, J=7.8 Hz, 2H), 6.22 (t, J=6.2 Hz, 1H), 3.88 (dd, J=13.2, 6.5 Hz, 1H), 3.81 (s, 3H), 3.35-3.14 (m, 2H), 2.73-2.48 (m, 4H), 2.47-2.35 (m, 4H), 1.84-1.64 (m, 4H), 1.28 (d, J=6.1 Hz, 3H). $^{13}$C NMR (75 MHz, CDCl$_3$) δ 158.3, 142.8, 142.5, 139.7, 136.3, 130.0, 128.7, 128.3, 128.1, 128.0, 127.4, 127.1 (2C), 113.4, 59.0, 55.2 (2C), 54.5, 49.6, 49.0, 23.4, 17.1. HRMS (ESI) calcd for $C_{30}H_{37}N_2O$ 441.2906 (M+H)+, found 441.2906.

(R)—N-(2-(azetidin-1-yl)ethyl)-N-(1-(4-methoxyphenyl)ethyl)-3,3-diphenylprop-2-en-1-amine (12i)

Compound 12i (25 mg, 59%) was prepared by a procedure similar to that used to prepare compound 12a from azetidine hydrochloride. The title compound was obtained as a colorless oil. $^1$H NMR (300 MHz, CDCl$_3$) δ 7.41-7.30 (m, 4H), 7.24 (dd, J=10.7, 6.0 Hz, 6H), 7.15 (dd, J=7.7, 1.7 Hz, 2H), 6.85-6.79 (m, 2H), 6.21 (t, J=6.7 Hz, 1H), 3.87 (q, J=6.9 Hz, 1H), 3.80 (s, 3H), 3.35-3.17 (m, 6H), 2.56-2.42 (m, 4H), 2.18-2.09 (m, 2H), 1.26 (d, J=6.9 Hz, 3H). $^{13}$C NMR (75 MHz, CDCl$_3$) δ 158.4, 143.3, 142.3, 139.6, 129.9, 128.8, 128.1 (2C), 127.4, 127.2 (C), 113.4, 59.1, 55.2, 55.0, 49.6, 47.0, 29.7, 17.5, 16.9. HRMS (ESI) calcd for $C_{29}H_{35}N_2O$ 427.2749 (M+H)+, found 427.2740.

tert-Butyl (R)-4-(2-((1-(4-methoxyphenyl)ethyl)amino)ethyl)piperazine-1-carboxylate (13)

A mixture of K$_2$CO$_3$ (690 mg, 5 mmol), KI (cat.) and tert-butyl 4-(2-chloroethyl)piperazine-1-carboxylate (450 mg, 2.4 mmol) in MeCN (10 mL) was heated at 50° C. for 1 h. Then (R)-1-(4-methoxyphenyl)ethanamine 9a (310 mg, 2 mmol) was added to the mixture and stirred at 80° C. overnight. After completion of the reaction, the contents were cooled to rt, removed the solvent, diluted with water and then extracted with EtOAc (30 mL). The organic phase was washed with brine, dried over Na$_2$SO$_4$, and concentrated to yield 450 mg of amine 13 used directly for next step.

(R,E)-N-(1-(4-Methoxyphenyl)ethyl)-N-(2-(4-methylpiperazin-1-yl)ethyl)-3-phenylprop-2-en-1-amine (14a)

A RB flask with magnetic stir bar was charged with 1,2-dichloroethane (10 mL), phosphotungstic acid hydrate (cat.), crude 13 (100 mg, 0.27 mmol) and cinnamylaldehyde (28 mg, 0.22 mmol). To the stirred reaction solution under a nitrogen atmosphere was added NaBH(OAc)$_3$ (87 mg, 0.41 mmol). The flask was sealed under nitrogen and stirred at rt for 48 h. The reaction was worked up by the addition of sat. aq. NaHCO$_3$ and EtOAc. The combined EtOAc extracts were washed with brine, dried over NaSO$_4$, filtered, and condensed by rotary evaporation to yield a crude oil. This material was further purified by silica gel column chromatography using EtOAc/Hex (2/1) as the eluant to yield tert-butyl (R)-4-(2-(cinnamyl(1-(4-methoxyphenyl)ethyl)amino)ethyl)-piperazine-1-carboxylate (45 mg, 45%) as a colorless oil. $^1$H NMR (300 MHz, CDCl$_3$) δ 7.41-7.19 (m, 7H), 6.88 (d, J=8.3 Hz, 2H), 6.52 (d, J=16.0 Hz, 1H), 6.32-6.19 (m, 1H), 3.93 (q, J=6.6 Hz, 1H), 3.82 (s, 3H), 3.46-3.36 (m, 4H), 3.35-3.19 (m, 2H), 2.76-2.58 (m 2H), 2.52-2.42 (m, 2H), 2.40-2.26 (m, 4H), 1.47 (s, 9H), 1.39 (d, J=6.7 Hz, 3H). $^{13}$C NMR (75 MHz, CDCl$_3$) δ 158.4, 154.7, 137.3, 136.0, 131.7, 128.7 (2C), 128.6, 127.3, 126.2, 113.4, 79.5, 58.8, 57.5, 55.2, 53.4, 53.3, 47.0, 28.4, 16.7.

To a solution of tert-butyl (R)-4-(2-(cinnamyl(1-(4-methoxyphenyl)ethyl)amino)ethyl) piperazine-1-carboxylate (45 mg, 0.09 mmol) in EtOH (2 mL) was added 6 N HCl (1 mL) at 0° C. The mixture was stirred at rt overnight. Part of the solvent was removed, and then the pH of the residue was adjusted to 7-8 with aq NH$_4$OH and extracted with EtOAc. The combined EtOAc extracts were washed with brine, dried NaSO$_4$, filtered, and condensed by rotary evaporation to yield a colorless oil used directly in the next step. To a solution of previous colorless oil and 37 wt. % formaldehyde aqueous solution (0.04 mL, 0.47 mmol) in 1,2-dichloroethane (5 mL) was added acetic acid (cat.). 10 min later, NaBH(OAc)$_3$ (40 mg, 0.19 mmol) was then added to the stirred reaction solution. The flask was stirred at rt for 24 h. The reaction was worked up by the addition of sat. aq. NaHCO$_3$ and EtOAc. The combined EtOAc extracts were washed with brine, dried over NaSO$_4$, filtered, and condensed under reduced pressure. The residue was further purified by preparative TLC plates using DCM/MeOH (10/1) as the eluant to yield 14a (24 mg, 67% for two step) as a yellow oil. $^1$H NMR (300 MHz, CDCl$_3$) δ 7.40-7.15 (m, 7H), 6.87 (d, J=7.9 Hz, 2H), 6.51 (d, J=15.8 Hz, 2H), 6.32-6.17 (m, 1H), 3.92 (q, J=6.8 Hz, 1H), 3.81 (s, 3H), 3.37-3.18 (m, 2H), 2.78-2.61 (m, 2H), 2.60-2.33 (m, 10H), 2.27 (s, 3H), 1.38 (d, J=6.6 Hz, 3H). $^{13}$C NMR (75 MHz, CDCl$_3$) δ 158.4, 137.3, 136.0, 131.6, 128.8, 128.7, 128.5, 127.2, 126.2, 113.4, 58.8, 57.4, 55.2, 55.0, 53.6, 53.4, 47.0, 46.0, 16.9. HRMS (ESI) calcd for C$_{25}$H$_{36}$N$_3$O 394.2858 (M+H)+, found 394.2860.

(R)—N-(1-(4-Methoxyphenyl)ethyl)-N-(2-(4-methylpiperazin-1-yl)ethyl)prop-2-en-1-amine (14b)

To a solution of crude 13 (61 mg, 0.17 mmol) in MeCN (4 mL) was added K$_2$CO$_3$ (60 mg, 0.44 mmol), KI (cat.) and propargyl bromide (0.03 mL, 0.33 mmol). Then the mixture was stirred at 50° C. for 3 h. After removing the solvent, the residue was diluted with water (8 mL) and extracted with EtOAc (15 mL×2). The combined EtOAc extracts were washed with brine, dried Na$_2$SO$_4$, filtered, and condensed by rotary evaporation to yield a crude oil. This material was further purified by preparative TLC plates using EtOAc/Hex as the eluant to yield tert-butyl (R)-4-(2-(allyl(1-(4-methoxyphenyl)ethyl)amino)ethyl)piperazine-1-carboxylate (28 mg, 41%). $^1$H NMR (300 MHz, CDCl$_3$) δ 7.27 (d, J=7.5 Hz, 2H), 6.85 (d, J=7.6 Hz, 2H), 5.85 (td, J=16.0, 6.2 Hz, 1H), 5.13 (dd, J=23.2, 13.6 Hz, 2H), 3.91-3.83 (q, J=6.0 Hz, 1H), 3.81 (s, 3H), 3.48-3.32 (m, 4H), 3.22-2.99 (m, 2H), 2.68-2.48 (m, 2H), 2.48-2.25 (m, 6H), 1.46 (s, 9H), 1.33 (d, J=6.6 Hz, 3H). $^{13}$C NMR (75 MHz, CDCl$_3$) δ 158.3, 154.7, 136.9, 136.0, 128.7, 116.6, 113.4, 79.5, 58.5, 57.4, 55.2, 53.9, 53.4, 46.8, 28.4, 16.6.

To a solution of tert-butyl (R)-4-(2-(allyl(1-(4-methoxyphenyl)ethyl)amino)ethyl) piperazine-1-carboxylate (28 mg, 0.07 mmol) in EtOH (2 mL) was added 6 N HCl (1 mL) at 0° C. The mixture was stirred at rt overnight. Part of the solvent was removed, and then the residue was adjusted to pH 7-8 with aq. NH$_4$OH and extracted with EtOAc. The combined EtOAc extracts were washed with brine, dried Na$_2$SO$_4$, filtered, and condensed by rotary evaporation to yield a colorless oil used directly in the next step. To a solution of previous colorless oil and 37 wt. % formaldehyde aqueous solution (0.03 mL, 0.35 mmol) in 1,2-dichloroethane (4 mL) was added acetic acid (cat.). 10 min later, NaBH(OAc)$_3$ (30 mg, 0.14 mmol) was then added to the stirred reaction solution. The flask was stirred at rt for 24 h. The reaction was worked up by the addition of sat. aq. NaHCO$_3$ and EtOAc. The combined EtOAc extracts were washed with brine, dried Na$_2$SO$_4$, filtered, and condensed under reduced pressure. The residue was further purified by preparative TLC plates using DCM/MeOH (10/1) as the eluant to yield 14b (14 mg, 64% for two steps) as a colorless oil. $^1$H NMR (300 MHz, Chloroform-d) δ 7.27 (d, J=7.2 Hz, 2H), 6.85 (d, J=7.9 Hz, 2H), 5.94-5.76 (m, 1H), 5.23-5.03 (m, 2H), 3.86 (q, J=9.0 Hz, 1H), 3.81 (s, 3H), 3.22-2.99 (m, 2H), 2.71-2.33 (m, 12H), 2.27 (s, 3H), 1.33 (d, J=6.5 Hz, 3H). $^{13}$C NMR (75 MHz, CDCl$_3$) δ 158.3, 137.0, 136.1, 128.7, 116.5, 113.3, 58.5, 57.3, 55.2, 55.0, 53.9, 53.6, 46.8, 46.0, 16.7. HRMS (ESI) calcd for C$_{19}$H$_{32}$N$_3$O 318.2545 (M+H)+, found 318.2547.

(S)—N-(1-(4-Methoxyphenyl)ethyl)-N-(2-(4-methylpiperazin-1-yl)ethyl)-3,3-diphenylprop-2-en-1-amine (15a)

A RB flask with activated 4 Å molecular sieves and dried anhydrous Na$_2$SO$_4$ was charged with THF (2 mL), (S)-1-(4-methoxyphenyl)ethanamine 9b (15 mg, 0.1 mmol) and β-phenylcinnamylaldehyde (21 mg, 0.1 mmol) under a nitrogen atmosphere. The reaction mixture was stirred at rt for 48 h, and then removed the solvent and refilled with MeOH (2 mL). To the solution was added NaBH$_4$ (4 mg, 0.1 mmol) at 0° C. and reacted for 2 h. After removing the solvent, the residue was diluted with water (10 mL) and extracted with EtOAc (10 mL×3). The combined organic phase was acidized with 4 N aq. HCl to pH<3 and extracted with Et$_2$O (15 mL×3). The aqueous phase was separated and basified with 10 N aq. NaOH to pH>9, and then extracted with EA (15 mL×3). The combined EtOAc extracts were washed with brine, dried with NaSO$_4$, filtered, and condensed by rotary evaporation to as a colorless oil used directly in the next step. To a solution of the crude colorless oil and acetaldehyde (50 µL, 0.10 mmol) in 1,2-dichloroethane (2 mL) was added acetic acid (cat.). 10 min later, NaBH(OAc)$_3$ (21 mg, 0.1 mmol) was added to the stirred reaction solution. The flask was stirred at rt for 2 h. The reaction was worked up by the addition of sat. aq. NaHCO$_3$ and EtOAc. The combined EtOAc extracts were washed with brine, dried over Na$_2$SO$_4$, filtered, and condensed under reduced pressure. The residue was added to a solution of K$_2$CO$_3$ (23 mg, 0.17 mmol), KI (cat.) in MeCN (5 mL). The mixture solution was heated at reflux for 1 h. Then 1-methylpiperazine (22 µL, 0.2 mmol) was added to the mixture and stirred at reflux overnight. After completion of the reaction, the contents were cooled to rt, poured into ice water and then extracted with EtOAc. The combined organic phase was washed with brine, dried over Na$_2$SO$_4$, and then concentrated under reduced pressure. The residue was purified by preparative TLC plates (DCM/MeOH=15/1) to give 15a (25 mg, 53%) as a yellow oil. $^1$H NMR (300 MHz, CDCl$_3$) δ 7.40-7.32 (m, 3H), 7.29-7.23 (m, 7H), 7.18-7.11 (m, 2H), 6.82 (d, J=8.7 Hz, 2H), 6.21 (t, J=6.6 Hz, 1H), 3.88 (q, J=6.8 Hz, 1H), 3.81 (s, 3H), 3.32-3.13 (m, 2H), 2.64-2.55 (m, 2H), 2.55-2.29 (m, 10H), 2.28 (s, 3H), 1.27 (d, J=6.8 Hz, 3H). $^{13}$C NMR (75 MHz, CDCl$_3$) δ 158.3, 142.9, 142.5, 139.7, 136.3, 129.9, 128.7, 128.3, 128.1 (4C), 127.4, 127.2, 127.1, 113.4, 59.0, 57.2, 55.2, 55.0, 53.5, 49.5, 47.3, 46.0, 17.0. HRMS (ESI) calcd for C$_{31}$H$_{40}$N$_3$O 470.3171 (M+H)±, found 470.3163.

(R)—N-(1-(2-Methoxyphenyl)ethyl)-N-(2-(4-methylpiperazin-1-yl)ethyl)-3,3-diphenylprop-2-en-1-amine (15b)

Compound 15b (11 mg, 23%) was prepared for three steps by a procedure similar to that used to prepare compound 15a from (R)-1-(2-methoxyphenyl)ethanamine 9c. The title compound was obtained as a yellow oil. $^1$H NMR (300 MHz, CDCl$_3$) δ 7.44-7.13 (m, 12H), 6.96-6.82 (m, 2H), 6.29 (t, J=6.3 Hz, 1H), 4.40 (q, J=6.6 Hz, 1H), 3.81 (s, 3H), 3.41-3.23 (m, 2H), 2.76-2.61 (m, 2H), 2.56-2.29 (m, 10H), 2.27 (s, 3H), 1.26 (d, J=6.8 Hz, 3H). $^{13}$C NMR (75 MHz, CDCl$_3$) δ 157.0, 142.6, 142.6, 139.7, 133.1, 129.9, 128.3, 128.1, 128.0, 127.7, 127.4 (2C), 127.1, 127.0, 120.4, 110.5, 56.6, 55.4, 55.1, 53.5, 52.7, 49.8, 47.6, 46.0, 18.7. HRMS (ESI) calcd for C$_{31}$H$_{40}$N$_3$O 470.3171 (M+H)+, found 470.3167.

(R)—N-(1-(3-Methoxyphenyl)ethyl)-N-(2-(4-methylpiperazin-1-yl)ethyl)-3,3-diphenylprop-2-en-1-amine (15c)

Compound 15c (15 mg, 32%) was prepared for three steps by a procedure similar to that used to prepare compound 15a from (R)-1-(3-methoxyphenyl)ethanamine 9d. The title compound was obtained as a yellow oil. $^1$H NMR (300 MHz, CDCl$_3$) δ 7.38-7.32 (m, 3H), 7.30-7.22 (m, 6H), 7.17-7.11 (m, 2H), 6.94 (d, J=8.8 Hz, 2H), 6.80-6.74 (m, 1H), 6.22 (t, J=6.6 Hz, 1H), 3.89 (q, J=6.6 Hz, 1H), 3.81 (s, 3H), 3.27 (dd, J=6.4, 3.8 Hz, 2H), 2.61 (t, J=7.5 Hz, 2H), 2.53-2.31 (m, 10H), 2.28 (s, 3H), 1.27 (d, J=6.5 Hz, 3H). $^{13}$C NMR (75 MHz, CDCl$_3$) δ 159.5, 146.4, 143.0, 142.4, 139.6, 129.9, 129.0, 128.1 (3C), 128.0, 127.4, 127.2, 127.1 (2C), 113.4, 111.9, 59.8, 57.0, 55.2, 55.0, 53.4, 49.5, 47.4, 46.0, 17.2. HRMS (ESI) calcd for C$_{31}$H$_{40}$N$_3$O 470.3171 (M+H)$^+$, found 470.3171.

(R)—N-(2-(4-Methylpiperazin-1-yl)ethyl)-3,3-diphenyl-N-(1-phenylethyl)prop-2-en-1-amine (15d)

Compound 15d (18 mg, 41%) was prepared for three steps by a procedure similar to that used to prepare compound 15a from (R)-1-phenylethanamine 9e. The title compound was obtained as a colorless oil. $^1$H NMR (300 MHz, CDCl$_3$) δ 7.39-7.22 (m, 13H), 7.18-7.13 (m, 2H), 6.23 (t, J=6.6 Hz, 1H), 3.93 (d, J=6.7 Hz, 1H), 3.27 (t, J=6.3 Hz, 2H), 2.65-2.57 (m, 2H), 2.56-2.30 (m, 10H), 2.28 (s, 3H), 1.30 (d, J=6.7 Hz, 3H). $^{13}$C NMR (75 MHz, CDCl$_3$) δ 144.4, 143.0, 142.5, 139.7, 129.9, 128.1 (4C), 127.7, 127.4, 127.2, 127.1, 126.7, 59.7, 57.1, 55.0, 53.5, 49.6, 47.4, 46.0, 17.0. HRMS (ESI) calcd for C$_{30}$H$_{38}$N$_3$ 440.3066 (M+H)$^+$, found 440.3066.

(R)—N-(1-(4-Fluorophenyl)ethyl)-N-(2-(4-methylpiperazin-1-yl)ethyl)-3,3-diphenylprop-2-en-1-amine (15e)

Compound 15e (14 mg, 31%) was prepared for three steps by a procedure similar to that used to prepare compound 15a from (R)-1-(4-fluorophenyl)ethanamine 9f. The title compound was obtained as a colorless oil. $^1$H NMR (300 MHz, CDCl$_3$) δ 7.38-7.24 (m, 10H), 7.16-7.10 (m, 2H), 7.00-6.92 (m, 2H), 6.20 (t, J=6.6 Hz, 1H), 3.91 (q, J=6.7 Hz, 1H), 3.24 (t, J=6.3 Hz, 2H), 2.62-2.54 (m, 2H), 2.53-2.31 (m, 10H), 2.29 (s, 3H), 1.26 (d, J=6.7 Hz, 3H). $^{13}$C NMR (75 MHz, CDCl$_3$) δ 161.7 (d, J=242.9 Hz), 143.2, 142.4, 140.0 (2C), 139.6, 129.9 (3C), 129.1, 129.0, 128.2 (2C), 128.1 (4C), 127.8, 127.4 (2C), 127.3, 127.2 (2C), 114.9, 114.6, 58.9, 57.1, 54.9, 53.4, 49.5, 47.2, 45.9, 16.8. HRMS (ESI) calcd for C$_{30}$H$_{37}$N$_3$F 458.2972 (M+H)$^+$, found 458.2962.

(R)—N-(1-(4-Chlorophenyl)ethyl)-N-(2-(4-methylpiperazin-1-yl)ethyl)-3,3-diphenylprop-2-en-1-amine (15f)

Compound 15f (13 mg, 28%) was prepared for three steps by a procedure similar to that used to prepare compound 15a from (R)-1-(4-chlorophenyl)ethanamine 9g. The title compound was obtained as a colorless oil. $^1$H NMR (300 MHz, CDCl$_3$) δ 7.41-7.32 (m, 3H), 7.32-7.19 (m, 9H), 7.13 (dd, J=7.5, 1.8 Hz, 2H), 6.19 (t, J=6.6 Hz, 1H), 3.89 (d, J=6.7 Hz, 1H), 3.23 (dd, J=6.5, 4.8 Hz, 2H), 2.63-2.34 (m, 12H), 2.29 (s, 3H), 1.27 (t, J=5.9 Hz, 3H). $^{13}$C NMR (75 MHz, CDCl$_3$) δ 143.2, 143.0, 142.3, 139.6, 132.2, 129.9, 129.0, 128.2, 128.1, 127.8, 127.4, 127.3, 127.2, 59.0, 57.1, 55.0, 53.5, 49.5, 47.3, 46.0, 16.7. HRMS (ESI) calcd for C$_{30}$H$_{37}$N$_3$Cl 474.2676 (M+H)$^+$, found 474.2675.

(R)—N-(1-(3-Chlorophenyl)ethyl)-N-(2-(4-methylpiperazin-1-yl)ethyl)-3,3-diphenylprop-2-en-1-amine (15g)

Compound 15g (17 mg, 36%) was prepared for three steps by a procedure similar to that used to prepare compound 15a from (R)-1-(3-chlorophenyl)ethanamine 9h. The title compound was obtained as a colorless oil. $^1H$ NMR (300 MHz, CDCl$_3$) δ 7.39-7.17 (m, 12H), 7.14 (d, J=7.0 Hz, 2H), 6.19 (t, J=6.3 Hz, 1H), 3.89 (q, J=6.5 Hz, 1H), 3.34-3.13 (m, 2H), 2.58 (t, J=7.2 Hz, 2H), 2.54-2.30 (m, 10H), 2.28 (s, 3H), 1.26 (d, J=6.7 Hz, 3H). $^{13}$C NMR (75 MHz, CDCl$_3$) δ 146.9, 143.2, 142.3, 139.5, 134.0, 129.9, 129.3, 128.1 (2C), 127.8, 127.7, 127.4, 127.2 (2C), 126.8, 125.8, 59.2, 57.1, 55.0, 53.6, 49.5, 47.4, 46.0, 16.6. HRMS (ESI) calcd for C$_{30}$H$_{37}$N$_3$Cl 474.2676 (M+H)$^+$, found 474.2680.

(R)—N-(2-(4-Methylpiperazin-1-yl)ethyl)-N-(1-(4-nitrophenyl)ethyl)-3,3-diphenylprop-2-en-1-amine (15h)

Compound 15h (7 mg, 15%) was prepared for three steps by a procedure similar to that used to prepare compound 15a from (R)-1-(4-nitrophenyl)ethanamine 9i. The title compound was obtained as a yellow oil. $^1H$ NMR (300 MHz, CDCl$_3$) δ 8.13 (d, J=8.8 Hz, 2H), 7.52 (d, J=8.6 Hz, 2H), 7.37-7.22 (m, 8H), 7.15-7.08 (m, 2H), 6.18 (t, J=6.7 Hz, 1H), 4.01 (q, J=6.7 Hz, 1H), 3.24 (dd, J=6.7, 3.6 Hz, 2H), 2.64-2.56 (m, 2H), 2.56-2.31 (m, 10H), 2.30 (s, 3H), 1.29 (d, J=6.7 Hz, 3H). $^{13}$C NMR (75 MHz, CDCl$_3$) δ 152.6, 146.8, 143.7, 142.2, 139.4, 129.8, 128.3, 128.2 (3C), 127.4, 127.3, 127.1, 123.4, 59.2, 57.0, 54.9, 53.4, 49.4, 47.4, 45.9, 16.5. HRMS (ESI) calcd for C$_{30}$H$_{37}$N$_4$O$_2$ 485.2917 (M+H)$^+$, found 485.2917.

(R)-Methyl 2-((3,3-diphenylallyl)(1-(4-methoxyphenyl)ethyl)amino)acetate (16)

Compound 16 (764 mg, 92%) was prepared by a similar procedure to that of compound 11a from methyl chloroacetate. The title compound was obtained as a colorless oil. $^1$H NMR (300 MHz, CDCl$_3$) δ 7.43-7.27 (m, 10H), 7.21-7.13 (m, 2H), 6.93-6.85 (m, 2H), 6.28 (t, J=6.9 Hz, 1H), 4.07 (q, J=6.7 Hz, 1H), 3.83 (s, 3H), 3.63 (s, 3H), 3.52-3.28 (m, 4H), 1.34 (d, J=6.7 Hz, 3H). $^{13}$C NMR (75 MHz, CDCl$_3$) δ 172.6, 158.6, 143.8, 142.2, 139.5, 136.3, 129.9, 128.6, 128.2, 128.1, 127.4, 127.2 (2C), 113.6, 59.6, 55.2, 51.4, 51.3, 50.1, 19.3. HRMS (ESI) calcd for C$_{27}$H$_{30}$NO$_3$ 416.2226 (M+H)$^+$, found 416.2227.

(R)-2-((3,3-Diphenylallyl)(1-(4-methoxyphenyl)ethyl)amino)acetic acid (17)

A solution of lithium hydroxide (84 mg, 2.0 mmol) in water (1 mL) was added to the solution of ester 16 (415 mg, 1.0 mmol) in THF (3 mL). The mixture was stirred overnight. After removal of the solvent, the residue was diluted with water (2 mL), acidified with 6 N HCl to pH=5, and then extracted with EtOAc (15 mL×2). The combined organic layer was washed with brine (10 mL), dried, filtered, and then evaporated to yield 17 (374 mg, 93%) as a white solid. $^1$H NMR (300 MHz, CDCl$_3$+CD$_3$OD) δ7.27-7.11 (m, 8H), 7.09-6.94 (m, 4H), 6.66 (d, J=8.7 Hz, 2H), 6.24 (t, J=6.5 Hz, 1H), 4.07 (q, J=6.9 Hz, 1H), 3.68 (s, 3H), 3.38 (dd, J=14.8, 5.9 Hz, 1H), 3.31-3.08 (m, 2H), 2.87 (d, J=16.1 Hz, 1H), 1.30 (d, J=6.9 Hz, 3H). $^{13}$C NMR (75 MHz, CDCl$_3$+CD$_3$OD) δ 176.4, 158.8, 144.8, 141.8, 139.0, 131.2, 129.6, 129.5, 128.1, 127.4, 124.5, 113.5, 59.6, 55.1, 54.4, 50.4, 17.2. FIRMS (ESI) calcd for C$_{26}$H$_{28}$NO$_3$ 402.2069 (M+H)+, found 402.2082.

(R)-2-((3,3-Diphenylallyl)(1-(4-methoxyphenyl) ethyl)amino)-1-(4-methylpiperazin-1-yl)ethanone (18)

To a solution of 17 (200 mg, 0.5 mmol) in DCM (4 mL), 1-methylpiperazine (100 mg, 2 mmol), EDCI (192 mg, 2 mmol), HOBt (68 mg, 0.5 mmol) and DIPEA (194 mg, 1.54 mmol) were successively added. The mixture was stirred for overnight, diluted with ice water (8 mL) and then extracted with EtOAc (15 mL×2). The combined organic phase was washed with brine, dried over Na$_2$SO$_4$, and then concentrated under reduced pressure. The residue was purified by preparative TLC plates (Hexane/EtOAc) to give the 18 (200 mg, 83%) as a yellow oil. $^1$H NMR (600 MHz, CDCl$_3$) δ 7.38-7.27 (m, 6H), 7.26-7.24 (m, 2H), 7.22 (d, J=8.7 Hz, 2H), 7.14 (dd, J=8.1, 1.5 Hz, 2H), 6.84 (d, J=8.6 Hz, 2H), 6.23-6.18 (m, 1H), 4.03 (q, J=6.8 Hz, 1H), 3.81 (s, 3H), 3.57 (m, 2H), 3.48-3.44 (m, 2H), 3.27 (td, J=14.7, 6.8 Hz, 2H), 3.22 (d, J=3.0 Hz, 2H), 2.34 (m, 4H), 2.30 (s, 3H), 1.23 (d, J=6.9 Hz, 3H). $^{13}$C NMR (150 MHz, CDCl$_3$) 169.7, 158.6, 143.9, 142.3, 139.4, 134.6, 129.9, 129.1, 128.2, 128.1, 127.4, 127.3, 113.4, 58.3, 55.3, 55.2, 54.7, 53.3, 49.5, 46.0, 45.1, 41.6, 14.6. HRMS (ESI) calcd for C$_{31}$H$_{38}$N$_3$O$_2$ 484.2964 (M+H)$^+$, found 484.2979.

(R)-2-Chloro-N-(3,3-diphenylallyl)-N-(1-(4-methoxyphenyl)ethyl)acetamide (19)

To a solution of 10a (343 mg, 1 mmol) in CH$_2$Cl$_2$ (4 mL) was added Et$_3$N (0.4 mL, 3 mmol), then 2-chloroacetyl chloride (134 mg, 1.2 mmol) was added to the stirred reaction solution. The mixture was stirred at rt for 2 h. The reaction was worked up by the addition of sat. aq. NaHCO$_3$ and EtOAc. The combined EtOAc extracts were washed with brine, dried over Na$_2$SO$_4$, filtered, and condensed under reduced pressure. The residue was further purified by preparative TLC plates using Hexane/EtOAc (5/1) as the eluant to yield 19 (303 mg, 72%) as a yellow oil. $^1$H NMR (300 MHz, CDCl$_3$) δ 7.46-7.34 (m, 3H), 7.30-7.21 (m, 4H), 7.12 (td, J=7.4, 7.0, 3.0 Hz, 5H), 6.84 (dd, J=18.4, 8.3 Hz, 2H), 6.04 (q, J=7.0 Hz, 1H), 3.99 (s, 2H), 3.92-3.68 (m, 5H), 1.55 (d, J=7.1 Hz, 3H). $^{13}$C NMR (75 MHz, CDCl$_3$) δ 166.8, 159.1, 144.1, 141.2, 138.2, 132.0, 129.8, 129.7, 128.9, 128.6, 128.3, 128.1, 127.9, 127.5, 125.4, 114.0, 55.3, 51.4, 42.4, 41.9, 16.6.

(R)—N-(3,3-Diphenylallyl)-N-(1-(4-methoxyphenyl)ethyl)-2-(4-methylpiperazin-1-yl)acetamide (20)

Compound 20 (106 mg, 44%) was prepared by a similar procedure to that of compound 11a from 19. The title compound was obtained as a yellow oil. $^1$H NMR (300 MHz, CDCl$_3$) δ 7.42-7.30 (m, 3H), 7.29-6.99 (m, 9H), 6.80 (dd, J=20.6, 8.7 Hz, 2H), 6.09-5.92 (m, 1H), 5.57 (dt, J=79.7, 6.6 Hz, 1H), 3.98 (ddd, J=13.9, 8.6, 5.9 Hz, 1H), 3.89-3.58 (m, 4H), 3.44-2.86 (m, 2H), 2.68-2.24 (m, 11H), 1.49 (dd, J=13.1, 7.0 Hz, 3H). $^{13}$C NMR (75 MHz, CDCl$_3$) δ 169.5, 169.0, 158.8, 143.1, 142.1, 141.7, 138.5, 132.9, 129.9, 128.8, 128.3, 128.2, 128.1, 127.9, 127.8, 127.6, 127.5, 127.4, 127.2, 126.7, 113.8, 62.2, 60.6, 55.3, 55.0, 54.8, 53.2, 50.5, 45.8, 41.8, 29.7, 16.9. HRMS (ESI) calcd for C$_{31}$H$_{38}$N$_3$O$_2$ 484.2964 (M+H)+, found 484.2976.

(R)—N-(3-Chloropropyl)-N-(1-(4-methoxyphenyl) ethyl)-3,3-diphenylprop-2-en-1-amine (21)

Compound 21 (101 mg, 24%) was prepared by a similar procedure to that of compound 11a from 1-bromo-3-chloropropane with DIPEA as the base. The title compound was obtained as a yellow oil. $^1$H NMR (300 MHz, CDCl$_3$) δ 7.28 (m, 10H), 6.85 (d, J=7.9 Hz, 2H), 6.21 (t, J=6.4 Hz, 1H), 3.95-3.85 (m, 1H), 3.82 (s, 3H), 3.66-3.48 (m, 2H), 3.28-3.10 (m, 2H), 2.70-2.44 (m, 2H), 1.91-1.70 (m, 2H), 1.29 (d, J=6.8 Hz, 3H). $^{13}$C NMR (75 MHz, CDCl$_3$) δ 158.4, 143.1, 142.4, 139.7, 136.0, 130.8, 129.9, 128.7 (2C), 128.4, 128.2, 128.1, 127.4, 127.2 (2C), 113.4, 58.4, 55.2, 48.8, 46.8, 43.3, 30.8, 16.4.

(R)—N-(1-(4-Methoxyphenyl)ethyl)-N-(3-(4-methylpiperazin-1-yl)propyl)-3,3-diphenylprop-2-en-1-amine (22)

Compound 22 (29 mg, 60%) was prepared by a similar procedure to that of compound 11a from 21. The title compound was obtained as a yellow oil. $^1$H NMR (300 MHz, CDCl$_3$) δ 7.40-7.19 (m, 10H), 7.14 (d, J=6.8 Hz, 2H), 6.82 (d, J=8.5 Hz, 2H), 6.23-6.16 (m, 1H), 3.85 (q, J=6.2 Hz, 1H), 3.80 (s, 3H), 3.19 (m, 2H), 2.65-2.21 (m, 12H), 2.28 (s, 3H), 1.61-1.45 (m, 2H), 1.24 (d, J=6.6 Hz, 3H). $^{13}$C NMR (75 MHz, CDCl$_3$) 158.2, 142.7, 142.5, 139.7, 136.5, 129.9, 128.7, 128.5, 128.1, 128.0, 127.3, 127.1 (2C), 113.3, 58.4, 56.6, 55.2, 55.1, 53.2, 48.7, 47.8, 46.1, 24.7, 16.9. HRMS (ESI) calcd for C$_{32}$H$_{42}$N$_3$O 484.3328 (M+H)+, found 484.3325.

(R)—N-(3,3-Diphenylallyl)-4,4-diethoxy-N-(1-(4-methoxyphenyl)ethyl)butan-1-amine (23)

Compound 23 (420 mg, 43%) was prepared by a similar procedure to that of compound 11a from 4-chlorobutyraldehyde diethyl acetal. The title compound was obtained as a yellow oil. $^1$H NMR (300 MHz, CDCl$_3$) δ 7.43-7.31 (m, 3H), 7.29-7.19 (t, J=8.8 Hz, 7H), 7.14 (d, J=6.3 Hz, 2H), 6.82 (d, J=7.3 Hz, 2H), 6.22 (d, J=6.0 Hz, 1H), 4.39 (t, J=6.0 Hz, 1H), 3.86 (q, J=6.0 Hz, 1H), 3.81 (s, 3H), 3.68-3.54 (m, 2H), 3.52-3.37 (m, 2H), 3.25-3.09 (m, 2H), 2.54-2.31 (m, 2H), 1.61-1.50 (m, 2H), 1.47-1.36 (m, 2H), 1.28-1.18 (m, 9H). $^{13}$C NMR (75 MHz, CDCl$_3$) δ 158.2, 142.7, 142.5, 139.8, 136.5, 129.9, 128.7, 128.1, 128.0, 127.3, 127.1, 113.3, 102.9, 60.9, 60.8, 58.4, 55.2, 49.4, 48.7, 31.3, 22.6, 16.7, 15.4. HRMS (ESI) calcd for C$_{32}$H$_{42}$NO$_3$ 488.3165 (M+H)$^+$, found 488.3165.

(R)-4-((3,3-Diphenylallyl)(1-(4-methoxyphenyl) ethyl)amino)butanal (24)

To a solution of compound 23 (300 mg, 0.62 mmol) in 1,4-dioxane (9 mL) was added 6 N HCl (9 mL) at 0° C. The mixture was stirred at 50° C. for 2 h. After cooling to rt, the mixture was poured into cold NH₄OH aq. and extracted with EtOAc (20 mL×2). The combined EtOAc extracts were washed with brine, dried Na₂SO₄, filtered, and condensed by rotary evaporation. The residue was further purified by preparative TLC plates to give 24 (236 mg, 92%) as a yellow oil. $^1$H NMR (300 MHz, CDCl₃) δ 9.71 (t, J=1.7 Hz, 1H), 7.40-7.17 (m, 12H), 6.89-6.81 (m, 2H), 6.21 (t, J=6.7 Hz, 1H), 3.91 (q, J=6.8 Hz, 1H), 3.82 (s, 3H), 3.21 (t, J=6.6 Hz, 2H), 2.52-2.31 (m, 4H), 1.75-1.59 (m, 2H), 1.26 (d, J=6.8 Hz, 3H). $^{13}$C NMR (75 MHz, CDCl₃) δ 202.6, 158.4, 143.3, 142.4, 139.7, 135.9, 129.9, 128.8, 128.2, 128.1, 127.9, 127.4, 127.2 (2C), 113.4, 58.2, 55.2, 48.6, 48.5, 41.7, 20.5, 16.2.

(R)—N-(3,3-Diphenylallyl)-N-(1-(4-methoxyphenyl)ethyl)-4-(4-methylpiperazin-1-yl)butan-1-amine (25)

Compound 25 (26 mg, 52%) was prepared by a similar procedure to that of compound 11b from 24. The title compound was obtained as a colorless oil. $^1$H NMR (300 MHz, CDCl₃) δ 7.41-7.32 (m, 3H), 7.29-7.21 (m, 7H), 7.14 (dd, J=7.7, 1.7 Hz, 2H), 6.82 (d, J=8.7 Hz, 2H), 6.21 (t, J=6.6 Hz, 1H), 3.84 (t, J=6.6 Hz, 1H), 3.81 (s, 3H), 3.18 (dd, J=6.4, 5.4 Hz, 2H), 2.60-2.32 (m, 10H), 2.30 (s, 3H), 2.29-2.23 (m, 2H), 1.46-1.31 (m, 4H), 1.25 (d, J=6.7 Hz, 3H). $^{13}$C NMR (75 MHz, CDCl₃) δ 158.2, 142.7, 142.5, 139.8, 136.6, 129.9, 128.7, 128.6, 128.1, 128.0, 127.3, 127.1 (2C), 113.3, 58.6, 58.5, 55.2, 55.1, 53.2, 49.6, 48.7, 46.1, 25.3, 24.7, 17.0. FIRMS (ESI) calcd for $C_{33}H_{44}N_3O$ 498.3484 (M+H)+, found 498.3475.

3.0. Method of Use

The inventors surprisingly discovered compounds of the invention, as exemplified by e.g., compounds NY0244, NY0331, NY0506 and PW0323, modulate KRAS activity.

In some embodiments, the invention encompasses a method of modulating KRAS activity in a subject comprising contacting one or more cells of said subject with a therapeutic amount of one or more compounds of Formula I and/or Formula II, or a pharmaceutically acceptable salt thereof.

In some embodiments, the invention encompasses a method of inhibiting KRAS activity in a subject comprising contacting one or more cells of said subject with a therapeutic amount of one or more compounds of Formula I and/or Formula II, or a pharmaceutically acceptable salt thereof.

In some embodiments, the invention encompasses a method of treating a K-Ras mediated disorder (such as various cancers and inflammatory diseases) in a subject in need thereof, said method comprising administering a therapeutic amount of one or more compounds of Formula I and/or Formula II, or a pharmaceutically acceptable salt thereof.

Preliminary findings indicate that the fendiline derivative NY331 synergizes with MAPK pathway inhibitors such as, but not limited to, trametinib, to enhance the efficacy.

The described fendiline derivatives without regard to any particular KRAS mutation. Erlotinib is an oral reversible inhibitor of EGFR tyrosine kinase, that improves progression free and overall patient survival when used as a combination therapy, as compared to gemcitabine alone. However, unlike the fendiline derivatives of the invention, certain KRAS mutations are generally associated with less efficient therapy. The fendiline derivatives of the invention, may be used alone, or in combination with, but not limited to, abraxane, gemcitabine, erlotinib (EGFR tyrosine kinase inhibitors), trametinib (MAPK pathway inhibitors) and the ceramide analog inhibitors of UDP-glucose glucosylceramide transferase: DMPM; eliglustat; and tamoxifen.

Further evidence of synergy has been observed using exemplary embodiment of the invention, in combination with PI4KIIIa inhibitors. Such inhibitors include but are not limited to Hepatitis C virus antiviral agent, simeprevir, as well as compound 7. It has also been demonstrated that fendiline inhibits the growth of MiaPaCa2 xenografts in nude mice and that the fendiline derivatives NY244, NY331, NY506 and PW323 were all more potent than fendiline in the minimum effective dose required to tumor growth.

4.0 EXAMPLES

Example 1

Materials and Methods

General. All commercially available starting materials and solvents were reagent grade and used without further purification. Reactions were performed under a nitrogen atmosphere in dry glassware with magnetic stirring. Preparative column chromatography was performed using silica gel 60, particle size 0.063-0.200 mm (70-230 mesh, flash). Analytical TLC was carried out employing silica gel 60 F254 plates (Merck, Darmstadt). Visualization of the developed chromatograms was performed with detection by UV (254 nm). NMR spectra were recorded on a Bruker-600 ($^1$H, 300 MHz; $^{13}$C, 75 MHz) spectrometer. $^1$H and $^{13}$C NMR spectra were recorded with TMS as an internal reference. Chemical shifts downfield from TMS were expressed in ppm, and J values were given in Hz. High-resolution mass spectra (HRMS) were obtained from Thermo Fisher LTQ Orbitrap Elite mass spectrometer. Parameters include the following: nano ESI spray voltage was 1.8 kV, capillary temperature was 275° C., and the resolution was 60000; ionization was achieved by positive mode. Purity of final compounds was determined by analytical HPLC, which was carried out on a Shimadzu HPLC system (model: CBM-20A LC-20AD SPD-20A UV/vis). HPLC analysis conditions: Waters μBondapak C18 (300 mm×3.9 mm), flow rate 0.5 mL/min, UV detection at 270 and 254 nm, linear gradient from 10% acetonitrile in water (0.1% TFA) to 100% acetonitrile (0.1% TFA) in 20 min, followed by 30 min of the last-named solvent. All biologically evaluated compounds are >95% pure.

Cell Lines

Madine Darby Canine Kidney epithelial cells (MDCK) stably co-expressing mGFP-tagged full length oncogenic mutant K-Ras (GFP—K-RASG12V) or mGFP-LactC2 (peptide probe for phosphatidylserine) and mCherry-tagged to the amino acids 179-189 of H-RasC181S, C184S (mCherry-CAAX, localizes primarily to endomembranes) were grown in DMEM-high glucose/sodium pyruvate/10% FBS. The medium was supplemented with 1× Penicillin/Streptomycin for fluorescence microscopy assays, to avoid any microbial contamination from the test compounds added. KLE and Hec50 cells were maintained in DMEM-F-12 medium supplemented with 10% FBS. Hec-1A and Hec-1B cells were grown in McCoy's 5a medium supplemented with 10% FBS. ESS-1 cells were grown in RPMI 1640 medium supplemented with 20% FBS. MPanc96 cells were grown in DMEM supplemented with 10% FBS, MiaPaCa-2 cells in DMEM supplemented with 10% FBS and 2.5% horse serum and all other cell lines were grown in RPMI 1640 supplemented with 10% FBS. All cancer cell media were supplemented with ×Penicillin/Streptomycin. All cell lines were grown at 37° C. with 5% $CO_2$.

K-Ras/LactC2 Mislocalization Assay

MDCK co-expressing GFP—K-RASG12V or LactC2 and mCherry-CAAX were grown on coverslips, treated with 0.1% vehicle (DMSO) or various concentrations of drugs for 48 h, and fixed with 4% paraformaldehyde. The coverslips were mounted in mowiol and imaged by confocal microscopy (Nikon A1) using a 60× objective. Using ImageJ software v1.42q, images were converted to 8-bit, and a threshold to a control pixel of each image was set. As a measure of K-Ras/LactC2 mislocalization, the fraction of mCherry-CAAX co-localizing with mGFP-K-RASG12V was calculated using a Manders coefficient plugin downloaded from Wright Cell Image Facility. The fraction of mCherry-CAAX co-localizing with mGFP-RASG12V (Mander's coefficient) is proportional to K-Ras mislocalization.

Proliferation Assay

Cells were seeded in 96-well plates. After 24 h, fresh growth medium supplemented with 0.1% vehicle (DMSO), or various concentrations of drugs was added and cells were grown for 72 h. Cell numbers were quantified using the CyQUANT® Cell Proliferation Assay Kit (Molecular Probes, Life Technologies), according to the manufacturer's protocol. Fluorescence measurement was used as a measure of live cell number.

Cell Permeability/P-gp Substrate Assay

MDCK cells expressing human MDR1 gene (encodes P-gp, an important drug transporter) were grown as monolayers in 12-multiwell Transwell systems. 72 h post-seeding, drugs were added to apical or basolateral sides and incubated for 90 min following which both apical and basolateral samples were analyzed by LC-MS/MS. Permeability coefficients (Papp) of drugs from apical to basolateral (Papp, A>B) and basolateral to apical (Papp B>A) and Efflux Ratios were calculated. Efflux Ration of >2 indicates drug efflux by P-gp. Assay was conducted by Alliance Pharma, Inc.

CYP450 Inhibition Assay

Activities of major human CYP1A2, CYP2C9, CYP2C19, CYP2D6 and CYP3A4 isozymes in human liver microsomes were measured in the presence of drugs using isoform-specific probe substrates. Assay was conducted by Alliance Pharma, Inc.

ASM Activity Assay. The ASM activity assay was performed with Amplex Red SMase Assay Kit (A12220; Invitrogen; Carlsbad, CA) according to the manufacturer's instructions. Briefly, 10 µg of whole-cell lysates (at 1 µg/µL concentration) from MDCK cells stably expressing human ASM (SMPD1)-GFP prepared in lysis buffer B without DTT was mixed with 40 µL of low-pH buffer (50 mM sodium acetate, pH 5.0), and loaded on a well of black 96-well plate. 5 µL of 5 mM sphingomyelin was added to each well, and the plate was incubated in dark in 37° C. for 1 h. After the incubation, the pH was raised to 7.4 by adding 50 µL of Amplex Red reaction mixture [100 µM Amplex Red reagent, 2 U/mL horseradish peroxidase, 0.2 U/mL choline oxidase, 8 U/mL alkaline phosphatase in high-pH buffer (100 mM Tris-HCl, pH 8.0)]. The plate was further incubated in the dark in 37° C. for 60 min, and the fluorescence was measured using BioTek Synergy H1 microplate reader (excitation $\lambda$=540 nm, emission $\lambda$=590 nm). 0.1 U/mL SMase and low-pH buffer were used as a positive and negative control, respectively. Human SMPD1 cDNA (Cat #OHu18710D) was purchased from GenScript.

Western Blotting. Cells treated with vehicle or compounds for 48 h were washed in cold phosphate-buffered saline (PBS) and lysed in buffer containing 50 mM TrisCl (pH 7.5), 75 mM NaCl, 25 mM NaF, 5 mM MgCl2, 5 mM EGTA, 1 mM dithiothreitol, 100 µM NaVO4, 1% NP40 plus protease inhibitors. SDS-PAGE and immunoblotting were performed using lysates containing 20 µg of total protein. Signals were detected by enhanced chemiluminescence (Thermo Fisher Scientific) and imaged using a FluorChemQ imager (Alpha Inotech). Quantification of intensities was performed using FluorChemQ software.

ASM Add Back Assay. 1.75×105 MDCK cells stably co-expressing mGFP-KRASG12V and mCherry-CAAX were seeded on a glass coverslip in a 12-well plate and grown with or without compounds for 48 h. Medium was replaced with fresh medium with or without compounds containing 2 units/mL ASM and the incubation was continued for 60 minutes. The coverslips were mounted in mowiol and imaged by confocal microscopy (Nikon A1) using a 60×objective.

C. elegans Vulva Quantification Assay. Strain let-60 or lin-1 L1 larvae were cultured in M9 buffer containing Escherichia coli (E. coli) OP50 in presence of DMSO or compounds. After 4-5 days, when worms reached the adult stage, they were scored for the presence of the multi-vulva phenotype using a DIC/Nomarski microscope.

In Vivo Tumor Growth Assay. All animal studies were performed under an Institutional Animal Care and Use Committee (IACUC) approved animal protocol (AWC-15-0101), in accordance with the National Institutes of Health Guide for the Care and Use of Laboratory Animals. Early passage MiaPaCa-2 cells were harvested, and 2×106 cells were implanted into the right flanks of female nu/nu mice. The animals were randomized into control and treated groups (10 mice per group). Tumor volume (V) was measured with an external caliper every 3-4 days and it was calculated as V=0.52 (length×width2). Compound treatment was initiated when the tumor sizes reached 100 mm3. Compounds (12.5 mg/kg) were injected daily intraperitoneally for 5 days, with 2 days of no treatment in between. All treatments were continued until any of the subcutaneous tumors reached 1500 mm3 in volume, when all the animals were sacrificed, and the tumors removed.

In some instances the following in vivo tumor growth assay was used:

Early passage BxPC-3 or MIAPaCa-2 cells were harvested, and 2-3X106 cells were implanted into the right flanks of nu/nu mice. The animals were randomized into control and treated groups (10 mice per group). Tumor volume (V) was measured with an external caliper every 3-4 days and it was calculated as V=0.52 (length×width2). Drug treatment was initiated 4 days after tumor implantation. Drugs were injected daily intraperitoneally (at doses indicated) for 5 days, with 2 days of no treatment in between. All treatments were continued until any of the subcutaneous tumors reached 1500 mm3 in volume or for 6 weeks (whichever was first), when all the animals were sacrificed and the tumors removed.

Immunohistochemistry. 4-5 µm sections were deparaffinized, rehydrated, and treated with 10 mM sodium citrate for heat induced antigen retrieval. After quenching endogenous peroxidase, and blocking with 2.5% normal goat serum (Vector Laboratories S-1012), sections were incubated overnight at 4° C. with primary antibody diluted in blocking solution as recommended by manufacturer (Cell Signaling). Controls were incubated with diluted normal rabbit IgG. After incubation with biotinylated secondary antibody diluted 1:250 in blocking serum for 45 min at rt, sections were incubated with VECTASTAIN ABC reagent for 30 min, and for development of the DAB chromogen the Quanto substrate was used. Slides were counter stained with Hematoxylin. Five fields per stained section per xenograft were photographed at 10X. CC3+ and pERK+ area and number of events per field were quantitated via automated image analysis (NIS Elements BR analysis ver. 4.13.04). Vessel number and lumen area per field used the same software with manual settings to trace vessel wall contours. Antibodies used are as follows: CC3: Cell Signaling #9661, use at 1:300. (Cleaved Caspase-3 (Asp175) Antibody. Rabbit polyclonal. pERK: Cell Signaling #4370: Phospho-p44/42 MAPK (Erk1/2) (Thr202/Tyr204) (D13.14.4E) XP Rabbit mAB. CD31 (PECAM-1) (D8V9E) XP Rabbit mAB (Cell signal # (Cell signal #77699). Normal rabbit IgG: Santa Cruz #sc-3888. Concentration is 50 µg/mL or 50 ng/µL. Prepared with 5 µg in 200 µL blocking solution. Goat Anti-Rabbit IgG Biotin Conjugate: Calbiochem #OS03B, Concentration=1.2 mg/mL. Recommended to be used for IHC at 1 µg/mL.

Lysenin Staining of Tumor Sections. To label intracellular SM, 3 µm thick cryosections, fixed in 4% paraformaldehyde and quenched in 0.1 M NH4Cl, were permeabilized with 0.5% saponin before overnight incubation (4° C.) with MBP-GFP Lysenin (50 µg/mL) in PBS with 0.5% saponin containing DAPI (5 ng/mL). Samples mounted in FluorSave were photographed in the Nikon AIR Confocal Laser Microscope. GFP-Lysenin binding was quantitated using NIS Elements BR analysis ver. 4.13.04. The average value obtained in the negative control pictures (background) was subtracted from each of the GFP pictures (n=20).

TABLE 1

Potency and efficacy of K-RAS inhibition and toxicity of batch 1 and 2 compounds. MDCK cells co-expressing GFP-K-RASG12V and mCherry-CAAX were grown on coverslips, treated with 0.1% vehicle (DMSO) or various concentrations of drugs (A; batch 1, B; batch 2) for 48 h, and fixed with 4% paraformaldehyde. The coverslips were mounted in mowiol and imaged by confocal microscopy (Nikon A1) using a 60x objective. Using ImageJ software v1.42q, images were converted to 8-bit, and a threshold to a control pixel of each image was set. As a measure of K-Ras mislocalization, the fraction of mCherry-CAAX co-localizing with mGFP-K-RASG12V was calculated using a Manders coefficient plugin downloaded from Wright Cell Image Facility. Dose-response curves (three parameter fitting) were plotted using GraphPad Prism and IC50 and Emax values were calculated using the software. Toxicity was based on whether the drug caused death of all cells in well at 30 µM concentration.

| Compound ID | IC$_{50}$ (µM) | E$_{max}$ | Cytotoxic at 30 µM |
|---|---|---|---|
| A. (Screen-Batch 1 Compounds) | | | |
| AVA08 (R-Fendiline) | 5.59 | 0.811 | Yes |
| AVA72 (See cpd. 72 in US20150344407A1) | 0.17 | 0.764 | No |
| NY0217 | 13.0 | 0.47 | No |
| NY0218 | 3.3 | 0.75 ± 0.01 | No |
| NY0220 | 3.65 | 0.605 | No |
| NY0221 | 0.65 | 0.585 | No |
| NY0222 | 0.25 | 0.587 | Yes |
| NY0223 | 8.45 | 0.785 | No |
| NY0224 | 0.64 | 0.622 | No |
| NY0225 | 0.43 | 0.626 | Yes |
| NY022601 | 0.42 | 0.713 | No |
| NY022602 | 0.16 | 0.637 | No |
| NY022701 | ND | 0.494 | No |
| NY022702 | 16.87 | 0.608 | No |
| NY0228 | ND | 0.705 | No |
| NY0229 | 6.39 | 0.522 | No |
| NY0232 | 1.1 | 0.73 ± 0.02 | No |
| NY0233 | 3.56 | 0.522 | No |
| NY0234 | 21.91 | 0.703 | No |
| NY0235 | 1.21 | 0.59 | No |
| NY0237 | 12.18 | 0.79 | No |
| NY0241 | 0.2 | 0.72 ± 0.03 | No |
| NY0244 | 0.1 | 0.75 ± 0.01 | Yes |
| B. ((Screen-Batch 2 Compounds) | | | |
| AVA08 (R-Fendiline) | 5.59 | 0.811 | Yes |
| AVA72 (See cpd. 72 in US20150344407A1) | 0.17 | 0.764 | No |
| NY0244 | 0.1 | 0.75 ± 0.01 | Yes |
| NY244a | 0.19 | 0.918 | Yes |
| NY247 | 1.76 | 0.646 | No |
| NY293 | 2.30 | 0.910 | No |
| NY304 | 2.95 | 0.751 | No |
| NY306 | 3.95 | 0.893 | No |
| NY307 | 4.20 | 0.858 | No |
| NY314 | 1.69 | 0.842 | No |
| NY315 | 10.1 | 0.52 ± 0.04 | No |
| NY316 | 4.4 | 0.86 ± 0.02 | No |
| NY325 | 7.7 | 0.81 ± 0.02 | No |
| NY329 | 0.6 | 0.83 ± 0.02 | Yes |
| NY331 | 0.3 | 0.85 ± 0.02 | Yes |
| NY335 | 0.02 | 0.81 ± 0.01 | Yes |

TABLE 1-continued

Potency and efficacy of K-RAS inhibition and toxicity of batch 1 and 2 compounds. MDCK cells co-expressing GFP-K-RASG12V and mCherry-CAAX were grown on coverslips, treated with 0.1% vehicle (DMSO) or various concentrations of drugs (A; batch 1, B; batch 2) for 48 h, and fixed with 4% paraformaldehyde. The coverslips were mounted in mowiol and imaged by confocal microscopy (Nikon A1) using a 60× objective. Using ImageJ software v1.42q, images were converted to 8-bit, and a threshold to a control pixel of each image was set. As a measure of K-Ras mislocalization, the fraction of mCherry-CAAX co-localizing with mGFP-K-RASG12V was calculated using a Manders coefficient plugin downloaded from Wright Cell Image Facility. Dose-response curves (three parameter fitting) were plotted using GraphPad Prism and IC50 and Emax values were calculated using the software. Toxicity was based on whether the drug caused death of all cells in well at 30 µM concentration.

| Compound ID | IC$_{50}$ (µM) | E$_{max}$ | Cytotoxic at 30 µM |
|---|---|---|---|
| NY345 | 0.329 | 0.819 | No |
| NY346 | 14.8 | 0.84 ± 0.01 | No |
| NY347 | 1.3 | 0.86 ± 0.02 | Yes |
| NY348 | 5.47 | 0.963 | No |
| NY349 | 59.3 | 0.76 ± 0.02 | No |
| NY350 | — | 0.877 | No |
| NY351 | 1.11 | 0.851 | No |
| NY352 | 1.68 | 0.920 | Yes |
| NY353 | 3.26 | 0.920 | No |
| NY356 | 4.19 | 0.886 | No |

TABLE 2

Summary of IC50 values of selected round 1 and 2 compounds in proliferation assays. Potency of batch ½ compounds to inhibit proliferation of K-RAS-transformed cancer cells. A panel of wild-type (WT) or oncogenic mutant KRAS-expressing (Mut) pancreatic (A), lung (B), endometrial (C) or colon (D) tumor cells were seeded in 96-well plates and treated for 72 h with vehicle (DMSO) or various concentrations of fendiline, AVA68, NY0244, NY0331 or NY0335. The number of viable cells was quantified using the CyQuant cell proliferation assay kit (Molecular Probes).

A.

| Pancreatic | BxPC-3 (WT) | MiaPaCa-2 (Mut) | MOH (Mut) | MPanc96 (Mut) | HPAC (Mut) |
|---|---|---|---|---|---|
| Fendiline | 28.58 | 9.17 | 11.11 | 10.76 | NT |
| AVA68 | NE | NE | NE | NE | NT |
| NY0244 | 5.73 | 3.03 | 3.67 | 4.22 | 5.55 |
| NY0331 | NT | 3.36 | 3.55 | 3.81 | 5.15 |
| NY0335 | 5.34 | 2.79 | 3.77 | 4.18 | 5.81 |

B.

| Lung | NCI H1975 (WT) | NCI H522 (WT) | NCI-H1299 (WT) | NCI-H23 (Mut) |
|---|---|---|---|---|
| Fendiline | NE | 29.6 | 24.25 | 11.39 |
| AVA68 | NE | NE | NE | NE |
| NY0244 | NE | 28.2 | 8.24 | 3.81 |
| NY0335 | NE | 23.5 | 8.12 | 4.14 |

C.

| Endometrial | KLE (WT) | ESS-1 (WT) | Ishikawa (WT) | Hec1A (Mut) | Hec1B (Mut) |
|---|---|---|---|---|---|
| Fendiline | NE | NE | NE | 9.48 | 9.8 |
| AVA68 | NE | NE | NE | NE | NE |
| NY0244 | NE | NE | NE | 2.6 | 3.28 |
| NY0335 | NE | NE | 10.99 | 2.34 | 3.89 |

TABLE 2-continued

Summary of IC50 values of selected round 1 and 2 compounds in proliferation assays. Potency of batch ½ compounds to inhibit proliferation of K-RAS-transformed cancer cells. A panel of wild-type (WT) or oncogenic mutant KRAS-expressing (Mut) pancreatic (A), lung (B), endometrial (C) or colon (D) tumor cells were seeded in 96-well plates and treated for 72 h with vehicle (DMSO) or various concentrations of fendiline, AVA68, NY0244, NY0331 or NY0335. The number of viable cells was quantified using the CyQuant cell proliferation assay kit (Molecular Probes).

| Colon | D. | |
|---|---|---|
| | CaCO-2 (WT) | SK-CO-1 (Mut) |
| Fendiline | 15.41 | 7.77 |
| AVA68 | NE | NE |
| NY0244 | 5.10 | 3.28 |
| NY0335 | 4.43 | 3.52 |

NE—Not efficacious
NT—Not tested

TABLE 3

Potency and efficacy K-RAS inhibition and toxicity of batch 3 compounds. MDCK cells co-expressing GFP-K-RASG12V and mCherry-CAAX were grown on coverslips, treated with 0.1% vehicle (DMSO) or various concentrations of batch 3 compounds for 48 h, and fixed with 4% paraformaldehyde. The coverslips were mounted in mowiol and imaged by confocal microscopy (Nikon A1) using a 60× objective. Using ImageJ software v1.42q, images were converted to 8-bit, and a threshold to a control pixel of each image was set. As a measure of K-Ras mislocalization, the fraction of mCherry-CAAX co-localizing with mGFP-K-RASG12V was calculated using a Manders coefficient plugin downloaded from Wright Cell Image Facility. Dose-response curves (three parameter fitting) were plotted using GraphPad Prism and IC50 and Emax values were calculated using the software. Toxicity was based on whether the drug caused death of all cells in well at 30 μM concentration.
(Screen-Batch 3 Compounds)

| Compound | IC50 (μM) | Emax | Cytotoxic at 30 μM |
|---|---|---|---|
| NY0357a | 2.55 | 0.697 | Yes |
| NY0358 | 1.15 | 0.887 | Yes |
| NY0366 | 3.81 | 0.861 | Yes |
| NY0369b | 90.08 | 0.866 | Yes |
| NY0370b | 11.2 | 0.767 | Yes |
| NY0372 | 16.41 | 0.868 | No |
| NY040401 | 1.46 | 0.778 | No |
| NY040402 | 0.20 | 0.835 | No |
| NY0428 | 0.29 | 0.891 | No |
| NY0429 | 10.56 | 0.835 | No |
| NY0431 | 2.91 | 0.756 | No |
| NY0434 | 4.69 | 0.835 | No |
| NY0435 | 11.22 | 0.658 | Yes |
| NY0436 | 13.98 | 0.716 | No |
| NY0438 | 5.10 | 0.754 | No |
| NY0443 | 0.91 | 0..852 | Yes |
| NY0444 | 0.73 | 0.732 | Yes |
| NY0445 | 2.02 | 0.694 | No |
| NY0448 | 12.66 | 0.777 | Yes |
| NY0449 | ND | 0.810 | Yes |
| NY0452 | 2.81 | 0.752 | Yes |
| NY0454 | 1.24 | 0.827 | Yes |

TABLE 4

Potency of batch 3 compounds to inhibit proliferation of K-RAS-transformed cancer cells. A panel of wild-type (WT) or oncogenic mutant KRAS-expressing (Mut) pancreatic (A), lung (B), or endometrial (C) tumor cells were seeded in 96-well plates and treated for 72 h with vehicle (DMSO) or various concentrations of AVA NY0428, NY0443, NY0444, or NY040402. The number of viable cells was quantified using the CyQuant cell proliferation assay kit (Molecular Probes).

A.

| Pancreatic | BxPC-3 (WT) | MiaPaCa-2 (Mut) | MOH (Mut) | MPanc96 (Mut) |
|---|---|---|---|---|
| NY0428 | 13.99 | NE | NE | NE |
| NY0443 | 7.8 | 4.01 | 3.4 | 11.78 |
| NY0444 | 4.57 | 3.04 | 3.95 | 2.48 |
| NY040402 | NE | NE | NE | NE |

B.

| Lung | NCI H1975 (WT) | NCI H522 (WT) | NCI-H1299 (WT) | NCI-H23 (Mut) |
|---|---|---|---|---|
| NY0443 | NE | NE | 5.77 | 7.63 |
| NY0444 | 28.5 | 29.6 | 5.85 | 44 |

C.

| Endometrial | KLE (WT) | ESS-1 (WT) | Ishikawa (WT) | Hec1A (Mut) | Hec1B (Mut) |
|---|---|---|---|---|---|
| NY0443 | 12.95 | NE | NE | 6.07 | 3.22 |
| NY0444 | 7.97 | NE | NE | 1.59 | 2.46 |

NE—Not efficacious
NT—Not tested

TABLE 5

Potency and efficacy of K-RAS inhibition and toxicity of batch 4 compounds. MDCK cells co-expressing GFP-K-RASG12V and mCherry-CAAX were grown on coverslips, treated with 0.1% vehicle (DMSO) or various concentrations of batch 4 compounds for 48 h, and fixed with 4% paraformaldehyde. The coverslips were mounted in mowiol and imaged by confocal microscopy (Nikon A1) using a 60× objective. Using ImageJ software v1.42q, images were converted to 8-bit, and a threshold to a control pixel of each image was set. As a measure of K-Ras mislocalization, the fraction of mCherry-CAAX co-localizing with mGFP-K-RASG12V was calculated using a Manders coefficient plugin downloaded from Wright Cell Image Facility. Dose-response curves (three parameter fitting) were plotted using GraphPad Prism and IC50 and Emax values were calculated using the software. Toxicity was based on whether the drug caused death of all cells in well at 30 μM concentration.

| Compound | EC50 | Emax | Cytotoxic |
|---|---|---|---|
| (Part 1) | | | |
| NY0473 | 0.376 | 0.891 | Yes |
| NY0479 | 1.59 | 0.871 | No |
| NY0483 | 0.387 | 0.977 | Yes |
| NY0502 | 1.78 | 0.878 | Yes |
| NY0504 | 0.91 | 0.845 | No |
| NY0505 | 1.51 | 0.832 | Yes |
| NY0506 | 0.528 | 0.808 | Yes |
| NY0507 | 1.69 | 0.858 | No |
| NY0513 | 0.639 | 0.786 | Yes |
| NY0514 | 1.34 | 0.802 | No |
| NY0518 | 3.84 | 0.695 | Yes |
| NY0519 | 4.36 | 0.553 | Yes |
| NY0521 | ND | 0.816 | No |
| NY0522 | 5.17 | 0.621 | Yes |
| NY055101 | 8.91 | 0.424 | Yes |
| NY055102 | ND | 0.424 | No |
| NY0552 | 4.05 | 0.426 | No |
| NY0553 | ND | 0.452 | No |
| NY0554 | 1.2 | 0.327 | Yes (even at 10 μM) |
| (Part 2) | | | |
| NY0555 | 4.37 | 0.332 | No |
| NY0557 | ND | 0.732 | No |
| NY0566 | 5.93 | 0.718 | No |
| NY0568 | ND | 0.364 | No |
| NY0569 | ND | 0.321 | No |
| NY0570 | ND | 0.397 | No |
| NY0572 | ND | 0.565 | No |
| NY0573 | 1.75 | 0.733 | No |
| NY0574 | 4.82 | 0.842 | No |
| NY0575 | 4.3 | 0.484 | No |

TABLE 5-continued

Potency and efficacy of K-RAS inhibition and toxicity of batch 4 compounds. MDCK cells co-expressing GFP-K-RASG12V and mCherry-CAAX were grown on coverslips, treated with 0.1% vehicle (DMSO) or various concentrations of batch 4 compounds for 48 h, and fixed with 4% paraformaldehyde. The coverslips were mounted in mowiol and imaged by confocal microscopy (Nikon A1) using a 60× objective. Using ImageJ software v1.42q, images were converted to 8-bit, and a threshold to a control pixel of each image was set. As a measure of K-Ras mislocalization, the fraction of mCherry-CAAX co-localizing with mGFP-K-RASG12V was calculated using a Manders coefficient plugin downloaded from Wright Cell Image Facility. Dose-response curves (three parameter fitting) were plotted using GraphPad Prism and IC50 and Emax values were calculated using the software. Toxicity was based on whether the drug caused death of all cells in well at 30 μM concentration.

| Compound | EC50 | Emax | Cytotoxic |
|---|---|---|---|
| NY0580 | 5.5 | 0.73 | No |
| NY0583 | 3.91 | 0.725 | No |
| NY0584 | 6.94 | 0.697 | No |
| NY0587 | 1.83 | 0.827 | No |
| NY0589 | 2.18 | 0.895 | Yes |
| NY0590 | 0.945 | 0.893 | Yes |
| NY0591 | ND | 0.825 | No |
| NY0592 | 5.6 | 0.685 | Yes |
| NY0593 | 0.492 | 0.694 | Yes |
| NY0594 | 3.26 | 0.75 | Yes |

TABLE 6

Potency of batch 4 compounds to inhibit proliferation of K-RAS-transformed cancer cells. A panel of wild-type (WT) or oncogenic mutant KRAS-expressing (Mut) pancreatic (A), lung (B), endometrial (C) or colon (D) tumor cells were seeded in 96-well plates and treated for 72 h with vehicle (DMSO) or various concentrations of NY0506, NY0513, NY0590 or NY0593. The number of viable cells was quantified using the CyQuant cell proliferation assay kit (Molecular Probes).

A.

| Pancreatic | NY0506 | NY0513 | NY0590 | NY0593 |
|---|---|---|---|---|
| BxPC-3 (WT) | 10.6 | 13.8 | NE | 10.8 |
| MiaPaCa-2 (Mut) | 11.5 | 2.1 | 26.2 | 5.8 |
| MOH (Mut) | 10.6 | 5.1 | NE | 7.8 |
| HPAC (Mut) | 6.9 | 25.7 | NE | 9.3 |

B.

| Lung | NY0506 | NY0513 | NY0590 | NY0593 |
|---|---|---|---|---|
| H1925 (WT) | 4.0 | 17.7 | NE | 8.3 |
| H522 (WT) | 2.6 | 3.9 | NE | 9.6 |
| H1299 (N Mut) | 2.1 | 10.1 | 12.2 | 8.0 |
| H23 (Mut) | 6.8 | 1.6 | NE | 6.2 |

C.

| Endometrial | NY0506 | NY0513 | NY0590 |
|---|---|---|---|
| KLE (WT) | 10.6 | NE | NE |
| Ishikawa (WT but sensitive) | 0.6 | 10.2 | NE |
| Hec1A (Mut) | 0.2 | 2.1 | 24.7 |
| Hec1B (Mut) | 0.4 | 1.0 | 19.9 |

D.

| Colon | NY0506 | NY0513 | NY0590 | NY0593 |
|---|---|---|---|---|
| CaCO-2 (WT but sensitive) | 0.7 | 3.5 | 4.7 | 4.6 |
| SK-CO-1 (Mut) | 0.5 | 2.4 | 3.6 | 5.2 |
| SW948 (Mut) | 0.2 | 3.2 | 7.4 | 3.0 |
| SW1116 (Mut) | 0.3 | 11.2 | NE | 11.7 |

TABLE 7

Potency and efficacy of K-RAS inhibition and toxicity of batch 5 compounds. MDCK cells co-expressing GFP-K-RASG12V and mCherry-CAAX were grown on coverslips, treated with 0.1% vehicle (DMSO) or various concentrations of batch 5 compounds for 48 h, and fixed with 4% paraformaldehyde. The coverslips were mounted in mowiol and imaged by confocal microscopy (Nikon A1) using a 60× objective. Using ImageJ software v1.42q, images were converted to 8-bit, and a threshold to a control pixel of each image was set. As a measure of K-Ras mislocalization, the fraction of mCherry-CAAX co-localizing with mGFP-K-RASG12V was calculated using a Manders coefficient plugin downloaded from Wright Cell Image Facility. Dose-response curves (three parameter fitting) were plotted using GraphPad Prism and IC50 and Emax values were calculated using the software. Toxicity was based on whether the drug caused death of all cells in well at 30 μM concentration.

| Compound ID | IC50 (μM) | Emax | Cytotoxic at 30 μM |
|---|---|---|---|
| (Part 1) | | | |
| PW124 | 0.553 | 0.452 | Yes |
| PW125 | 7.09 | 0.514 | Yes |
| PW126 | 2.19 | 0.412 | Yes |
| PW2100 | ND | 0.414 | No |
| PW276 | 4.8 | 0.572 | Yes |
| PW277 | 3.97 | 0.592 | Yes |
| PW278 | 8.85 | 0.739 | Yes |
| PW279 | 3.4 | 0.608 | Yes |
| PW280 | 6.03 | 0.709 | Yes |
| PW282 | 12.49 | 0.592 | No |
| PW283 | ND | 0.324 | Yes |
| PW284 | ND | 0.549 | Yes |
| PW285 | 4.52 | 0.62 | Yes |
| PW286 | 6.63 | 0.801 | No |
| PW293 | 3.37 | 0.83 | Yes |
| PW295 | 2.82 | 0.801 | Yes |
| PW297 | 2.27 | 0.685 | No |
| PW299 | 0.654 | 0.696 | No |
| PW303 | 4.13 | 0.675 | Yes |
| (Part 2) | | | |
| PW304 | 2.77 | 0.794 | No |
| PW305 | 0.507 | 0.609 | Yes |
| PW306 | 3.19 | 0.666 | Yes |
| PW307 | ND | 0.628 | No |
| PW308 | 3.32 | 0.721 | No |
| PW321 | ND | 0.587 | No |
| PW322 | ND | 0.662 | No |
| PW323 | 0.05 | 0.852 | Yes |
| PW324 | 2.9 | 0.767 | No |
| PW327 | 7.8 | 0.808 | Yes |
| PW356 | 2.44 | 0.641 | Yes at 10 uM |
| PW357 | ND | 0.497 | Yes at 10 uM |
| PW358 | 1.02 | 0.938 | Yes |
| PW448 | 4.64 | 0.679 | Yes at 10 uM |
| PW454 | 0.319 | 0.771 | Yes at 10 uM |
| PW455 | 1.857 | 0.821 | Yes at 10 uM |
| PW460 | 2.02 | 0.801 | Yes at 10 uM |
| PW361 | 0.725 | 0.606 | Yes at 3 uM |

Example 2. In Vitro Evaluation of Potency and Efficacy of KRAS Mislocalization All newly synthesized compounds were evaluated for their ability to mislocalize GFP-tagged oncogenic mutant KRAS (mGFP-KRAS G12V) from the PM of MDCK cells to determine their potency ($IC_{50}$ values), efficacy ($E_{max}$) and cytotoxicity at 30 μM concentration. Compound 7 was used as the reference compound for comparison and the results were consistent with previously reported potency, with $IC_{50}$ values of 0.5 μM for KRAS mislocalization. In addition, we found a good correlation between cytotoxicity in this assay and their ability to kill the mutant KRAS expressing cancer cells, and therefore, the cytotoxicity at 30 μM concentration were indicated in the tables.

As shown in Table 8, we initially focused on improving aqueous solubility of 7 to improve the pharmacokinetic (PK) profiles. Therefore, we simply removed the diphenyl moiety of P3 and alkylated with a methyl group leading to compound 11a, and this resulted in a 7-fold loss of potency in comparison with 7 to mislocalize KRAS (IC50=3.3 μM). Extended length of the alkyl linker (e.g., compounds 11b and 11c) resulted in a further substantial loss of potency. However, the compound regained the activity with enhancement when a hydroxyl group (11e) was introduced, showing a 2.5-fold increase in KRAS mislocalization potency ($IC_{50}$=0.2 μM). Compound 11e displayed a similar efficacy to that of 7 ($E_{max}$=0.72) but a better cLogP (5.18 vs 9.32). Like compound 7, compound 11e did not show any cytotoxic at 30 μM. However, changing the hydroxyl group to a fluorine yielding compound 11f led to a 20-fold loss of potency ($IC_{50}$=10.1 μM). Comparing 12a to 11e, replacing the hydroxyl group with a dimethylamino group resulted in a dramatic decrease of both potency and efficacy. Conversely, when a diethylamino group (12b) or nitrogen contained 6-member ring (12c-e) was introduced, the potency equivalent to 11e was retained, while the efficacy was slightly improved. Compound 12e exhibited decent potency and excellent efficacy ($IC_{50}$=1.3 µM, Emax=0.90) as well as the cytotoxicity at 30 µM. Inspired by the result from 12e, we then started to modify on the piperazine ring by introducing a methyl group (12f (NY0244)) or an oxygen atom (12g). The results indicated that 12f (NY0244) was the best compound of this series with an $IC_{50}$ of 0.1 µM (5-fold more potent than hit 7), and slightly enhanced efficacy ($E_{max}$=0.75) as well. In addition 12f (NY0244) also has a better cLogP than that of 7, suggesting that it may have a better PK profile. Introducing an oxygen atom on the piperzine (12g, IC50=7.7 µM) is not tolerable, leading to a 6-fold potency loss compared to 12e. Decreasing the ring size (six-member piperazine ring) of 12f (NY0244) into a pyrrolidine ring (12h (NY0331)) or an azetidine ring (12i) showed 3-fold ($IC_{50}$=0.3 µM) and 5-fold ($IC_{50}$=0.5 µM) potency loss, respectively. In addition, compounds 14a and 14b with simplified side chain A2 and A3 resulted in a complete loss of in vitro activity, indicating that at least one diphenyl ring system is required to retain KRAS PM localization inhibition activity. Taken together, these results suggest that only one diphenyl ring system is necessary and the methylpiperazine motif is more favorable for KRAS mislocalization.

Methylpiperazine was kept intact as the P3 moiety and investigated the SAR of P1 moiety. The effect of the chiral methyl group on the in vitro activity was investigated. As shown in Table 9, compound 15a with an (S)-enantiomer was found to be less potent than its (R)-enantiomer (12f: (NY0244)), exhibiting 12-fold decreased potency with an IC50 of 1.2 µM, but with a slight improvement on efficacy ($E_{max}$=0.83). With the favorable R-configuration of methyl group, compounds 15b and 15c were synthesized to probe the impact of the position of methoxy group in the phenyl ring on the potency. As shown in Table 9, the methoxy group at the para-position is better than ortho- and meta-position. The diverse substituents on the phenyl ring of P1 moiety were also investigated and are summarized in Table 9. Replacement of the methoxy group with hydrogen, fluorine, chlorine or a nitro group (e.g., 15d~1h) led to 6- to 112-fold decrease in potency. One conclusion is that the (R)-enantiomer is more favorable than the (S)-enantiomer and the methoxy group impacts KRAS mislocalization potency. The substitutes and the positions also may influence KRAS inhibitory potency, with electron-donating substitutes preferred over electron-withdrawing groups, and substitution at the para-position is superior to that at the ortho- or meta-positions.

TABLE 8

The IC50 and Emax Values of (R)-N-Substituted-N-(1-(4-methoxyphenyl)ethyl)-3,3-diphenylprop-2-en-1-amine KRAS PMLIs

| Compound | $R^1$ | $R^3$ | $IC_{50}$ (µM)[a] | $E_{max}$[b] | cLogP[c] | Cytotoxic at 30 µM |
|---|---|---|---|---|---|---|
| 7 | A1 | A1 | 0.5 | 0.74 ± 0.03 | 9.32 | No |
| 11b | —Et | A1 | 10.6 | 0.84 ± 0.02 | 6.21 | No |
| 12a | 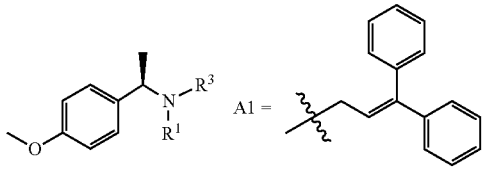 | A1 | 11.2 | 0.66 ± 0.01 | 5.75 | Yes |
| 12b | 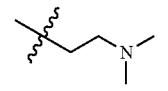 [SMILES: *CCN(C)C] | A1 | 1.2 | 0.89 ± 0.01 | 6.53 | Yes |
| 12i | 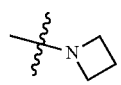 [SMILES: *N1CCC1] | A1 | 0.5 | 0.69 ± 0.02 | 5.90 | Yes |

TABLE 9

The IC50 and Emax Values of N-(1-(Substituted phenyl)ethyl)-N-(2-(4-methylpiperazin-1-yl)ethyl)-3,3-diphenylprop-2-en-1-amine KRAS compounds

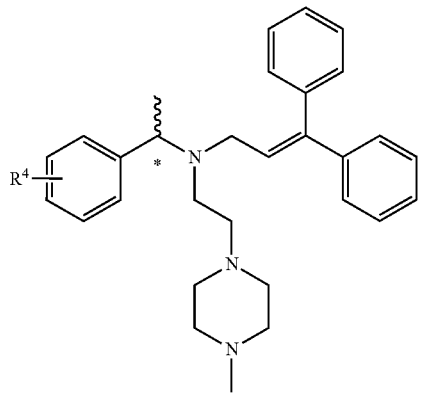

| Compound | R[4], * | IC$_{50}$ (μM)[a] | E$_{max}$[b] | cLogP[c] | Cytotoxic at 30 μM |
|---|---|---|---|---|---|
| 7 |  | 0.5 | 0.74 ± 0.03 | 9.32 | No |
| 12f (NY0244) | -4-OMe, (R) | 0.1 | 0.75 ± 0.01 | 5.44 | Yes |
| 15a | -4-OMe, (S) | 1.2 | 0.83 ± 0.02 | 5.44 | Yes |
| 15b | -2-OMe, (R) | 3.8 | 0.86 ± 0.01 | 5.44 | Yes |
| 15c | -3-OMe, (R) | 2.8 | 0.75 ± 0.04 | 5.44 | Yes |
| 15d | —H, (R) | 0.6 | 0.79 ± 0.01 | 5.43 | Yes |
| 15e | -4-F, (R) | 1.5 | 0.83 ± 0.02 | 5.57 | Yes |
| 15f | -4-Cl, (R) | 3.8 | 0.70 ± 0.02 | 6.08 | Yes |
| 15g | -3-Cl, (R) | 11.2 | 0.77 ± 0.07 | 6.08 | Yes |
| 15h | -4-NO$_2$, (R) | 5.2 | 0.62 ± 0.02 | 5.34 | Yes |

[a]IC$_{50}$: 50% inhibitory concentration for KRASG12V mislocalization. Values were calculated from at least eight data points. In general at least three independent determinations have been performed.
[b]E$_{max}$: Maximal effects elicited by the compounds. At least three independent determinations have been performed.
[c]cLogP: http://biosig.unimelb.edu.au/pkcsm/prediction.

Finally, the significance of linker changes on potency was investigated. As shown in Table 10, each methylene group replaced with a carbonyl group to generate compounds 18 and 20. Neither of these compounds was more potent than 12f (NY0244). However, extended length of the linker by adding a methylene group (compound 22) resulted in a substantially increased KRAS mislocalization potency from 0.1 μM to 20 nM whilst retaining the good efficacy (E$_{max}$=0.81). When the linker was further extended with two methylene groups, the resulting compound 25 displayed a significantly decreased potency. Collectively, the type, shape, and length of the linker impact the potency.

TABLE 10

The IC$_{50}$ and E$_{max}$ Values of ((R)-N-(1-(4-methoxyphenypethyl)-N-(2-(4-methylpiperazin-1-yl)ethyl)-3,3-diphenylprop-2-en-1-amine KRAS compounds

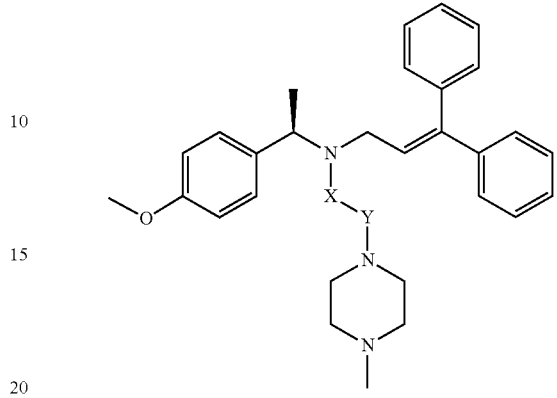

| Compound | X | Y | IC$_{50}$ (μM)[a] | E$_{max}$[b] | cLogP[c] | Cytotoxic at 30 μM |
|---|---|---|---|---|---|---|
| 7 |  |  | 0.5 | 0.74 ± 0.03 | 9.32 | No |
| 12f (NY0244) | CH$_2$ | CH$_2$ | 0.1 | 0.75 ± 0.01 | 5.44 | Yes |
| 20 | CO | CH$_2$ | 7.1 | 0.51 ± 0.02 | 4.96 | Yes |
| 25 | CH$_2$ | (CH$_2$)$_3$ | ND[d] | 0.81 ± 0.03 | 6.22 | Yes |

[a]IC$_{50}$: 50% inhibitory concentration for KRASG12V mislocalization. Values were calculated from at least eight data points. In general at least three independent determinations have been performed.
[b]E$_{max}$: Maximal effects elicited by the compounds. At least three independent determinations have been performed.
[c]cLogP: http://biosig.unimelb.edu.au/pkcsm/prediction.
[d]ND means not determined within the concentration range tested.

Example 3. In Vitro Mechanism of Action Studies of Selected New Analogs

The following criteria were used for the selection of the best analogs for further analysis: (1) IC$_{50}$ less than 0.5 μM, (2) E$_{max}$ greater than 0.75, and (3) cytotoxicity to Madin-Darby Canine Kidney epithelial (MDCK) KRAS G12V cells at 30 μM (which was found to correlate well with the ability of the compound to inhibit proliferation of oncogenic KRAS expressing cancer cell lines).

Figure 6A:
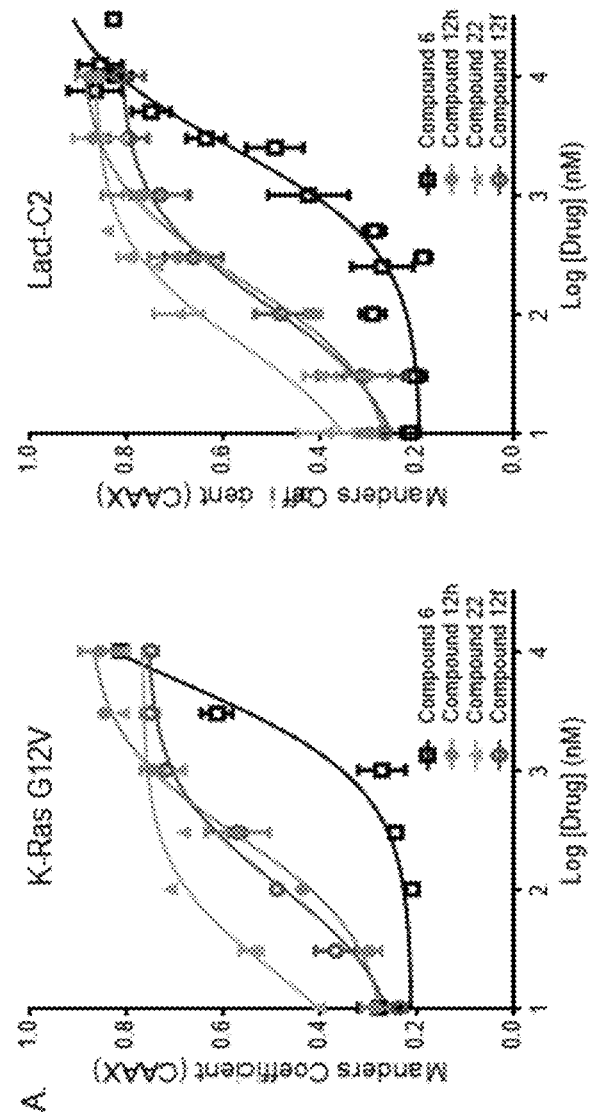
FIG. 6A-C. (A) Dose response curves quantifying the extent of KRASG12V and LactC2 mislocalization after 48 h treatment with compounds. Mislocalization was quantified using Manders coefficients as the fraction of mCherry-CAAX co-localizing with mGFP-KRASG12V or GFP-LactC2. (B) ASM activity in cell stably expressing GFP-tagged SMPD1 treated with DMSO or 5 μM compound for 48 h. (C) Representative western blots and quantitation of SMPD1-GFP levels in cells treated with 5 μM compounds for 48 h. (D) Representative confocal images of MDCK cells stably co-expressing mGFP-KRASG12V and mCherry-CAAX treated with 10 μM compound 6 or 1 μM of compounds 12f (NY0244), 12h (NY0331) or 22 (NY0335) for 48 h (-ASM), then incubated with recombinant ASM in the continued presence of drugs for a further 60 min (+ASM). Mislocalization was quantified using Manders coefficients as the fraction of mCherry-CAAX co-localizing with mGFP-KRASG12V.

Of the new analogs tested in the KRAS mislocalization assay, compounds 12f (NY0244), 12h (NY0331) and 22 (NY0335) were further analyzed. Fendiline (6) was included as the positive control. Compound 6 causes KRAS mislocalization by depleting PtdSer from the inner leaflet of the PtdSer. To determine if the same mechanism operates with the new derivatives, MDCK cells stably co-expressing mCherry-CAAX and mGFP-LactC2, a probe for PtdSer, were treated with the compounds for 48 h and analyzed by quantitative confocal microscopy. The results show that the new analogs disrupt the PM localization of mGFP-LactC2, and by inference PtdSer, with potencies (measured as IC50) very similar to their respective potencies for mislocalizing KRASG12V from the PM (FIG. 6A).

Figure 6B:
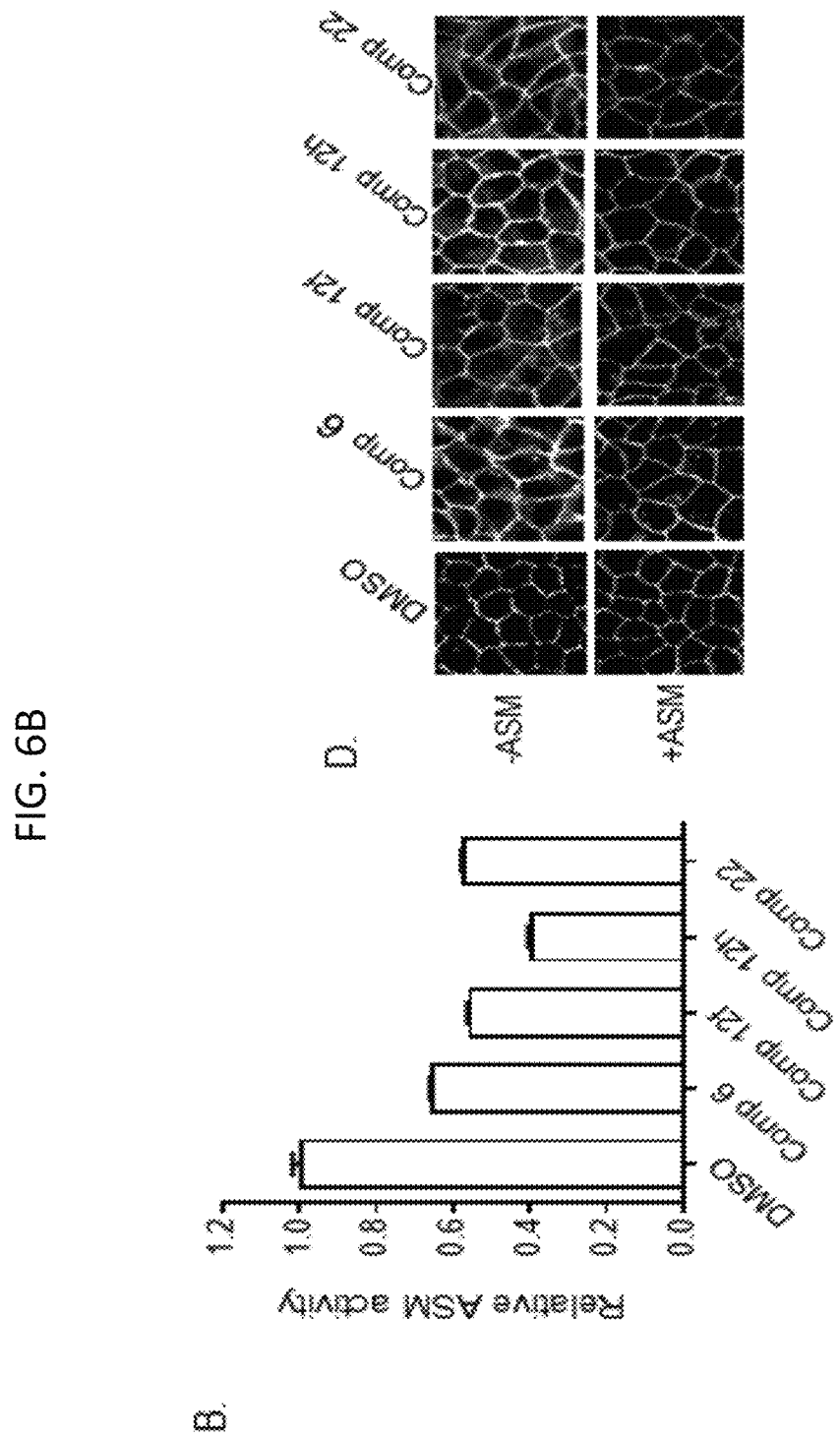
Figure 6C:
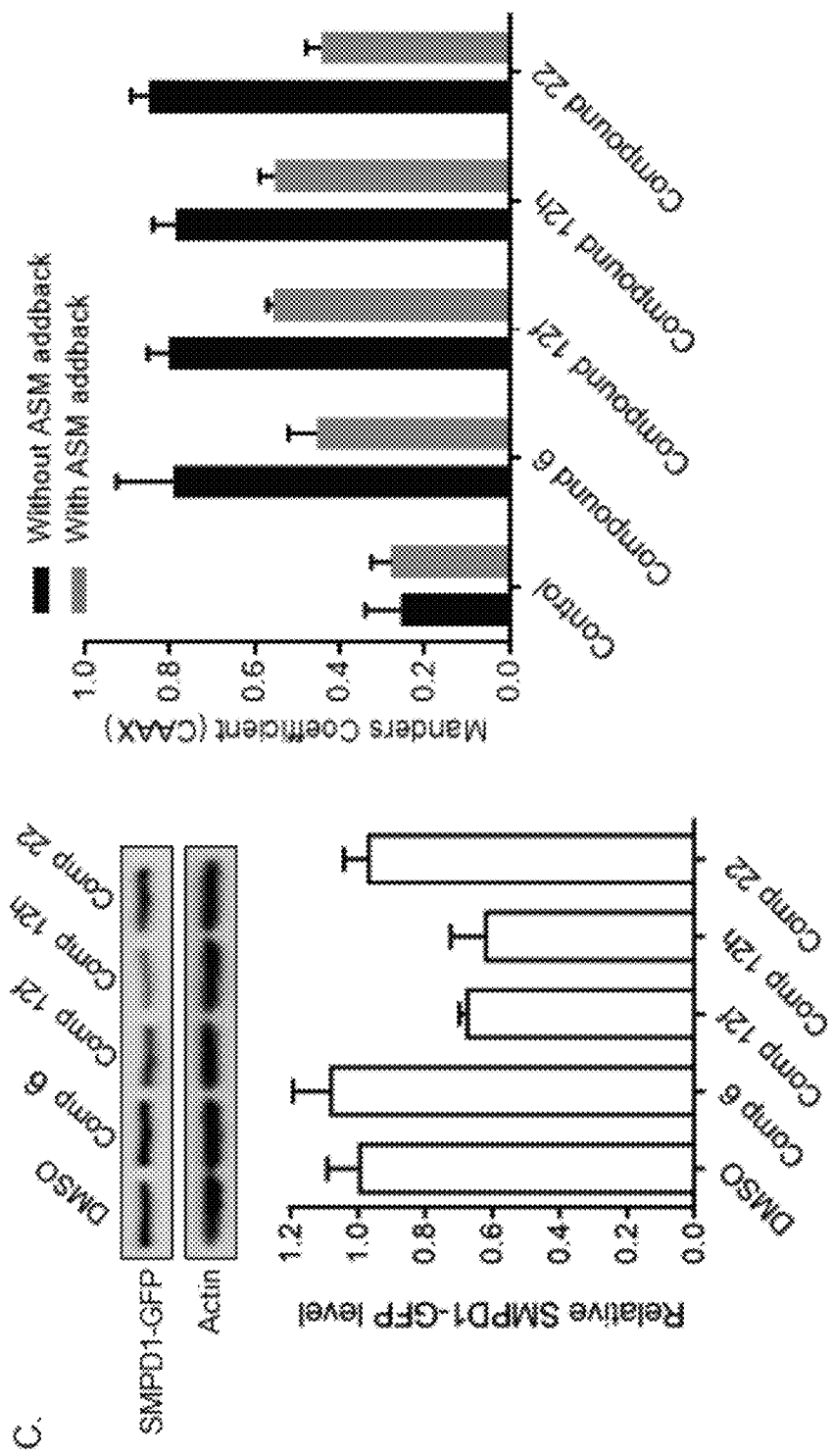

Compound 6 depletes PtdSer from the PM by off-target inhibition of ASM, an enzyme that hydrolyzes sphingomyelin (SM) to ceramide (Cer). ASM-inhibition causes SM loading and aberrant endo-lysosomal function that in turn depletes the PM of PtdSer. To determine if the new derivatives of compound 6 also functioned through the same mechanism, we directly measured inhibition of ASM by the compounds using a sphingomyelinase activity assay. Our results show that all new analogs inhibit ASM with higher potency than compound 6 (FIG. 6B). Compound 12h (NY0331) was the most potent compound in inhibiting ASM. Western blot analysis to determine the effect of the compounds on the cellular levels of ASM revealed that compounds 12f (NY0244) and 12h (NY0331) reduced the levels of ASM while the others had no effect (FIG. 6C). To confirm that KRAS mislocalization occurred as a consequence of ASM inhibition, we supplemented new analog-treated cells with exogenous ASM. As shown in Figure. 6D, ASM supplementation partially corrected the mislocalization of KRASG12V from the PM induced by compounds. These results recapitulate earlier observations with the lead compound 6.

In Vitro Biological Activities against KRAS-Driven Cancer Cell Lines. The growth inhibitory effects of these newly synthesized PMLIs were evaluated against pancreatic, endometrial, colon and lung cancer cell lines, using proliferation assays as described in the in vitro screening protocol (Experimental Section). Overall, the newly synthesized compounds exhibited better anti-proliferation activities than compound 6 in all KRAS-driven cancer cell lines tested, and the results are summarized in Table 11. Concordant with the induced KRAS mislocalization, the selected PMLIs potently inhibited proliferation of pancreatic cancer cell lines with an oncogenic KRAS mutation more so than a pancreatic cancer cell line expressing wild-type (WT) KRAS. A similar selective inhibition of proliferation of oncogenic mutant KRAS expressing cells was also observed in endometrial, lung and colon cancer cell lines following treatment with PMLIs. Compounds 6 and 7 displayed weak activities against mutant KRAS pancreatic cancer cells (MiaPaCa-2, MOH and MPanc96) whereas compounds 12f (NY0244), 12h (NY0331) and 22 (NY0335) significantly inhibited proliferation of these three mutant KRAS pancreatic cancer cell lines at low micromolar concentrations (Table 11). However, they also more potently inhibited proliferation of the WT KRAS expressing BxPC-3 cell line compared to 6. Similarly, compounds 6 and 7 exhibited weak anti-proliferation effects in both WT (KLE, ESS-1 and Ishikawa) and mutant KRAS (HeclA and Hecl B) endometrial cancer cells.

As shown in Table 11, compounds 12f (NY0244), 12h (NY0331) and 22 (NY0335) displayed more potent anti-proliferative activity against KRAS mutant than WT KRAS endometrial cancer cells. Moreover, the anti-proliferation activities of the five selected compounds in colon and lung cancer cells were also tested. Compound 6 displayed high micromolar growth inhibition in all the mutant KRAS-expressing colon cancer cells with no effect on the WT counterpart, while compound 7 showed no inhibitory effect on proliferation of WT and mutant KRAS-expressing lung cancer cell lines, consistent with our previous observations. While new compounds 12f (NY0244), 12h (NY0331) and 22 (NY0335) selectively inhibited the mutant KRAS-expressing lung cancer cell lines. A similar trend was also observed with the colon cancer cell lines. Taken together, compared to lead compounds 6 and 7, our newly identified compounds exhibited significantly improved anti-proliferative activities in almost all of the tested KRAS-driven cancer cells.

TABLE 11

Selected Potent PMLIs Inhibit Proliferation of Pancreatic, Endometrial, Colon and Lung Cancer Cells

| $IC_{50}$ (μM)[a] cancer Cell lines | | 6 | 7 | 12f (NY0244) | 12h (NY0331) | 22 (NY0335) |
|---|---|---|---|---|---|---|
| Pancreatic | BxPC-3 (WT) | 28.6 ± 5.9 | NE[b] | 5.7 | NT[c] | 5.3 |
| | MiaPaCa-2 (Mut) | 9.2 ± 0.6 | NE | 3.0 | 3.1 | 2.8 |
| | MOH (Mut) | 11.1 | NE | 3.7 | 4.0 | 3.8 |
| | MPanc96 (Mut) | 10.8 | NE | 4.2 | 3.8 | 4.2 |
| Endometrial | Ishikawa (WT) | NE | NE | NE | NT | 11.0 |
| | HeclA (Mut) | 9.48 | NE | 2.6 | NT | 2.3 |
| | HeclB (Mut) | 9.8 | NE | 3.3 | NT | 3.9 |
| Colon | Caco-2 (WT) | 14.5 | NE | 5.1 | NT | 4.4 |
| | SK-CO-1 (Mut) | 7.8 | NE | 3.3 | NT | 3.5 |
| Lung | NCI H1975 (WT) | NE | NE | NE | NT | NE |
| | NCI H522 (WT) | 29.6 ± 1.2 | NE | 28.2 | NT | 23.5 ± 3.2 |
| | NCI H1299 (WT) | 24.3 ± 2.1 | NE | 8.2 | NT | 8.2 ± 1.0 |
| | NCI H23 (Mut) | 11.4 ± 1.0 | NE | 3.8 | NT | 4.1 |

[a]$IC_{50}$ values were calculated from at least eight data points. In general at least three independent determinations have been performed. bNE means no effect, indicating that the $IC_{50}$ is beyond the highest testing dose (30 μM). cNT means not tested.

Example 4

Figure 7:
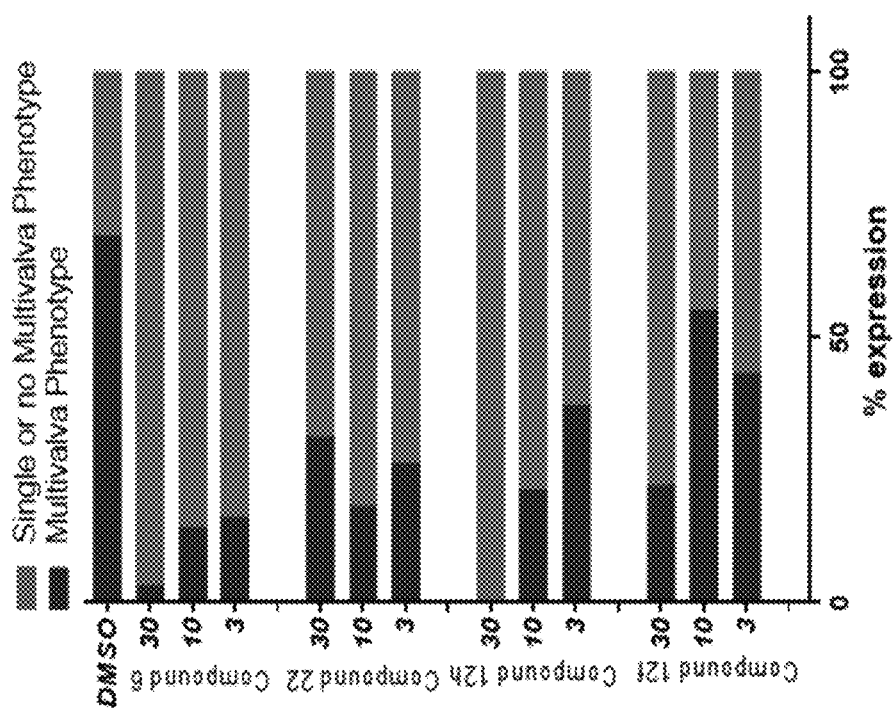
FIG. 7. Strain let-60(n1046) L1 larvae were cultured in M9 buffer containing the E. coli strain OP50 in presence of vehicle (DMSO) or compounds (3, 10 or 30 μM). After 4-5 days, when worms reached the adult stage, they were scored for the presence of the multi-vulva phenotype using DIC/Nomarski microscopy.

In Vivo Biological Activities against KRAS-Driven Tumor Growth. The well-validated invertebrate model system *C. elegans* was used, which has a single RAS gene, let-60, that is a KRAS ortholog to test KRAS inhibition by PMLIs. Activating mutations in let-60 such as LET-60 G13D (n1046) induce a readily quantifiable multi-vulva phenotype. The treatment of these worms with the PMLIs would suppress the multi-vulva phenotype was investigated. L1 larvae were cultured in M9 buffer containing the *E. coli* strain OP50 in presence of DMSO or compounds. After 4-5 days, worms reached the adult stage and were scored for the presence of the multi-vulva phenotype. Compound 6, which we previously showed to potently inhibit the multi-vulva phenotype, was used as the positive control. All of the compounds tested dose-dependently reverted the multi-vulva phenotype to a single-vulva WT phenotype (FIG. 7).

Next the effect of the selected PMLIs on the growth of oncogenic KRAS expressing MiaPaCa-2 cells implanted subcutaneously into the flanks of nu/nu immunosuppressed mice was determined. Given that compounds 12h (NY0331) and 22 (NY0335) were more potent in inhibiting in vitro proliferation and suppressing the multi-vulva phenotype in C. elegans, those two were chosen to be tested in the in vivo tumor growth assays. The animals were randomized into control and PMLI-treated groups (10 mice per group). Treatment was initiated when the tumors reached a mean volume of 100 mm³. PMLIs were tested at 12.5, 7.5, 5, 2.5 and 1 mg/kg doses, administered once daily intraperitoneally for 5 days, with 2 days of no treatment in between for the duration of the experiment. Administration of compounds 12h (NY0331) and 22 (NY0335) strikingly decreased the rate of growth of MiaPaCa-2 cells xenografted in nude mice compared to compound 6 (FIG. 8A) at all doses tested, except at 1 mg/kg (FIG. 8A, results with 12.5 mg/kg and 7.5 mg/kg not shown). At 1 mg/kg, only compound 12h (NY0331) significantly inhibited tumor growth. There was no observed toxicity detected in any of the compound-treated groups during the experiment and, accordingly, there was no significant difference in the body weight of the animals in the different groups. These results demonstrate that compounds 12h (NY0331) and 22 (NY0335) can selectively reduce the growth of oncogenic KRAS-transformed tumors in vivo.

To determine if the reduction in tumor growth elicited by the compounds were mediated by inhibition of ASM, we stained the tissue sections for SM using a non-toxic recombinant fragment of lysenin tagged with GFP (GFP-Lys). In DMSO-treated tumor sections, weak GFP-Lys staining was observed. The GFP-Lys staining was significantly increased in tumors from compounds 6 and 12h(NY0331)-treated mice (12.5 mg/kg), suggesting accumulation of SM with compound treatment. The SM staining was significantly greater with compound 12h (NY0331) compared to compound 6, which corresponds with increased potency of compound 12h (NY0331). Interestingly, compound 22 did not enhance GFP-Lys staining. Compounds 12h (NY0331) and 22 (NY0335) reduced phosphorylated protein kinase RNA-like ER kinase (pERK) levels and increased cleaved caspase 3 (CC3) in tumors whereas compound 6 had no significant effect suggesting that the new analogs are more potent in inhibiting KRAS signaling and inducing apoptosis of tumor cells (FIGS. 8C and 8D). We also observed that the blood vessels were dilated in compound 6 treated tumors, whereas the blood vessel diameters were not changed in compound 12h (NY0331) and 22 (NY0335) treated tumors (FIG. 8E). These results suggest that while compounds 12h (NY0331) and 22 (NY0335) retained the KRAS inhibitory function, they lost the Ca2+ channel blocking function of compound 6.

It is to be understood that the foregoing detailed description is exemplary, and thus does not restrict the scope of the invention.

We claim:
1. A compound according to Formula I or pharmaceutically acceptable salt thereof, wherein:

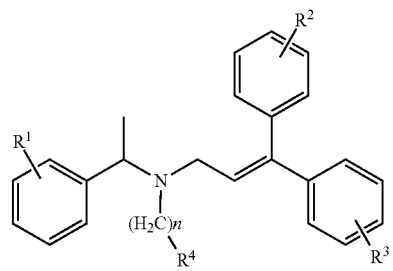

Formula I wherein:
R¹ is independently chosen from H, alkyl, alkoxy, X, cyano, amino, nitro, hydroxyl, CX₃ and -OCX₃, wherein X is F, Cl, Br, or I;
R² is H, alkyl, alkoxy, X, cyano, amino, nitro, hydroxyl and CX₃, wherein X is F, Cl, Br, or I;
R³ is independently chosen from H, alkyl, alkoxy, X, cyan, amino, nitro, hydroxyl and CX₃,
wherein X is F, Cl, Br, or I;
R⁴ is independently chosen from a 5-membered heterocycle and a 6-membered heterocycle; and
n is 1-6.

2. The compound according to claim 1, wherein the compound is:

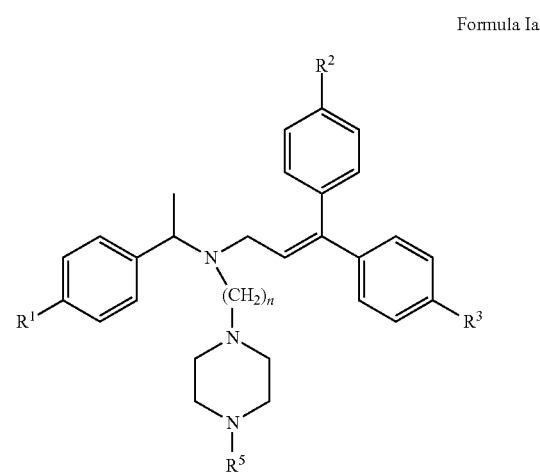

Formula Ia

R¹ is independently chosen from H, alkyl, alkoxy, X, cyano, amino, nitro, hydroxyl, CX₃ and -OCX₃, wherein X is F, Cl, Br, or I;
R² is H, alkyl, alkoxy, X, cyano, amino, nitro, hydroxyl and CX₃, wherein X is F, Cl, Br, or I;
R³ is independently chosen from H, alkyl, alkoxy, X, cyan, amino, nitro, hydroxyl and CX₃,
wherein X is F, Cl, Br, or I;
R⁴ is independently chosen from a 5-membered heterocycle and a 6-membered heterocycle; and
n is 1-6;
wherein R⁵ is H or alkyl.

3. The compound according to claim 1, wherein the compound is:
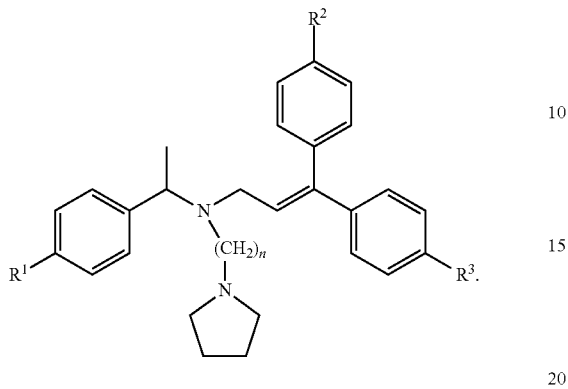
Formula Ib
4. The compound according to claim 1, wherein the compound is one of:
| Name | Structure |
| --- | --- |
| (R)-N-(1-(4-methoxyphenyl)ethyl)-N-(2-(4-methylpiperazin-1-yl)ethyl)-3,3-diphenylprop-2-en-1-amine (NY0244) | 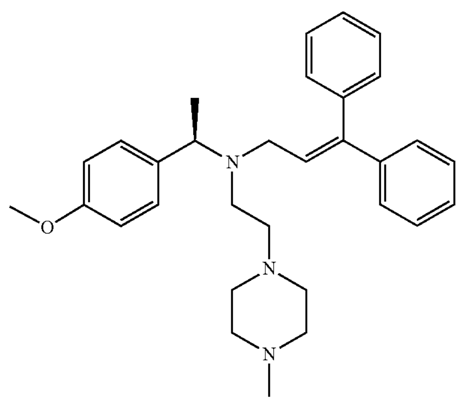 [SMILES: COc1ccc([C@@H](C)N(CC=C(c2ccccc2)c2ccccc2)CCN2CCN(C)CC2)cc1] |
| (R)-N-(1-(4-methoxyphenyl)ethyl)-3,3-diphenyl-N-(2-(pyrrolidin-1-yl)ethyl)prop-2-en-1-amine (NY0331) | 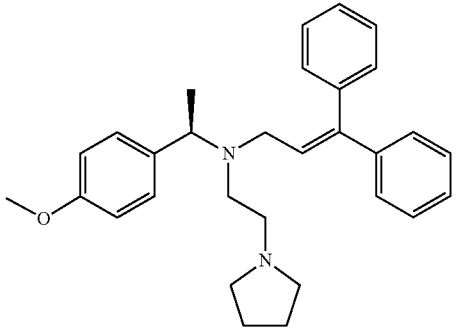 [SMILES: COc1ccc([C@@H](C)N(CC=C(c2ccccc2)c2ccccc2)CCN2CCCC2)cc1] |

| Name | Structure |
|------|-----------|
| (R)-N-(1-(4-methoxyphenyl)ethyl)-N-(3-(4-methylpiperazin-1-yl)propyl)-3,3-diphenylprop-2-en-1-amine (NY0335) | 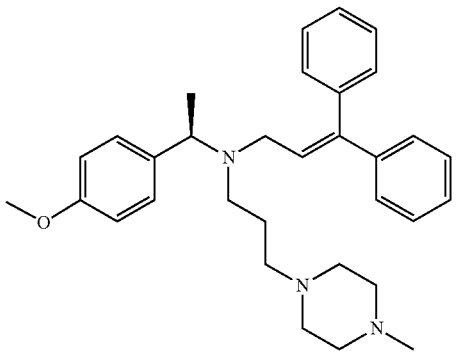 [SMILES: COc1ccc([C@@H](C)N(CC=C(c2ccccc2)c2ccccc2)CCCN2CCN(C)CC2)cc1] |
| (R)-N-(1-(4-fluorophenyl)ethyl)-3,3-diphenyl-N-(2-(pyrrolidin-1-yl)ethyl)prop-2-en-1-amine (NY0506) | 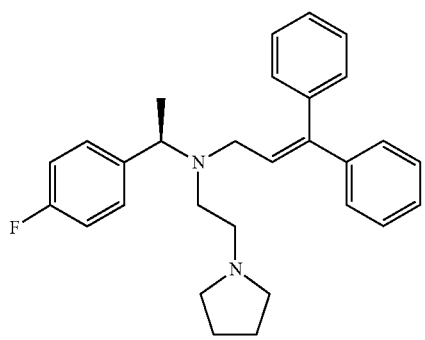 [SMILES: C[C@H](c1ccc(F)cc1)N(CC=C(c1ccccc1)c1ccccc1)CCN1CCCC1] |
| (R)-N-(2-(4-methylpiperazin-1-yl)ethyl)-3,3-diphenyl-N-(1-phenylethyl)prop-2-en-1-amine (NY0513) | 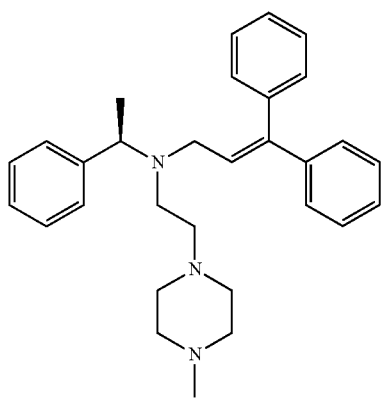 [SMILES: C[C@H](c1ccccc1)N(CC=C(c1ccccc1)c1ccccc1)CCN1CCN(C)CC1] |
| (R,E)-3-(4-fluorophenyl)-N-(1-(4-fluorophenyl)ethyl)-3-(4-methoxyphenyl)-N-(2-(pyrrolidin-1-yl)ethyl)prop-2-en-1-amine (PW0454) | 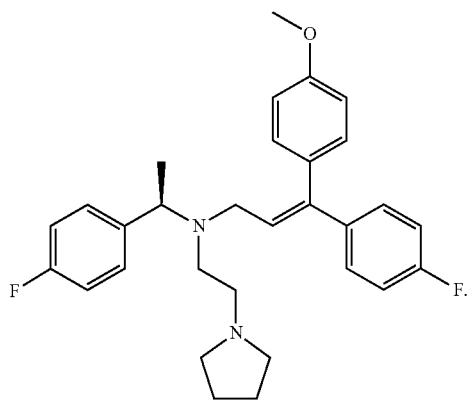 |

5. A compound according to Formula II or pharmaceutically acceptable salt thereof, wherein:

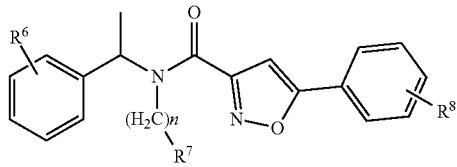

Formula II $R^6$ is independently chosen from H, alkyl, alkoxy, X, cyano, amino, hydroxyl and $CX_3$ and $-OCX_3$, wherein X is F, Cl, Br, or I;

$R^7$ is independently chosen from a 5-membered heterocycle and a 6-membered heterocycle;

$R^8$ is H, alkyl, alkoxy, X, cyano, amino, hydroxyl and $CX_3$, wherein X is F, Cl, Br, or I; and n is 1-6.

6. The compound according to claim 5, wherein the compound is:

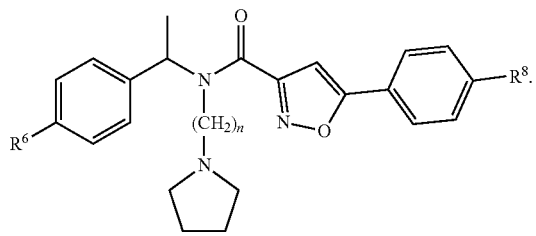

Formula IIa

7. A method of inhibiting K-Ras activity in a subject in need thereof, said method comprising contacting one or more cells of said subject with a therapeutic amount of one or more compounds of Formula I and/or Formula II, or a pharmaceutically acceptable salt thereof, wherein Formula I is:

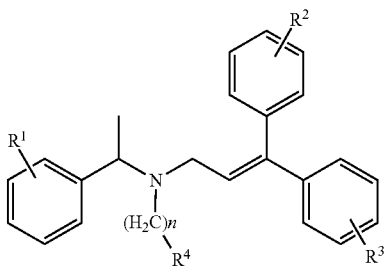

Formula I wherein:
$R^1$ is independently chosen from H, alkyl, alkoxy, X, cyano, amino, nitro, hydroxyl, $CX_3$ and $-OCX_3$, wherein X is F, Cl, Br, or I;
$R^2$ is H, alkyl, alkoxy, X, cyano, amino, nitro, hydroxyl and $CX_3$, wherein X is F, Cl, Br, or I;
$R^3$ is independently chosen from H, alkyl, alkoxy, X, cyan, amino, nitro, hydroxyl and $CX_3$, wherein X is F, Cl, Br, or I;
$R^4$ is independently chosen from a 5-membered heterocycle and a 6-membered heterocycle; and
n is 1-6
and wherein Formula II is:

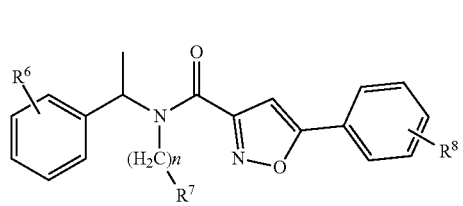

Formula II wherein:
$R^6$ is independently chosen from H, alkyl, alkoxy, X, cyano, amino, hydroxyl and $CX_3$ and $-OCX_3$, wherein X is F, Cl, Br, or I;
$R^7$ is independently chosen from a 5-membered heterocycle and a 6-membered heterocycle;
$R^8$ is H, alkyl, alkoxy, X, cyano, amino, hydroxyl and $CX_3$, wherein X is F, Cl, Br, or I; and
n is 1-6.

* * * * *